(12) United States Patent
Koch et al.

(10) Patent No.: US 9,567,649 B2
(45) Date of Patent: Feb. 14, 2017

(54) SYSTEM FOR IDENTIFICATION OF MICROORGANISM AND DETECTION OF INFECTIOUS DISEASE

(71) Applicants: Jørn Erland Koch, Ry (DK); Magnus Stougaard, Højbjerg (DK); Birgitta Ruth Knudsen, Viby J. (DK); Sissel Juul, Aarhus C (DK); Kam Leong, Durham, NC (US); Yi-Ping Ho, Durham, NC (US); Felicie F. Andersen, Aarhus C (DK)

(72) Inventors: Jørn Erland Koch, Ry (DK); Magnus Stougaard, Højbjerg (DK); Birgitta Ruth Knudsen, Viby J. (DK); Sissel Juul, Aarhus C (DK); Kam Leong, Durham, NC (US); Yi-Ping Ho, Durham, NC (US); Felicie F. Andersen, Aarhus C (DK)

( * ) Notice: Subject to any disclaimer, the term of this patent is extended or adjusted under 35 U.S.C. 154(b) by 257 days.

(21) Appl. No.: 14/064,140

(22) Filed: Oct. 26, 2013

(65) Prior Publication Data
US 2014/0155284 A1 Jun. 5, 2014

Related U.S. Application Data

(63) Continuation-in-part of application No. PCT/DK2012/000056, filed on Apr. 27, 2012, which is a continuation-in-part of application No. PCT/DK2012/050327, filed on Aug. 31, 2012.

(60) Provisional application No. 61/529,352, filed on Aug. 31, 2011.

(30) Foreign Application Priority Data

Apr. 28, 2011 (DK) .................................. 2011 70205
Aug. 31, 2011 (DK) .................................. 2011 70487

(51) Int. Cl.
*C12Q 1/68* (2006.01)
(52) U.S. Cl.
CPC .................................. *C12Q 1/6893* (2013.01)
(58) Field of Classification Search
None
See application file for complete search history.

(56) References Cited

U.S. PATENT DOCUMENTS 6,174,678 B1  1/2001  Menzel et al.
6,316,229 B1 * 11/2001  Lizardi .................. C12Q 1/682
                                                        435/6.1
2004/0091859 A1  5/2004  Didenko et al.
2008/0032944 A1  2/2008  Tsuruyama
2010/0286290 A1  11/2010 Lohmann et al.
2011/0027253 A1  2/2011  Lohmann et al.

FOREIGN PATENT DOCUMENTS

| CA | 2604824 C | 9/1999 |
| WO | 98/04746 | 2/1998 |
| WO | 99/47660 | 9/1999 |
| WO | 2006/044956 A1 | 4/2006 |
| WO | 2007/003938 A2 | 1/2007 |
| WO | 2008/148392 A1 | 12/2008 |
| WO | 2009/006907 A1 | 1/2009 |
| WO | 2009/090311 A2 | 7/2009 |

OTHER PUBLICATIONS

Tesauro, C. Development of a novel Plasmodium falciparum topoisomerase I specific biosensor for diagnosis of malaria. PhD Thesis (2010) Universita degli Studi di Milano, Bicocca, Department of Material Science, pp. 1-107.*
Sloane, Richard D. et al., "The role of unintegrated DNA in HIV infection", Retrovirology, 8(52):1-15 (2011).
Andersen et al., "Multiplexed Detection of Site Specific Recombinase and DNA Topoisomerase Activities at the Single Molecule Level", ACS Nano, 3(12): 4043-4054 (2009).
Annamalai et al., "Analysis of DNA relaxation and cleavage activities of recombinant *Mycobacterium tuberculosis* DNA topoisomerase I from a new expression and purification protocol", BMC Biochemistry 10(18):1-8 (2009).
Aurrecoechea et al., "PlasmoDB: a functional genomic database for malaria parasites", Nucleic Acids Research, 37:D539-D543 (2008).
Cho et al., "Using a Deoxyribozyme Ligase and Rolling Circle Amplification to Detect a non-nucleic Acid Analyte, ATP", J. Am. Chem. Soc., 127: 2022-2023 (2005).
Juul et al., "Detection of Single Enzymatic Events in Rare or Single Cells Using Microfluidics", ACS Nano, 5(10):8305-8310 (2011).
Juul et al., "Microfluidics-Mediated Isothermal Detection of Enzyme Activity at the Single Molecule Level", Engineering in Medicine and Biology Society 2011 Annual International Conference of the IEEE: 3258-3261 (2011).

(Continued)

*Primary Examiner* — David Thomas
(74) *Attorney, Agent, or Firm* — Rodney J. Fuller; Booth Udall Fuller, PLC

(57) ABSTRACT

Methods for the identification of microorganisms or infectious disorders are disclosed, comprising obtaining a suitable sample from sources such as persons, animals, plants, food, water or soil. The methods also comprise providing tailored nucleic acid substrate(s) designed to react with a type 1 topoisomerase from one or more microorganism(s) or infectious agent(s), and incubating said substrate with said sample, or extracts or preparations from the sample, so that the substrate is processed by said topoisomerase if said microorganism(s) or infectious agent(s) is present in the sample. Microfluidic-implemented methods of detecting an enzyme, in particular a DNA-modifying enzyme, are also provided, as well as methods for detecting a cell, or a microorganism expressing said enzyme. The enzyme is detected by providing a nucleic acid substrate, which is specifically targeted by that enzyme.

30 Claims, 28 Drawing Sheets

(56) References Cited

OTHER PUBLICATIONS

Juul et al., "Droplet Microfluidics Platform for Highly Sensitive and Quantitative Detection of Malaria-Causing Plasmodium Parasites Based on Enzyme Activity Measurement", ACS NANO, 6(12):10676-10683 (2012).
Konry et al., "Ultrasensitive Detection of Low-Abundance Surface-Marker Protein using Isothermal Rolling Circle Amplification in Microfluidic Nano-Liter Platform", Small, 7(3):395-400 (Feb. 7, 2011).
Kovarick et al., "Micro Total Analysis Systems: Fundamental Advances and Applications in the Laboratory, Clnic, and Field", Analytical Chemistry, 85(2): 451-472 (2013).
Larsson et al., "In situ genotyping individual DNA molecules by target-primed rolling-circle amplification of padlock probes", Nature Methods, 1(3): 227-232 (Dec. 2004).
Lisby et al., "Enzyme Catalysis and Regulation: Residues within the N-terminal Domain of Human Topoisomerase I Play a Direct Role in Relaxation", J. Biol. Chem, 276:20220-20227 (2001).
Lizardi et al., "Mutation detection and single-molecule counting using isothermal rolling-circle amplification", Nat. Genet. 19:225-232 (Jul. 19, 1998).
Nallur et al., "Signal amplification by rolling circle amplification on DNA microarrays", Nucleic Acid Res., 29(23):1-9 (2001).
Qin et al., "Soft lithography for micro- and nanoscale patterning", Nature Protocols, 5(3): 491-502 (2010).
Smolina et al., "PNA-based microbial pathogen identification and resistance marker detection", Artif. DNA PNA XNA, 1:76-82 (2010).
Stougaard et al., "Single-Molecule Detection of Human Topoisomerase I Cleavage—Ligation Activity", ACS Nano, 3(1):223-233 (2009).
Tesauro et al., "Specific Detection of Topoisomerase I from the Malaria Causing P. falciparum Parasite using Isothermal Rolling Circle Amplification", 34th Annual International Conference of the IEEE Engineering in Medicine and Biology Society: 2416-2419 (2012).
Xu et al., "Exploring both sequence detection and restriction endonuclease cleavage kinetics by recognition site via single-molecule microfluidic trapping", Lab on a Chip Royal Society of Chemistry UK, 11(3): 435-442 (2011).
Yan et al., "An On-Nanoparticle Rolling-Circle Amplification Platform for Ultrasensitive Protein Detection in Biological Fluids", Small, 6(22):2520-2525 (2010).
Yang et al., "Real-Time Rolling Circle Amplification for Protein Detection", Anal. Chem., 79:3320-3329 (2007).
PFE0520c topoisomerase I [Plasmodium falciparum 3D7]. Retrieved Feb. 6, 2014, from http://www.ncbi.nlm.nih.gov/gene/812833 (Sep. 19, 2012).
Topoisomerase I [Plasmodium falciparum 3D7]. Retrieved Feb. 6, 2014 from http://www.ncbi.nlm.nih.gov/protein/XP_001351663.1.
Multiple Sequence Alignment. Retrieved Sep. 29, 2014 from http://web.archive.org/web/20070615000000*/http://www.ebi.ac.uk/clustalW/index.html.
Plasmodium falciparum 3D7 chromosome 5. Retrieved Feb. 6, 2014 from http:/lwww.ncbi.nlm.nih.gov/nuccore/NC_004326?report=genbank&from=445981&to=448500&strand=true.
Poschl et al. "Comparative Diagnosis of Malaria Infections by Microscopy, Nested PCR, and LAMP in Northern Thailand", Am. J. Trop. Med. Hyg., 83(1):56-60 (2010).

\* cited by examiner

Figure 1
B.
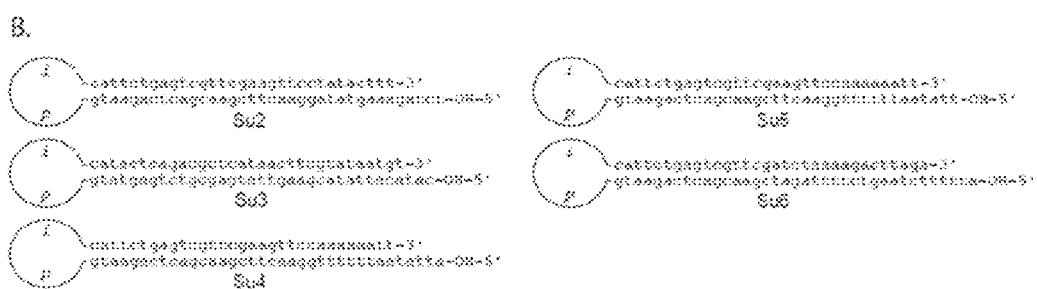
C.
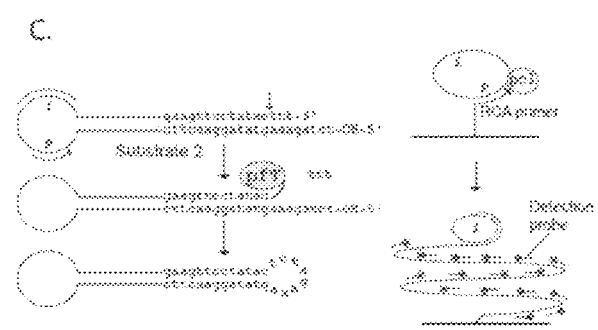
E.
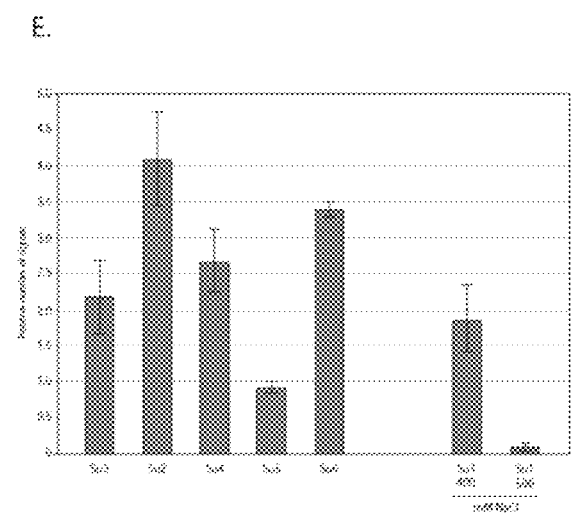

Figure 2
A.
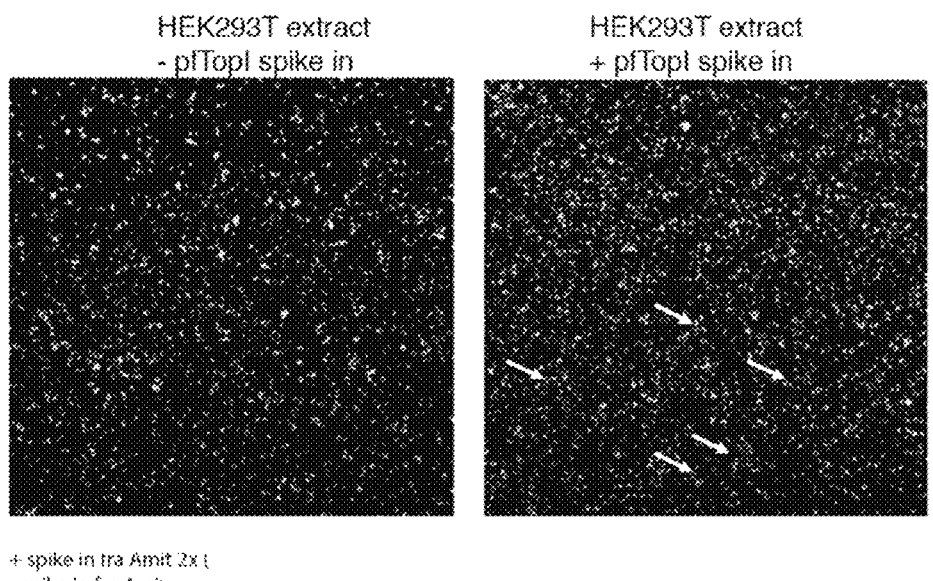
+ spike in fra Amit 2x (
- spike in fra Amit
B.
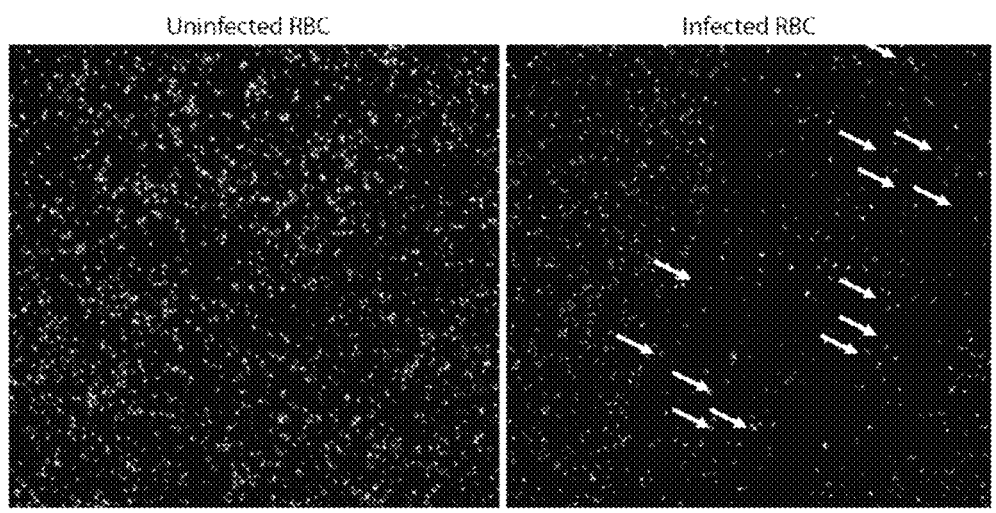

Figure 8
Extract from blood from
P. falciparum infected patient
Extract from blood from
noninfected patient
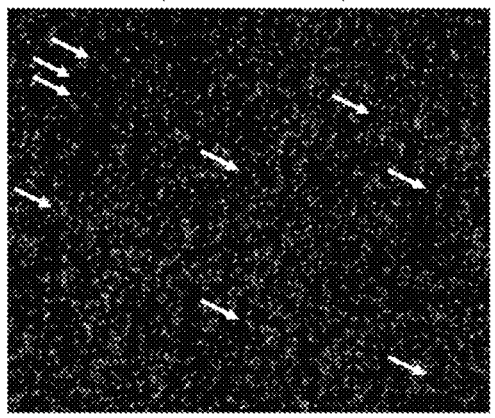
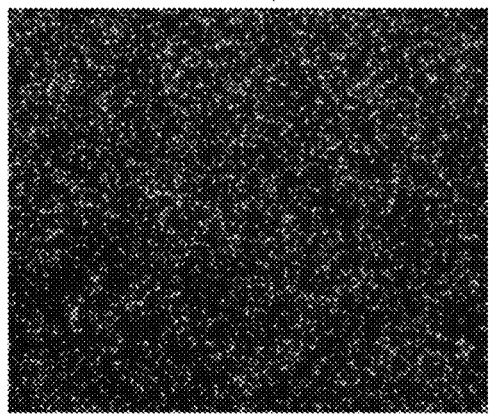
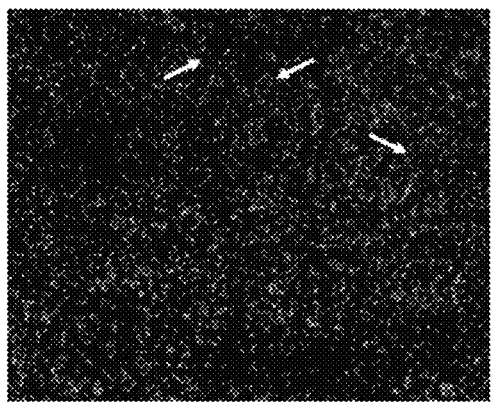
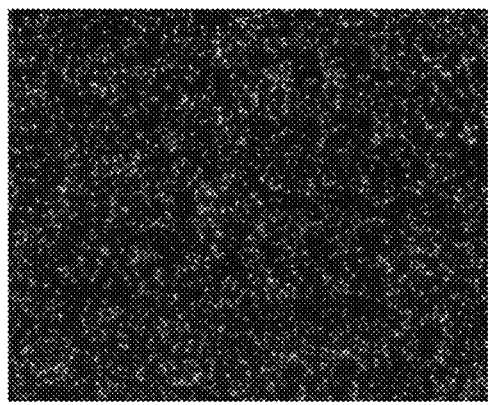

Figure 9

Figure 9, cntd

Figure 11
PfTopI substrat 1
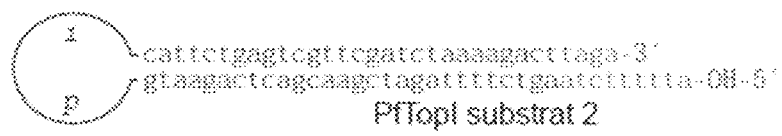
PfTopI substrat 2

Figure 15
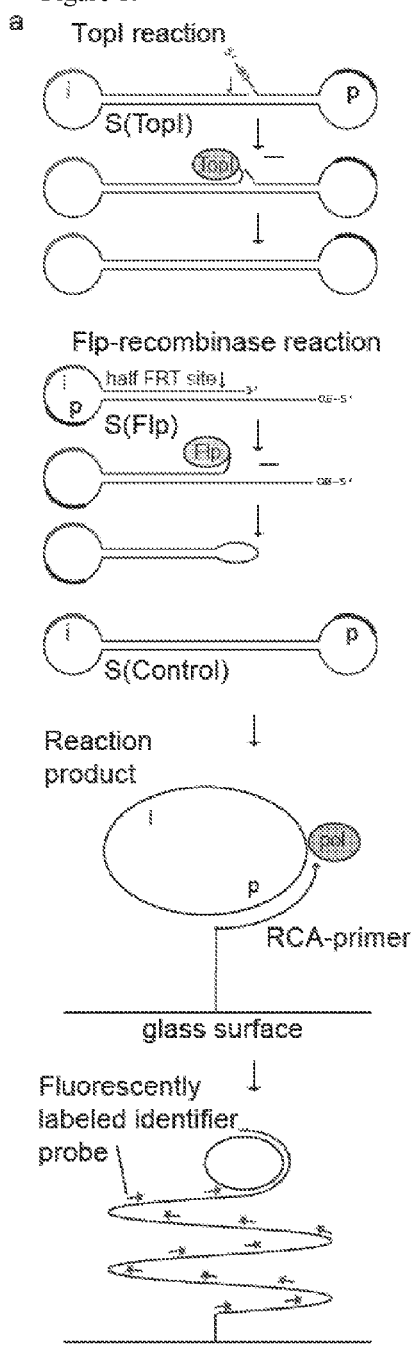
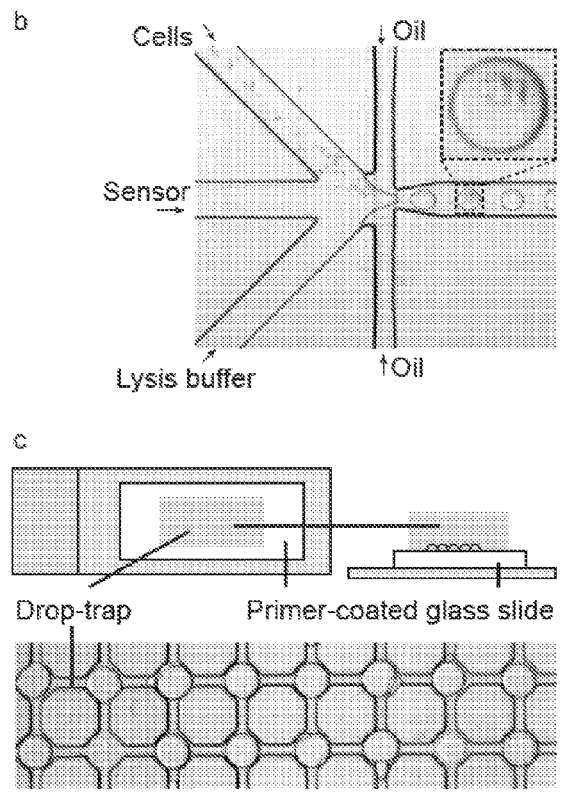
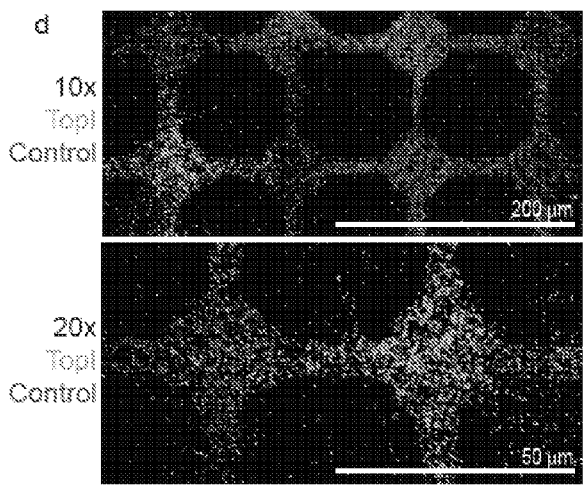

| Cell density (cell/mL) | 5,00E+05 | 1,0E+06 | 2,0E+06 | 3,0E+06 | 4,0E+06 | 5,0E+06 |
|---|---|---|---|---|---|---|
| Droplet Volume (pL) | 100 | 100 | 100 | 100 | 100 | 100 |
| Mean per Drop (cells/drop) | 0,05 | 0,1 | 0,2 | 0,3 | 0,4 | 0,5 |
| Actual cells per drop | | | Probability | | | |
| 0 | 0,951 | 0,905 | 0,819 | 0,741 | 0,670 | 0,607 |
| 1 | 0,048 | 0,090 | 0,164 | 0,222 | 0,268 | 0,303 |
| 2 | 0,001 | 0,005 | 0,016 | 0,033 | 0,054 | 0,076 |
| 3 | 0,000 | 0,000 | 0,001 | 0,003 | 0,007 | 0,013 |
| 4 | 0,000 | 0,000 | 0,000 | 0,000 | 0,001 | 0,002 |
| 5 | 0,000 | 0,000 | 0,000 | 0,000 | 0,000 | 0,000 |
| 6 | 0,000 | 0,000 | 0,000 | 0,000 | 0,000 | 0,000 |
| 7 | 0,000 | 0,000 | 0,000 | 0,000 | 0,000 | 0,000 |
| 8 | 0,000 | 0,000 | 0,000 | 0,000 | 0,000 | 0,000 |
| 9 | 0,000 | 0,000 | 0,000 | 0,000 | 0,000 | 0,000 |
| 10 | 0,000 | 0,000 | 0,000 | 0,000 | 0,000 | 0,000 |

GFP expressing cells: both hTopI and Flp activity.
No GFP expression: only hTopI activity.

Figure 23
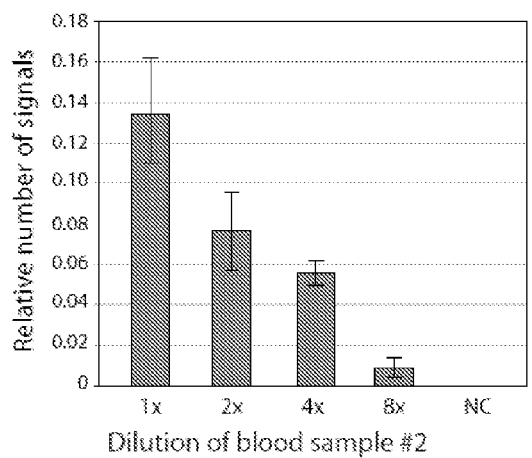
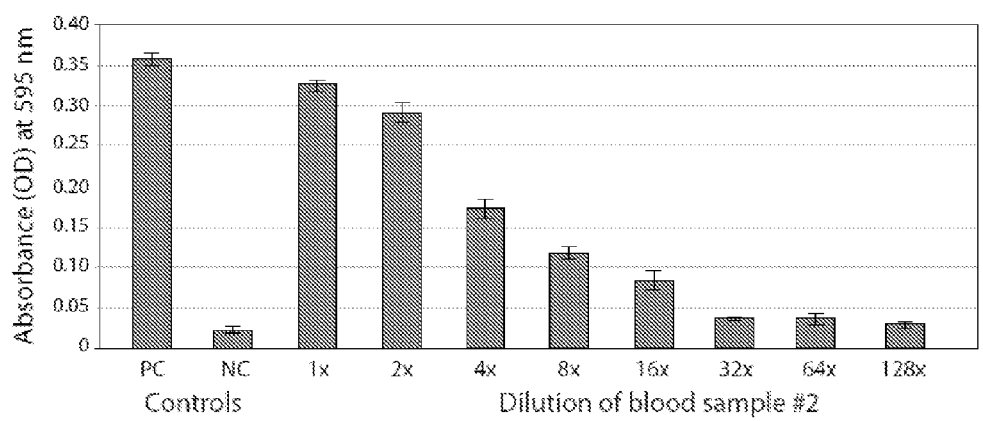

SYSTEM FOR IDENTIFICATION OF MICROORGANISM AND DETECTION OF INFECTIOUS DISEASE

CROSS-REFERENCE TO RELATED APPLICATIONS

The present application claims priority to and is a Continuation-In-Part of International Patent Application No. PCT/DK2012/000056 filed on Apr. 27, 2012, which claims priority to Denmark Patent Application No. PA 2011 70205 filed on Apr. 28, 2011. The present application also claims priority to and is a Continuation-In-Part of International Patent Application No. PCT/DK2012/050327 filed on Aug. 31, 2012, which claims priority to Denmark Patent Application No. PA 2011 70487 filed on Aug. 31, 2011 and to U.S. Patent Application No. 61/529,352 filed on Aug. 31, 2011. Each of the foregoing applications is hereby incorporated by reference in its entirety for all purposes.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 30,049 byte ASCII (text) file named "31311_008_Sequence_Listing" created on Jan. 3, 2014.

FIELD OF INVENTION

The present invention relates to methods of identifying microorganisms, and methods of diagnosing infectious diseases caused by such microorganisms. Furthermore, the invention relates to methods of treatment and compounds for use in the treatments of such infectious diseases.

BACKGROUND OF INVENTION

According to WHO, the prevalence of malaria is between 300-500 million cases worldwide, while approximately 30% of the human population is expected to be infected with tuberculosis. While malaria primarily affects the poorest regions of the world, tuberculosis (TB) is more widespread in both developing and developed countries. Tuberculosis is a global disease, which pose such a big problem that the World Health Organization in 1993 ruled disaster alarm. The majority of tuberculosis sufferers are found in the third world countries, in particular Africa and Southeast Asia, but there are also cases of tuberculosis in western countries, both among natives and immigrants. The global mobility of tuberculosis is increased due to global traffic and tourism, and the problems of the global prevalence of tuberculosis is underscored by the high prevalence of multidrug-resistant tuberculosis that can not be treated with traditional medicine, in particular the Baltic countries.

On a world wide scale, about two to three million people die every year, in particular children and young people. WHO estimated in 2000 that approx. 33% of the world population (about 2 billion people) is infected with tuberculosis; of these, approx. 5-10% develop the disease at some point in their lifetime.

Tuberculosis is an infectious disease caused by inhalation of tuberculosis bacteria (Mycobacteria tuberculosis). These bacteria attack primarily the lungs, and cause a slight infection during the first six weeks without any serious symptoms. From the lungs, the bacteria can spread through the bloodstream to other organs, although still without necessarily doing any damage at first. In many cases, the infection is fought, if the infected person has a good immune system, however, months or years later, the disease may break out in both lungs and other organs if the immune system is weakened for various reasons. Today, outbreak of tuberculosis often occurs in connection with immune system weakening associated with HIV infection, in particular on the African continent. If tuberculosis is spread further in western countries, tuberculosis outbreak are likely to occur also among cancer patients and other patients, where the immune system is challenged.

A person with active tuberculosis infects on average 10 to 15 other people. Infection occurs through the air with tuberculosis bacteria in saliva droplets from cough or sputum from the patient being inhaled by others. Symptoms of tuberculosis such as heavy coughing and spitting does at least in the initial phases of the disease appear very alarming. The danger of infection is especially high in highly populated areas. The increasing global urbanization combined with increased migration is therefore an important factor in the rising number of tuberculosis cases worldwide.

Among the most important factors in fighting the spread of tuberculosis are effective and rapid methods of diagnosis so that persons with active and infectious tuberculosis can be isolated and subject to treatment. Already after fourteen days of antibiotic treatment, the risk of further transmission of the disease is prevented. To halt the spread of antibiotic resistant tuberculosis bacteria and to curb the spread of infection, WHO recommends a treatment strategy to reduced the DOTS (Directly Observed Treatment Short Course) which provides control and monitoring of patients and as such requires a safe, effective and rapid diagnosis of the disease. One of the problems when it comes to slow the spread of tuberculosis is that it has not yet succeeded in developing diagnosis methods that meet the necessary criteria, such as efficient at-bed-side diagnostic tools. Current diagnosis of TB relies on advanced instrumentation and facilities. Furthermore, diagnostics involve a several day long procedure. The method of the present invention, by contrast, is based on simple technology and can be performed and read-out at the bed-side within a few hours, provided that suitable platform development is achieved. When considering that each untreated TB patient on average transfers the infection to 10-15 other persons, early diagnosis allowing early treatment, which immediately prevents transfer of the disease, is of utmost importance.

SUMMARY OF INVENTION

The present invention broadly relates to methods, compounds, compositions and uses thereof for diagnosis, treatment, amelioration and/or prevention of infectious disorders, in particular malaria and tuberculosis. The invention also relates to methods for detection of microorganisms associated with infectious or parasitic disorders, in particular, *Plasmodium falciparum* and *Mycobacterium tuberculosis*.

In one aspect, the present invention relates to a method of identifying a type I topoisomerase-expressing microorganism in a sample, said method comprising
  i. providing the sample
  ii. providing a nucleic acid substrate targeted by a type I topoisomerase of said microorganism,
  iii. bringing the sample of step i. in contact with the nucleic acid substrate of step ii, iv. detecting nucleic acid substrate processed by said type I topoisomerase of said microorganism, wherein the presence of processed nucleic acid substrate is indicative of said microorganism.

In another aspect, the present invention relates to a method of determining a disease in a subject, said method comprising identifying a microorganism in a sample from said subject by a method according to the aspect above, wherein the presence of said microorganism in said sample is indicative of said disease. The subject is any subject, which may be subject to such disease, for example a ruminant, a bovine, a ferret, a badger, a rodent, an elephant, a bird, a pig, a deer, a coyote, a camel, a puma, a fish, a dog, a cat, a non-human primate or a human. The subject is preferably a human subject or a bovine subject, and the disease is preferably an infectious and/or a parasitic disease, such as disease is malaria or tuberculosis, wherein the microorganism is selected from the *Plasmodium* genus or the *Mycobacterium* genus, respectively.

In a further aspect, the invention pertains to a kit comprising a nucleic acid substrate targeted by a type I topoisomerase of a microorganism and means for detection of nucleic acid substrate processed by said topoisomerase.

The invention also in one aspect provides a method for evaluating the effect of an agent on a microorganism in a sample, said method comprising
 i. providing a sample,
 ii. providing a nucleic acid substrate targeted by type I topoisomerase of said microorganism,
 iii. providing an agent,
 iv. combining the sample of step i. and the nucleic acid substrate of step ii. with or without the agent of step iii.
 v. detecting nucleic acid substrate processed by type I topoisomerase of said microorganism with or without the agent,
wherein an agent capable of reducing the amount of processed nucleic acid substrate has an inhibitory effect on said microorganism.

The present invention also relates to microfluidics-implemented methods of detecting enzymes, and microorganisms associated with said enzymes.

In one aspect, the present invention relates to a method of detecting an enzyme, preferably a DNA-modifying enzyme or an agent affecting the activity of such DNA-modifying enzymes, in a sample, said method comprising
a) providing the sample
b) providing a nucleic acid substrate targeted by a said enzymes, c) loading said sample of step a) and said nucleic acid substrate of step b) into a sample chamber comprising a flow through channel, wherein droplets comprising said sample and said nucleic acid substrate are generated,
d) transfer said droplets from said sample chamber to a droplet retaining means through said flow through channel,
e) capturing one or more single droplets in individual cavities of said droplet retaining means, wherein each single droplet is spatially isolated from other droplets, and
f) detecting, in one or more captured droplets, nucleic acid substrate processed by said enzyme, wherein the presence of processed nucleic acid substrate is indicative of the presence of said enzyme.

The detection of enzymatic activities by the method of the invention allows for the detection in a sample of a cell, cell type or microorganism, which express said enzyme. Thus, the invention also in one aspect relates to a method of identifying a microorganism expressing a specific enzyme in a sample, said method comprising a) providing the sample
b) providing a nucleic acid substrate targeted by said specific enzyme of said microorganism,
c) loading said sample of step a) and said nucleic acid substrate of step b) into a sample chamber comprising a flow through channel, wherein droplets comprising said sample and said nucleic acid substrate are generated,
d) transfer said droplets from said sample chamber to a droplet retaining means through said flow through channel,
e) capturing one or more single droplets in individual cavities of said droplet retaining means, wherein each single droplet is spatially isolated from other droplets, and
f) detecting, in one or more captured droplets, nucleic acid substrate processed by said specific enzyme of said cell, cell type or microorganism, wherein the presence of processed nucleic acid substrate is indicative of the presence of said microorganism.

The enzyme detected in the above methods is preferably a DNA-modifying enzyme or an enzyme, protein or agent affecting a DNA modifying enzyme. For example, the enzyme is selected from the group consisting of nucleases, ligases, recombinases, topoisomerases and helicases, preferably a type I topoisomerase.

The invention also in a more specific aspect relates to a method of identifying a type I topoisomerase-expressing microorganism in a sample by a detection assay, which is implemented in a microfluidic system. The detection assay is based on the identification of a type I topoisomerase catalytic activity in the sample by providing a substrate which is specifically targeted and processed by a type I topoisomerase of said microorganism.

Thus, in one aspect, the present invention relates to a method of identifying a type I topoisomerase-expressing cell, cell type or microorganism in a sample, said method comprising
a) providing the sample
b) providing a nucleic acid substrate targeted by a type I topoisomerase of said microorganism,
c) loading said sample of step a) and said nucleic acid substrate of step b) into a sample chamber comprising a flow through channel, wherein droplets comprising said sample and said nucleic acid substrate are generated,
d) transfer said droplets from said sample chamber to a droplet retaining means through said flow through channel,
e) capturing one or more single droplets in individual cavities of said droplet retaining means, wherein each single droplet is spatially isolated from other droplets, and
f) detecting, in one or more captured droplets, nucleic acid substrate processed by said type I topoisomerase of said cell, cell type or microorganism,
wherein the presence of processed nucleic acid substrate is indicative of the presence of said cell, cell type or microorganism. Since, a type I topoisomerase-expressing microorganism identified by the method defined above may be involved in disease or pollution, the present also pertains to methods of determining a disease associated with a type I topoisomerase-expressing microorganism and/or contamination of e.g. foods or water with such microorganisms. So, the present invention also relates to methods for diagnosis, treatment, amelioration and/or prevention of diseases, which are associated with a microorganism, for example infectious diseases, in particular malaria and tuberculosis. The invention also relates to methods for detection of microorganisms associated with infectious or parasitic diseases, in particular, *Plasmodium* and *Mycobacterium*. Thus, in one aspect, the present invention relates to a method of determining a disease in a subject, said method comprising identifying a cell, cell type or microorganism in a sample from said subject by a method comprising the steps of
a) providing the sample
b) providing a nucleic acid substrate targeted by an enzyme, such as a type I topoisomerase of said cell, cell type or microorganism,
c) loading said sample of step a) and said nucleic acid substrate of step b) into a sample chamber comprising a flow through channel, wherein droplets comprising said sample and said nucleic acid substrate are generated,
d) transfer said droplets from said sample chamber to a droplet retaining means through said flow through channel,
e) capturing one or more single droplets in individual cavities of said droplet retaining means, wherein each single droplet is spatially isolated from other droplets, and
f) detecting, in one or more captured droplets, nucleic acid substrate processed by said enzyme, such as type I topoisomerase of said cell, cell type or microorganism, wherein the presence of processed nucleic acid substrate is indicative of the presence of said cell, cell type or microorganism, wherein the presence of said microorganism in said sample is indicative of said disease. In preferred embodiments, the disease is an infectious disease, such as malaria and said microorganism is selected from the *Plasmodium* genus. In other preferred embodiments, the disease is an infectious disease, such as human and/or bovine tuberculosis and said microorganism is selected from the *Mycobacterium* genus, for example *Mycobacterium tuberculosis* for humans and *Mycobacterium bovis* for bovines.

In yet another aspect, the invention relates to a method for evaluating the effect of an agent on a cell, cell type or microorganism in a sample, said method comprising
a) providing a sample comprising said enzyme, cell, cell type and/or microorganism,
b) providing a nucleic acid substrate targeted by said enzyme, and/or an enzyme of said cell, cell type and/or microorganism,
c) providing a chemical agent,
d) loading said sample of step a), said nucleic acid substrate of step b) and said agent of step
c) into a sample chamber comprising a flow through channel, wherein droplets comprising said sample, nucleic acid substrate and agent are generated,
e) transfer said droplets from said sample chamber to a droplet retaining means through said flow through channel,
f) capturing one or more single droplets in individual cavities of said droplet retaining means, wherein each single droplet is spatially isolated from other droplets, and
g) detecting, in one or more captured droplets, nucleic acid substrate processed by said enzyme, and/or enzyme of said cell, cell type and/or microorganism, wherein a chemical agent capable of reducing the amount of processed nucleic acid substrate has an inhibitory effect on said enzyme, and/or enzyme of said cell, cell type and/or microorganism.

The enzyme is preferably a DNA-modifying enzyme, such as most preferably a type I topoisomerase.

BRIEF DESCRIPTION OF DRAWINGS

FIG. 1. Design and test of pfTopI specific substrate. A. shows the pfTopI cleavage sites on a selected doublestranded DNA fragment containing the classical hexadeceameric sequence from tetrahymena rDNA, which is a well know preferred cleavage site for nuclear type IB topoisomerases. B. Shows the five substrates tested for circularization by pfTopI and hTopI. C. A schematic illustration of the RCA based detection of pfTopI cleavage-ligation activity exemplified by Su2. Right panel shows how cleavage by pfTopI at the site indicated by arrow generate covalent cleavage intermediates, which supports ligation of the free 5'-OH end of the substrate resulting in the generation of closed circles. Right panel shows annealling of the pfTopI generated DNA circle to a specific primer attached to a glass surface. This primer supports Rolling Circle Amplification of the generated DNA circle (top left panel) generating 103 tandem repeats for a sequence complementary to the template DNA circle. The product of RCA is hybridized to specific fluorescent labelled probes (bottom left panel), allowing their visualization at the single molecule level using a fluorescent microscope. D. is an example of microscopic pictures obtained upon incubation of Su2 with either pfTopI (left panel) or hTopI (right panel) followed by RCA and hybridization to fluorescent probes. The red dots represents single RCA products of circularized Su2. The green dots represents single RCA products of a closed control circle added to the sample in a known concentration to allow quantification of the results. E. Graphic representation of the results obtained when incubating each of the substrates Su2-Su6 or Su1 in the presence of 400 or 500 mM NaCl (which prevented circularization by hTopI) with pfTopI using the RCA-based visualization approach. The amount of products generated by RCA of circularized substrate was quantified relative to the amount of products obtained by RCA of added spike-in control circle.

FIG. 2. A. a representative example of the view in the microscope obtained when whole cell extract from HEK293T without (left panel) or with (right panel) spike-in purified pfTopI was incubated with Su1 and Su2 prior to addition of known concentration of control circles, RCA and hybridization of the resulting products with fluorescent labelled probes. Blue spots represent products generated by RCA of control circles, green spots are products generated by RCA of Su1, and red spots are products are generated by RCA of Su2. B. a representative example of the view in the microscope obtained when extracts from uninfected (left panel) or *P. falciparum* infected (right panel) RBC was incubated with Su1 and Su2 and analysed as described for "A".

FIG. 8. Examples of the view in the microscope obtained when blood extract from infected (left panel) or noninfected (right panel) was incubated with Su1 and Su2 prior to addition of known concentration of control circles, RCA and hybridization of the resulting products with fluorescent labelled probes. Blue (dark) spots represent products generated by RCA of control circles, green (light) spots are products generated by RCA of Su1, and red spots (indicated by arrows) are products are generated by RCA of Su2.

Figure 9:
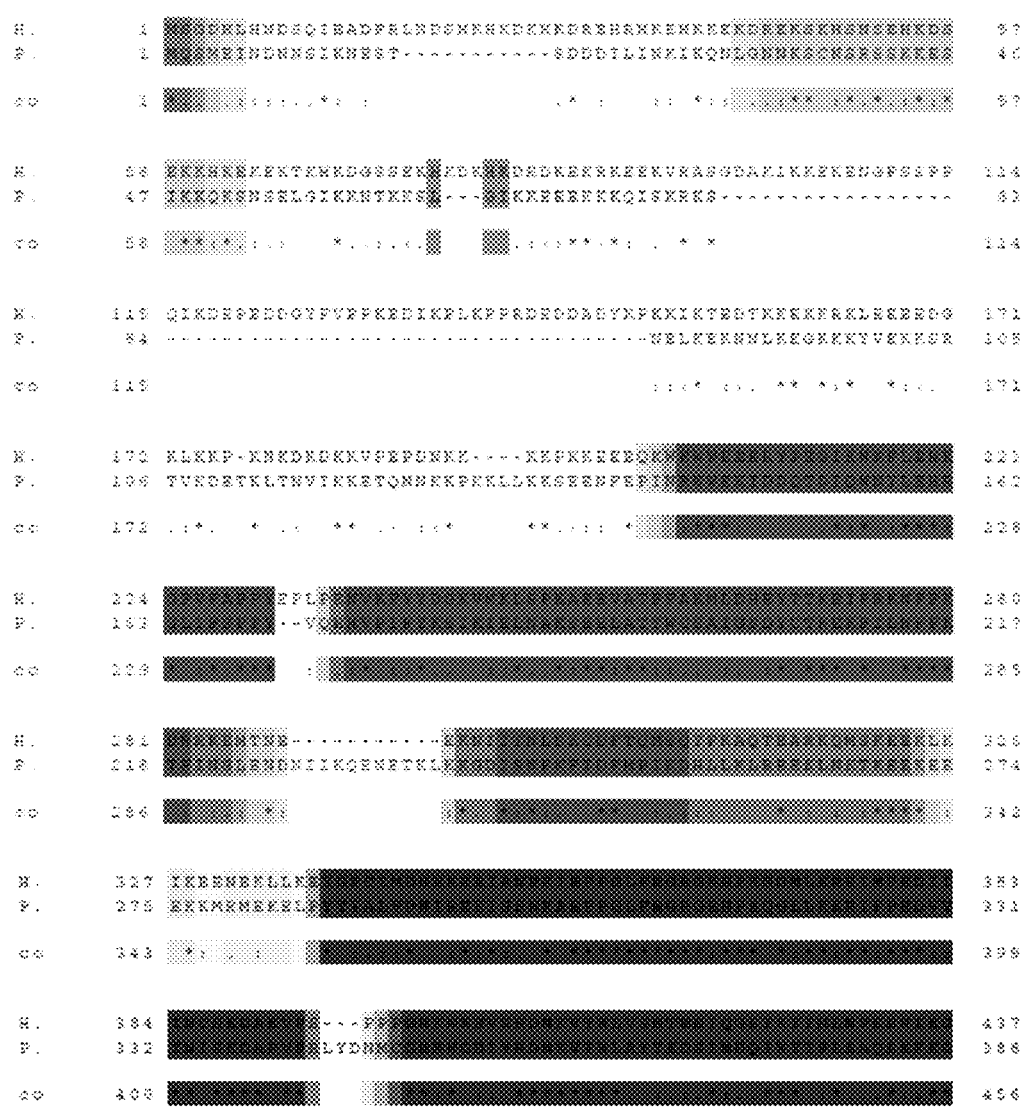
Figure 9:
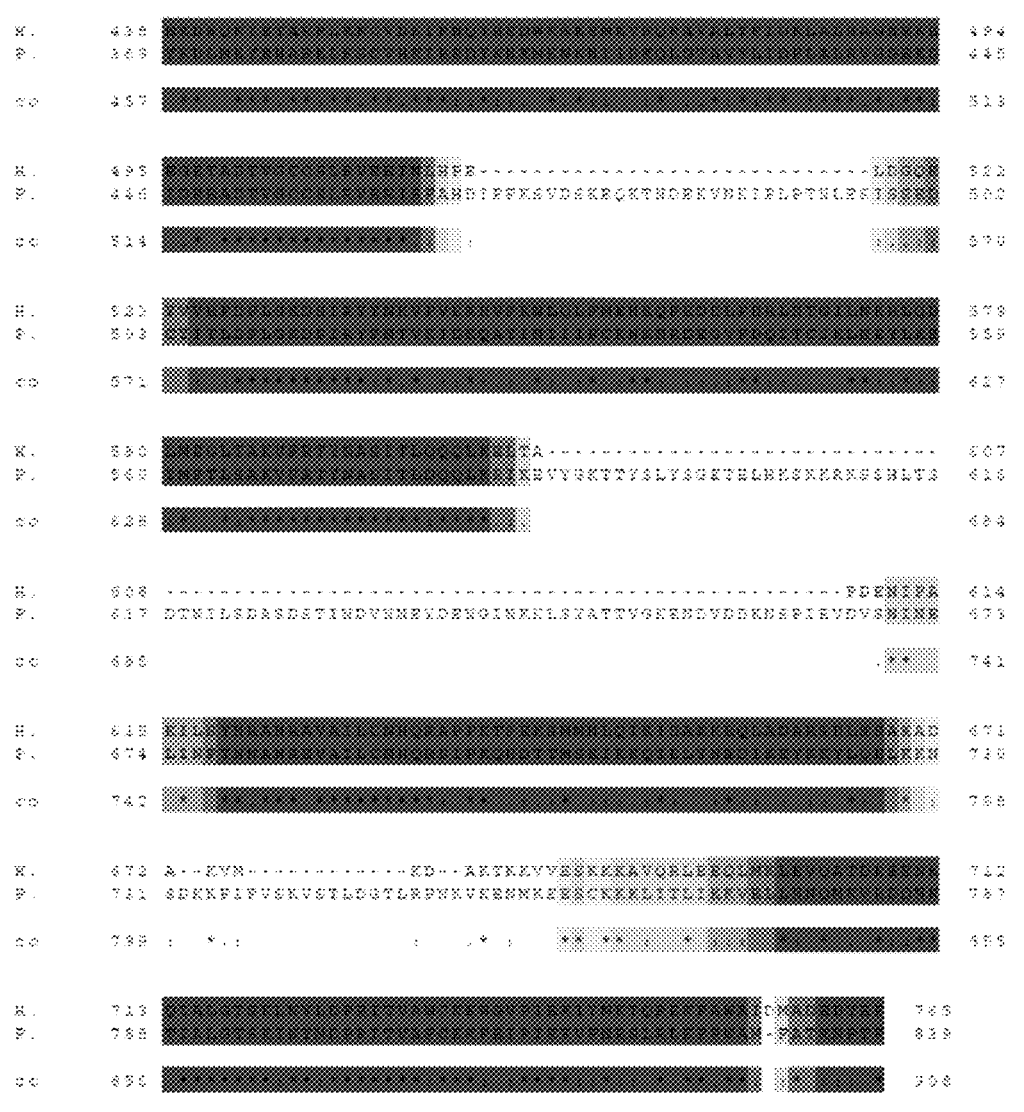

FIG. 9. Alignment of human (H) and *Plasmodium falciparum* (P) type I topoisomerase.

FIG. 11. pfTopI substrates secondary structure

FIG. 15. The combined REEAD-microfluidic experimental setup (a) S(TopI) and S(Flp) are each composed of an oligonucleotide that folds onto itself to allow cleavage-ligation by hTopI and Flp, respectively. These reactions circularize the substrates. S(TopI), S(Flp), and S(control) all contain a specific primer annealing p-element and a probe annealing i-element. The circles allow solid-support RCA generating ~103 tandem repeat RCPs that are visualized in a microscope at the single-molecule level by hybridization of fluorescent probes, (b) The microfluidic setup. Cells-to-be-analyzed, DNA substrate(s) and lysis buffer are, by competitions with oil, confined in picoliter droplets in which DNA circularization takes place, (c) The droplets are confined in a drop-trap on a primer-coated glass slide on which RCA takes place, (d) The result of measuring hTopI activity using five million cells/mL in the combined REEAD-microfluidic setup. As a positive control S(control) was applied together with S(TopI). hTopI and S(control) specific signals were visualized by FAM-(green/light spots) and Cy5-(blue/dark spots) labeled probes, respectively.

FIG. 23. Strategies to increase the sensitivity of pfTopl-specific REEAD. a, Bar chart showing a quantitative depiction of the results obtained when analysing 2×-8× dilutions of extracts from the pauci-parasitic blood sample #2 by REEAD using only 51. To allow quantification, control-circle was added to the reaction mixtures before RCA. The efficiency of pfTopl-specific REEAD at these conditions was estimated by dividing the number of 51 specific signals with the number of control-circle specific signals in 15-30 microscopic views of three individual experiments. NC is a negative control in which sample #2 was replaced with extract from three different uninfected blood samples. No 51 originating signals were observed in 30 microscopic views of each of these reactions, b, Shows the result of spectrophotometric measurements obtained when analyzing 2×-128× dilutions of extracts from blood sample #2 in REEAD combined with HRP-mediated colorimetric readout in three individual experiments. PC is a positive control obtained by reacting 51 with purified recombinant pfTopl before HRP-REEAD and NC is a negative control obtained by incubation of 51 with extract from the uninfected blood sample #1 before REEAD analysis using HRP-mediated colorimetric readout.

DETAILED DESCRIPTION OF THE INVENTION

Figure 3:
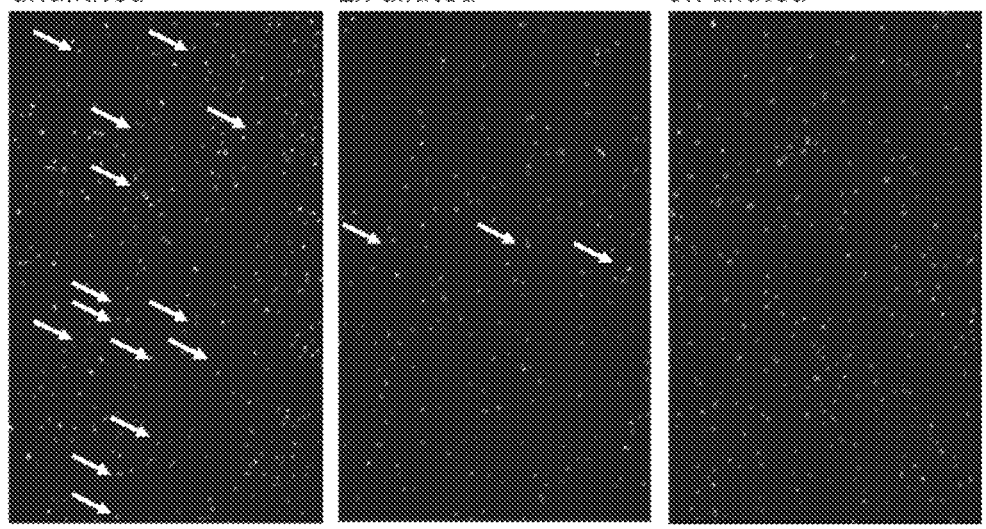
FIG. 3. A. a representative example of the view in the microscope obtained extracts from undiluted (left panel), two times diluted (middle panel) or five times diluted extracts from *P. falciparum* infected (right panel) RBC was incubated with Su1 and Su2 and analysed using the RCA-based detection system after addition of control circle. C. shows the results of subjecting a genomic DNA preparation obtained from uninfected (lanes 1 and 2) or *P. falciparum* infected RBCs for PCR analysis using *P. falciparum* specific (odd lane numbers) or *Plasmodium* sp. specific (even lane numbers) primers. In the samples loaded in lanes 3 and 4, 5 and 6, or 7 and 8 the genomic DNA preparation was diluted 105, 107 or 108 times before PCR analyses. The PCR products were separated in a 1% agarose gel and visualized by EtBr staining FIG. 4. Schematic representation of the biosensor setup. A. topoisomerase I substrate. B. Detection of topoisomerase I activity on a dumbbell substrate followed by rolling circle amplification detection.

A nucleic acid based biosensor setup is provided herein with potential use for at-point-of-care diagnosis of infectious disorders, such as malaria or tuberculosis as well as for the fast screening of drugs against the disease-causing *Plasmodium* or Mycobacterial pathogens. In the developed setup, specific detection of pathogenic microorganisms, such as malaria parasites, in biological samples, such as crude blood samples, is facilitated by specific enzymatic activities of the pathogenic microorganism, happening within nanometer dimensions, to micrometer-sized products readily detectable at the single molecule level in a fluorescence microscope. A specific example if such enzymatic activity is the conversion of single *P. falciparum* topoisomerase I (pfTopI) mediated cleavage-ligation events. This biosensor system requires no special equipment and the readout is adaptable to simple colorimetric detection systems. In addition, the sensitivity of the present biosensor setup is clearly superior to standard cold immuno-based diagnostics. Therefore, the presented biosensor is an easy-to-use diagnostic tool, suitable even for the malaria epidemic areas in developing countries.

The present invention relates to methods of identifying a microorganism, and methods of diagnosing infectious disorders caused by such microorganism. Furthermore, the invention relates to methods of treatment and compounds for use in the treatments of such infectious disorders. Generally, the microorganism is identified on the basis of its expression of a DNA modifying enzyme, which is specific for that particular microorganism, in particular DNA modifying enzymes which display a site-specific DNA modifying activity. In this way, specific nucleic acid substrates are employed, which comprise a sequence specifically targeted by the enzymes in question, where the processing of that substrate is indicative of the presence of that particular microorganism.

The present invention, thus, provides a generic platform for detecting any organism that expresses its own variant of a DNA modifying enzyme. The concept of the invention extends to any enzyme system, such as nucleases, phosphatises, phosphorylases, topoisomerases and others, including DNA modifying enzymes systems, where a cascade of enzymes works to modify a nucleic acid target.

The method of the present invention is highly sensitive and simple, and requires only a short reaction time before an answer is obtained with respect to the presence of a microorganism.

A microfluidics-implemented nucleic acid based biosensor setup is also provided herein. The system can be employed for detection of enzymes/enzymatic activities, particularly DNA-modifying enzymes, as well as for identifying specific cells, cell types or microorganisms, which express such specific enzymes. The microfluidics-implemented methods has potential use for at-point-of-care diagnosis of infectious disorders, such as malaria or tuberculosis as well as for the fast screening of drugs against the disease-causing *Plasmodium* or Mycobacterial pathogens. The system may also be used for sorting cells on the basis of their enzymatic expression profile, for example for sorting cells of a cancer tumour into separate population on the basis of their enzymatic activities for example the activity and specificity of type I topoisomerases of the different cells of the tumour. In the developed setup, specific detection of pathogenic microorganisms, such as malaria parasites, in biological samples, such as crude blood samples, is facilitated by specific enzymatic activities of the pathogenic microorganism, happening within nanometer dimensions, to micrometer-sized products readily detectable at the single molecule level in a fluorescence microscope. A specific example of such enzymatic activity is the conversion of single *P. falciparum* topoisomerase I (pfTopI) mediated cleavage-ligation events. The sensitivity of the presented microfluidics-implemented biosensor setup is clearly superior to standard cold immuno-based diagnostics.

The present invention relates to methods of detecting enzymatic activities and/or enzymes; identifying a microorganism, and methods of diagnosing infectious disorders caused by such microorganism. Furthermore, the invention relates to methods of treatment and compounds for use in the treatments of such infectious disorders.

Moreover, the invention provides methods of sorting cells based on the enzymatic expression profile of the analysed cells.

The present invention, thus, provides a generic platform for detecting any enzyme or enzymatic activity, such as a DNA modifying enzyme or DNA modifying activity. The method of the invention is thus also applicable to the detection of any organism that expresses its own variant of such an enzyme, for example specific variant of a DNA modifying enzyme. The concept of the invention, however, extends to any enzyme system, such as nucleases, phosphatises, phosphorylases, topoisomerases and others, including DNA modifying enzymes systems, where a cascade of enzymes works to modify a nucleic acid target. The method of the present invention is highly sensitive and simple, and requires only a short reaction time before an answer is obtained with respect to the presence of a microorganism.

DEFINITIONS

To facilitate the understanding of the invention, some definitions of important terms are provided herein below.

As used herein, "nucleic acid" or "polynucleotide" or "oligonucleotide" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Polynucleotides can be composed of monomers that are naturally-occurring nucleotides (such as DNA and RNA), or analogs of naturally-occurring nucleotides (e.g., (alpha-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "polynucleotide" also includes so-called "peptide nucleic acids," which comprise naturally-occurring or modified nucleic acid bases attached to a polyamide backbone. Nucleic acids can be either single stranded or double stranded.

The term "complement" or "complementary" in terms of a nucleic acid sequence refers to a polynucleotide having a complementary nucleotide sequence and reverse orientation as compared to a reference nucleotide sequence. For example, the sequence 5' ATGCACGGG 3' is complementary to 5' CCCGTGCAT 3'.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

The term 'nucleotides' as used herein refers to both natural nucleotides and non-natural nucleotides, which are capable of being incorporated into an oligonucleotide, such as a splice-switching oligonucleotide. Nucleotides may differ from natural nucleotides by having a different phosphate moiety, sugar moiety and/or base moiety. Nucleotides may accordingly be bound to their respective neighbour(s) in a template or a complementing template by a natural bond in the form of a phosphodiester bond, or in the form of a non-natural bond, such as e.g. a peptide bond as in the case of PNA (peptide nucleic acids).

The terms "disease" and "disorder" are used interchangeable herein, and are contemplated as synonymous. No specific meaning is intended from one of these terms over the other. A disease is understood as an abnormal condition of the organism that impairs bodily functions, and is associated with specific symptoms and signs. It may be caused by external factors, such as infectious and/or parasitic agents.

Sequence Identity

The term "sequence identity" indicates a quantitative measure of the degree of homology between two amino acid sequences or between two nucleic acid sequences of equal length. If the two sequences to be compared are not of equal length, they must be aligned to give the best possible fit, allowing the insertion of gaps or, alternatively, truncation at the ends of the polypeptide sequences or nucleotide sequences. The sequence identity can be calculated, wherein Ndif is the total number of non-identical residues in the two sequences when aligned and wherein Nref is the number of residues in one of the sequences, preferably sequence identity is calculated over the full length reference as provided herein. Hence, the DNA sequence AGTCAGTC will have a sequence identity of 75% with the sequence AATCAATC (Ndif=2 and Nref=8). A gap is counted as non-identity of the specific residue(s), i.e. the DNA sequence AGTGTC will have a sequence identity of 75% with the DNA sequence AGTCAGTC (Ndif=2 and Nref=8).

With respect to all embodiments of the invention relating to nucleotide sequences, the percentage of sequence identity between one or more sequences may also be based on alignments using the clustalW software (http:/www.ebi.ac.uk/clustalW/index.html) with default settings. For nucleotide sequence alignments these settings are: Alignment=3Dfull, Gap Open 10.00, Gap Ext. 0.20, Gap separation Dist. 4, DNA weight matrix: identity (IUB).

The following terms are used to describe the sequence relationships between two or more polynucleotides: "predetermined sequence", "comparison window", "sequence identity", "percentage of sequence identity", and "substantial identity".

A "predetermined sequence" is a defined sequence used as a basis for a sequence comparison; a predetermined sequence may be a subset of a larger sequence, for example, as a segment of a full-length DNA or gene sequence given in a sequence listing, such as a polynucleotide sequence as disclosed herein or may comprise a complete DNA or gene sequence. Generally, a predetermined sequence is at least 20 nucleotides in length, frequently at least 25 nucleotides in length, and often at least 50 nucleotides in length. Likewise, the predetermined sequence is that of the polypeptides of the invention.

The term "diagnosticum" refers in the present context to a compound or composition used in diagnosis of a disease or medical state. In the present text the diagnosticum is a binding member or a detection member of the present invention or active derivative thereof for use in the diagnosis of a disease or condition, as described herein above. The nucleic acid substrate of the invention may be used as a diagnosticum, Thus, in an aspect the invention relates to nucleic acid substrate according to the invention for use as a diagnosticum.

Cells, Cell Types and Microorganisms

The present invention relates to methods for identification of specific cells, cell types and/or microorganisms. The term "cells" are meant to encompass cells of different origin, while the term "cell types" more refers to cells of the same origin, which may have undergone changes, which allows those cells to be distinguished. The methods of the invention are applicable for separating cells of different origin, such as parasitic cells from mammalian cells, but they are also applicable for distinguishing for example human cancer cells from human non-cancer cells. In the latter case, the cells are both human cells, but are different cell types, because one of the cell types has diverged into a cancerous cell, and the changes that the cell has undergone in the process of its transformation can be detected via altered enzymatic activities.

Method for Enzyme Detection

The present invention in one aspect relates to a microfluidics-implemented method of detecting an enzymatic activity in a sample. The invention relates to a method of detecting an enzyme in a sample, said method comprising
a) providing the sample
b) providing a nucleic acid substrate targeted by a said enzymes, c) loading said sample of step a) and said nucleic acid substrate of step b) into a sample chamber comprising a flow through channel, wherein droplets comprising said sample and said nucleic acid substrate are generated,
d) transfer said droplets from said sample chamber to a droplet retaining means through said flow through channel,
e) capturing one or more single droplets in individual cavities of said droplet retaining means, wherein each single droplet is spatially isolated from other droplets, and
e) detecting, in one or more captured droplets, nucleic acid substrate processed by said enzyme, wherein the presence of processed nucleic acid substrate is indicative of the presence of said enzyme.

The enzyme is preferably a DNA-modifying enzyme, such as an enzyme selected from the group consisting of nucleases, ligases, recombinases, topoisomerases and helicases, preferably a type I topoisomerase. Details with respect to the method, such as nucleic acid substrates etc. are provided elsewhere herein.

Method for Identification of Microorganism

A method is provided for the identification of an enzyme-expressing microorganism, preferably a type I topoisomerase-expressing microorganisms in a sample. The microorganism is identified on the basis of a detection of the activity of type I topoisomerase activity of that specific microorganism. In humans and non-human mammals, plants, algae and so forth, the topoisomerase activity of topoisomerases from exogenous microorganisms may be distinguished from the native topoisomerase activity of that particular subject (humans and non-human mammals, plants, algae) based on the substrate used for detection of enzymes activity. The method of the invention comprises the following steps:

i. provision of a sample,
    ii. provision of a nucleic acid substrate targeted by a type I topoisomerase of said microorganism,
    iii. bringing the sample of step i. in contact with the nucleic acid substrate of step ii.
    iv. detecting nucleic acid substrate processed by said type I topoisomerase of said microorganism. The detection of processed nucleic acid substrate is then indicative of the presence of a microorganism, which express that particular topoisomerase. Nucleic acid substrates, which are predominantly target by type I topoisomerases of certain microorganism, is then used for the detection of those specific microorganisms.

Thus, in a broad aspect, the present invention relates to a method of identifying a microorganism in a sample. The method comprises at least the steps of
    i. providing the sample
    ii. providing a double stranded nucleic acid substrate targeted by type I topoisomerase of said microorganism,
    iii. mixing the sample of step i. with the nucleic acid substrate of step ii., and
    iv. detecting nucleic acid substrate targeted by type I topoisomerase of said microorganism,
wherein the presence of nucleic acid substrate targeted by type I topoisomerase of said microorganism is indicative of said microorganism. As described herein below, the microorganism is preferably a pathogenic microorganism, and most preferably a microorganism involved in malaria or tuberculosis, such as *Plasmodium falciparum* or *Mycobacterium tuberculosis*. In a more specific application, the microorganism is identified in a sample from a human subject, and the nucleic acid substrate is then targeted specifically by the microorganism and not by human topoisomerase I.

The method of the present invention allows for detecting the quantitative presence of a microorganism in the sample. Depending on the choice of detection method for detecting processed nucleic acid substrate, the topoisomerase activity may be determined quantitatively. Quantitative detection methods such as rolling circle amplification allow such quantitative detection of topoisomerase activity and thus also quantitative detection of the presence of microorganisms.

The detection of enzymatic activities by the method defined above also allows for the detection in a sample of specific cells or cell types, or microorganisms, which express said enzyme. Therefore, the present invention also relates to a method for the identification of an enzyme-expressing cell, cell type or microorganism in a sample, preferably a DNA-modifying enzyme, such as an enzyme selected from the group consisting of nucleases, ligases, recombinases, topoisomerases and helicases, preferably a type I topoisomerase. In a preferred embodiment, the cell, cell type or microorganism is a type I topoisomerase-expressing cell, cell type or microorganism.

Generally, the cell, cell type or microorganism is identified on the basis of its expression of a DNA modifying enzyme, which is specific for that particular cell type or microorganism, in particular DNA modifying enzymes which display a site-specific DNA modifying activity. In this way, specific nucleic acid substrates are employed, which comprise a sequence specifically targeted by the enzymes in question, where the processing of that substrate is indicative of the presence of that particular cell, cell type or microorganism. The cell, cell type or microorganism is identified on the basis of a detection of an enzymatic activity, such as type I topoisomerase activity, of that specific cell, cell type or microorganism. In humans and non-human mammals, plants, algae and so forth, the enzymatic activity, such as topoisomerase activity, of topoisomerases from exogenous microorganisms can be distinguished from the native enzymatic activity, such as topoisomerase activity, of that particular subject (humans and non-human mammals, plants, algae) based on the substrate used for detection of enzyme activity. The enzymes of the tested subject and the cell, cell type or microorganism can be distinguished by provision of substrates, for which an enzyme, such as type I topoisomerase, of the subject has a higher affinity for relative to the microorganism, and vice versa. The method of identifying a cell, cell type or microorganism of the invention comprises the following steps:

a) providing the sample
b) providing a nucleic acid substrate targeted by an enzyme, such as a type I topoisomerase of said cell, cell type or microorganism,
c) loading said sample of step a) and said nucleic acid substrate of step b) into a sample chamber comprising a flow through channel, wherein droplets comprising said sample and said nucleic acid substrate are generated,
d) transfer said droplets from said sample chamber to a droplet retaining means through said flow through channel,
e) capturing one or more single droplets in individual cavities of said droplet retaining means, wherein each single droplet is spatially isolated from other droplets, and
f) detecting, in one or more captured droplets, nucleic acid substrate processed by said enzyme, such as preferably a type I topoisomerase of said cell, cell type or microorganism, wherein the presence of processed nucleic acid substrate is indicative of the presence of said cell, cell type or microorganism.

The detection of processed nucleic acid substrate is then indicative of the presence of a cell, cell type or microorganism, which express a particular enzyme, such as topoisomerase, that targets the nucleic acid substrate provided in step b). Nucleic acid substrates, which are predominantly target by an enzyme, such as a type I topoisomerase, of one cell, cell type or microorganism, is then used for the detection of that specific microorganism. Examples of nucleic acid substrates, which are specifically targeted and processed by an enzyme, such as a type I topoisomerase, of a specific cell, cell type or microorganism are provided herein below.

As described herein below, the cell, cell type or microorganism is preferably a pathogenic cell, cell type or microorganism, and most preferably a microorganism involved in malaria or tuberculosis, such as *Plasmodium falciparum* or *Mycobacterium tuberculosis*, or *Mycobacterium bovis*. In a more specific application, the microorganism is identified in a sample from a human subject, and the nucleic acid substrate is then targeted predominantly by a type I topoisomerase of the microorganism and not or to a significantly lesser extent by human topoisomerase I. However, the cell or cell type may also be a cancer cell, which express a specific enzymatic activity, such as a specific topoisomerase I activity. In this case, the method of the present invention may be used for diagnosing a cancer, or staging a cancer on the basis of the expression of specific DNA-modifying enzymes, or by the relative activity of DNA-modifying enzymes. The method can be employed for analysing the relative or absolute level of cancer cells in a tumor, which express a certain enzyme or has a certain enzymatic activity.

The method of the present invention allows for detecting the quantitative presence of a cell, cell type or microorganism in the sample. Depending on the choice of detection method for detecting processed nucleic acid substrate, the enzymatic activity, such as topoisomerase activity, may be determined quantitatively. Quantitative detection methods such as rolling circle amplification allow such quantitative detection of enzymatic activity, such as topoisomerase activity, and thus also quantitative detection of the presence of cell, cell type or microorganisms.

Microfluidic System

The present invention relates to methods of detecting an enzyme, such as a DNA-modifying enzyme; methods of identifying a specific cell, cell type or microorganism, such as type I topoisomerase-expressing cell, cell type or microorganism; methods of determining a disease associated with said enzyme, cell, microorganism or cell type; and methods for evaluating the effect of a chemical agent on the enzyme, cell, cell type or microorganism, as described elsewhere herein. A common feature of the methods of the invention is that they are implemented or at least partly implemented in a microfluidic setup.

The sample, which is subjected to analysis by any of the methods of the invention, is loaded into a sample chamber, which comprises at least one flow through channel. In particular, the sample chamber may comprise one or more inlet channels and/or one or more outlet channels. The sample chamber comprises at least one outlet channel, through which small droplets comprising the sample and nucleic acid substrate are transferred. The outlet channel may be formed as a serpentine channel, and serves for the components of the droplet to be adequately mixed. The enzymatic processing of the nucleic acid substrate by the enzyme, such as DNA-modifying enzyme, e.g. type I topoisomerase or recombinase, also preferably take place in the droplets, while travelling in the outlet channel. The microfluidic setup may also be adapted for multiplexing, in which case, the sample chamber comprise two or more outlet channels, where different nucleic acid substrates are loaded in each different outlet channel, thereby allowing several enzymatic activities, cells, cell types or microorganisms to be detected in parallel for the same sample.

The sample chamber also preferably comprises one or more inlet channels, for loading components into the microfluidic system. One inlet channel may direct the loading of a surfactant/carrier fluid/continuous phase, which surrounds the disperse phase/aqueous phase, which exists as droplets, which comprise sample and nucleic acid substrate. That fluid is preferably an oil, such as a fluorocarbon oil although other fluids are available for the same purpose. The sample and nucleic acid substrate thus leaves the sample chamber as water-in oil droplets, wherein the aqueous phase droplets are generated by competitions with the carrier fluid/continuous phase, such as oil, and confined in picoliter droplets in which the processing of the substrate, such as DNA circularization, takes place. Sample, nucleic acid substrate, lysis buffer, and/or processing reaction buffer may be loaded into the sample chamber via one inlet channel or by individual inlet channels. For analysis of biological samples, a cell lysis buffer is preferably mixed with the sample, either prior to loading the sample in the sample chamber of the microfluidic device or loaded into the sample chamber independently of the sample via a designated inlet channel. In a preferred embodiment, the sample chamber of the microfluidic device comprises at least four inlet channels for the individual loading of sample, nucleic acid substrate, cell lysis buffer and oil, respectively.

The dimensions of the sample chamber and flow through channels are within order usually employed in the art. For example, in one embodiment, the one or more flow through channels, inlet channels and/or outlet channels have a diameter of less than 1000 micrometers, such as less than 500 micrometers, for example less than 400, such as less than 300, such as less than 500 micrometers, for example less than 400, such as less than 300, such as less than 200 micrometers, for example less than 100, such as less than 90, such as less than 80 micrometers, for example less than 70, such as less than 60, such as less than 50 micrometers, for example less than 40, such as less than 30, such as less than 25 micrometers, for example less than 20, such as less than 15, such as less than 10 micrometers, for example less than 5 micrometers. In one embodiment, the one or more flow through channels, inlet channels and/or outlet channels have a diameter of 10-50 micrometers, such as 15-45, for example 20-45, for example, 20-40, such as 20-35, such as 20-30, for example 20-25 or 25-30 micrometers, or approximately 25 micrometers in diameter.

The flow rate of the carrier fluid/surfactant and the disperse phase/aqueous phase reagents, such as sample/substrate/lysis buffer may be controlled independently for example by one or more syringe pumps. The independent flow of carrier fluid/surfactant/oil and aqueous reagents allows monodisperse water-in-oil droplets to be formed, for example at a frequency of 0.2-5 kHz, such as 0.3-4, such as 0.4-3, for example 0.5-2.5, such as 0.5-2 kHz, preferably at a frequency of 0.8-1.5 kHz. The droplet volume and generation frequency can be controlled by the flow rate ratio, determined by the competition between continuous phase/carrier fluid/oil and disperse phase (aqueous reagents: cells, lysis buffer and substrates. The continuous phase consisting of for example oil such fluorocarbon oil preferably load at a rate of 1-100 µl (microliter)/min, such as 1-90, for example 1-80, such as 1-90, for example 1-80, such as 1-90, for example 1-80, such as 1-70, for example 1-60, such as 1-50, for example 10-50, such as 10-40, for example 10-30, such as 15-30, for example 15-25 such as 20-25, preferably about 22.5 µl (microliter)/min. The disperse phase/aqueous reagents (such as sample, cells, lysis buffer and/or nucleic acid substrates preferably load at a rate which is significantly lower than the continuous (oil) phase. The disperse phase/aqueous reagents preferably load at a rate of 0.1-50 µl (microliter)/min, such as 0.1-40, for example 0.1-30, such as 0.1-20, for example 0.1-15, such as 0.1-10, for example 0.5-10, such as 0.5-10, for example 1-10, such as 1-15, for example 1-10, such as 1-5, for example 1.5-5, such as 1.5-4, for example 2-3, preferably about 2.5 µl/min.

Thus, the size of the one or more of the flow through channels, in particular the outlet flow through channel, and the flow rate of the components applied via for example the inlet channels in particular the relative flow rate of the disperse phase/aqueous reagents comprising the sample/substrate/lysis buffer and the continuous phase/oil/fluid determine the size of the generated droplets. The size of the droplets is preferably within the picoliter range, such as between 10 and 1000 picoliters, such as 10-500, for example 10-400, for example 10-300, such as 10-200 for example 10-100 picoliters pr droplet. In one embodiment, the droplets have a volume of 500 pL or less, such as between 50 and 200 pL.

Each of the droplets preferably comprises only one cell. However, since the cells are loaded into the sample chamber as a solution of cells, some droplets may comprise more than one cell. Thus, in order to reach a minimum of droplets with more than one cell, the sample should be diluted to such an extent that the majority of droplets comprise 1 cell. Thus, on one embodiment, the sample comprise between approximately 500,000 and 10 million cells per ml, such as between approximately 1 million and 5 million cells per ml. The optimal cell concentration depends on the respective flow rates of the surfactant/continuous phase and the aqueous phase. In a preferred embodiment, the concentration of cells in the sample is adjusted, such that none of the generated droplets comprise 5 or more cells. In one embodiment, at least 90%, such as at least 91%, for example at least 92%, such as at least 93%, such as at least 94%, for example at least 95%, such as at least 96%, such as at least 97%, for example at least 98%, such as at least 99% of the droplets comprise 4 or less cells, such as 3 or less cells, for example 2 or less cells. In a preferred embodiment, at least 50%, such as at least 60%, for example at least 70%, such as at least 75%, for example at least 80%, such as at least 85%, for example at least 90%, such as at least 91%, for example at least 92%, such as at least 93%, such as at least 94%, for example at least 95%, such as at least 96%, such as at least 97%, for example at least 98%, such as at least 99% of the droplets comprise one or no cells. In a preferred embodiment, 60-99%, such as 70-99%, such as 70-95%, such as 75-95, for example 80-90 of the droplets comprise one or no cells. In one embodiment, between approximately 4 and 30% of the droplets comprises one cell, and approximately 0.1 to 10% of the droplets comprise two or more cells. From the sample chamber, droplets are generated and transferred via an outlet flow through channel to a droplet retaining means, where one or more single droplets are captured in individual cavities and each single droplet is spatially isolated from other droplets In the captured droplets, nucleic acid substrate is detected, which have been processed by the enzyme, which is analysed, for example DNA-modifying enzyme, preferably a type I topoisomerase. The presence of processed nucleic acid substrate is then indicative of the presence of said enzyme/enzymatic activity. The droplet retaining means is for example a solid support, which a number comprises individual cavities or pores for retaining individual droplets.

After being captured at the droplet retaining means, the droplets are preferably reduced in size by slight exsiccation. The presence of processed nucleic acid substrate in at least one individual droplet captured on the droplet retaining means can be detected by any suitable method. In a preferred embodiment, processed nucleic acid substrate is detected by rolling circle amplification as described herein below.

Processed nucleic acid substrate can be detected in each droplet, because the substrate is converted from a non-circular molecule, which does not support for example rolling circle amplification, for example a self-folding so-called dumbbell substrate, to a closed nucleic acid circle. That circle may then subsequently be subjected to Rolling Circle Amplification (RCA) leading to a Rolling Circle amplification Product (RCP) consisting of $\sim 10^3$ tandem repeats of a sequence complementary to the DNA circles. Each RCP can be visualised at the single-molecule level in a fluorescence microscope by annealing to fluorescent-labelled probes giving rise to one fluorescent spot for each RCP. Since rolling circle amplification involves no thermal cycling, each RCP represents one closed DNA circle, which in turn represents a single cleavage-ligation event. In a preferred embodiment, the captured droplets are positioned on a glass slide, which is coated with DNA primer, which support amplification of processed, circularized nucleic acid substrate. For example, the means for retaining droplets (drop-trap) may be gently placed on top of a primer-coated glass slide.

The microfluidic setup allows for extremely sensitive and specific detection of enzymatic activities at the level of individual cells. Enzymes, such as type I topoisomerases can be detected at the aM level.

Type I Topoisomerase

By definition enzymes convert substrate molecules to products with changed chemical or physical characteristics without being affected by the process. Hence, at least theoretically one enzyme can create indefinite amounts of product provided with sufficient substrates and, consequently, the most sensitive detection of pathogens imaginable relies on detection of species-specific enzymatic products.

The methods of the invention extends to any enzyme system, such as nucleases, ligases, recombinases, phosphatases, phosphorylases topoisomerases and helicases, preferably type I topoisomerases. Further, nucleic acids modifying enzymes system, where a cascade of enzymes works to modify a nucleic acid target are also within the scope of the present invention. In a preferred embodiment, the present invention relates to nucleic acid-based detection assays based on type I topoisomerase for the identification of a cell, cell type or microorganism via the detection of specific single enzymatic products mediated by topoisomerase I. In general, type I topoisomerases act by introducing single strand cuts in DNA followed by subsequent ligation of the generated nick in a reaction that involves the formation of a covalent enzyme-DNA cleavage intermediate.

According to the methods and uses of the present invention, a microorganism is identified in a sample by detecting a nucleic acid substrate which is targeted by a nucleic acid modifying enzyme system specific for said microorganism. This detection method also forms the basis of the identification and diagnostic methods, compositions and uses of the present invention.

The products, methods and uses of the invention extends to any enzyme system, such as nucleases, phosphatises, phosphorylases, topoisomerases and others. Further, nucleic acids modifying enzymes system, where a cascade of enzymes works to modify a nucleic acid target are also within the scope of the present invention.

In a preferred embodiment, the present invention relates to nucleic acid-based detection assays based on type I topoisomerase for the identification of a microorganism via the detection of specific single enzymatic products mediated by topoisomerase I. In general, type I topoisomerases act by introducing single strand cuts in DNA followed by subsequent ligation of the generated nick in a reaction that involves the formation of a covalent enzyme-DNA cleavage intermediate.

So in a preferred embodiment of the methods and uses of the present invention, a microorganism is identified in a sample by detecting a nucleic acid substrate which is targeted by a type I topoisomerase of said microorganism. Type I topoisomerase targets double stranded nucleic acid molecules by binding a region of said nucleic acid molecule and cleaving a single strand of the duplex.

The cleavage reaction of type I topoisomerase can be conducted on a specific nucleic acid substrate, which upon cleavage is converted from a self-folding so-called dumbbell substrate to a closed nucleic acid circle. That circle may then subsequently be subjected to Rolling Circle Amplification (RCA) leading to a product (RCP) consisting of ~$10^3$ tandem repeats of a sequence complementary to the DNA circles. Each RCP can be visualised at the single-molecule level in a fluorescence microscope by annealing to fluorescent-labelled probes giving rise to one fluorescent spot for each RCP. Since rolling circle amplification involves no thermal cycling, each RCP represents one closed DNA circle, which in turn represents a single cleavage-ligation event.

False positives are avoided by depleting the reaction buffers for divalent cations, which is a prerequisite for the activity of most DNA modifying enzymes, including ligases, but not for type I topoisomerases such as pf-topoisomerase I and tuberculosis topoisomerase I. Thus in a preferred embodiment, the sample is depleted for divalent cations. Thus, an agent for depletion of divalent cations is added to the sample prior to its combination with nucleic acid substrate, or the substrate is mixed with such as agent for depletion of divalent cations in order to reduce the activity of other nuclease/topoisomerase enzymes.

Detection of type I topoisomerase activity is observed by identification of processed nucleic acid substrate. The nucleic acid substrate may be processed by either single strand cleavage and/or ligation. Thus, in one embodiment, the nucleic acid substrate is processed by cleavage, and in another embodiment, the substrate is processed by ligation by a type I topoisomerase of the relevant microorganism. In one embodiment, the substrate is processed by cleavage by the topoisomerase, and then ligated to another nucleic acid molecule or to it self to generate a circular molecule by an exogeneous, such as a recombinant, ligase. So, in one embodiment, ligation is catalyzed by said type I topoisomerase of said microorganism, by a heterogeneous ligase and/or by a recombinant ligase.

In a specific embodiment, the ligation is intramolecular ligation of the 3'-terminus of the nucleic acid substrate to the 5'-terminus of the nucleic acid substrate, thereby generating a circular nucleic acid product. Such a circular product is for example detectable by rolling circle amplification, as described elsewhere herein. In one embodiment, the substrate is processed by cleavage by said type I topoisomerase, followed by intramolecular ligation of the free 3'-terminus of the cleaved substrate to the 5'-terminus of the nucleic acid substrate, thereby generating a circular nucleic acid product.

Kit

The present invention in an important aspect provides a kit for use in the methods of the present invention. The kit thus provides one or more of the means required for conducting the method of identifying a type I topoisomerase-expressing microorganism of the present invention.

Broadly, the present invention relates to a kit comprising at least one nucleic acid substrate targeted by a type I topoisomerase of a microorganism and means for detection of nucleic acid substrate processed by said topoisomerase. The microorganism is preferably associated with a disease. Examples of microorganisms and associated diseases are provided elsewhere herein. In a preferred embodiment, however, the microorganism is selected from the *Plasmodium* genus, for example, the microorganism is *Plasmodium falciparum*, and the associated disease is malaria. In another preferred embodiment, the microorganism is selected from the *Mycobacterium* genus, for example the microorganism is *Mycobacterium tuberculosis*, and the associated disease is tuberculosis, such as human and/or bovine tuberculosis.

The nucleic acid substrate contained in a kit of the present invention is selected from any of the substrates disclosed for use in the method of the invention. The substrate is preferably a double stranded nucleic acid sequence, but the double stranded substrate may be provided in the kit as a single nucleic acid, which folds into a secondary hairpin structure comprising a double-stranded target/substrate region. Generally, nucleic acid substrate is targeted by the specific type I topoisomerase, in that the substrate is processed by cleavage and/or ligation by said type I topoisomerase.

The substrate is for example selected from any one of SEQ ID NO: 5-24. The nucleic acid substrate of the kit, in one embodiment, comprises a sequence selected from any one of SEQ ID NO: 5-24, a sequence at least 30%, 40%, 50%, 60%, 70%, 80%, such as at least 90%, for example at least 91%, 92%, 93%, 94%, 95%, 96%, 97%, 98%, such as at least 99% identical thereto, or a part of at least 5 consecutive nucleotides, such as at least 10, 15, 20, 30, 40, 50, 60, 70, 80, 90, such as at least 100 consecutive nucleotides, of any of said sequences.

In a specific embodiment, the kit comprises a nucleic acid substrate comprising a sequence selected from any one of SEQ ID NO: 8-19, a sequence at least 30%, 40%, 50%, 60%, 70%, 80%, such as at least 90%, for example at least 91%, 92%, 93%, 94%, 95%, 96%, 97%, 98%, such as at least 99% identical thereto, or a part of at least 5 consecutive nucleotides, such as at least 10, 15, 20, 30, 40, 50, 60, 70, 80, 90, such as at least 100 consecutive nucleotides, of any of said sequences. In this case, the microorganism is selected from the *Plasmodium* Genus, for example the microorganism is *Plasmodium falciparum*.

In another embodiment, the kit comprises a nucleic acid substrate comprising the sequence TCTAGTAAG-(N)$_x$-CTTA or ATTTTTCTA-(N)$_x$-TAGA, where N is A, T, C, or G, and x is between 5 and 500 (SEQ ID NOs: 18 or 19). More specifically, the number of nucleotides between the two invariable regions (x) is 5-400, such as 5-300, for example 5-200, such as 10-200, such as 30-150, for example 40-130, such as 50-120, such as 60-100 nucleotides. In another embodiment, the nucleic acid substrate comprises a sequence, with at least 30%, 40%, 50%, 60%, 70%, 80%, such as at least 90%, for example at least 91%, 92%, 93%, 94%, 95%, 96%, 97%, 98%, such as at least 99% identity to any one of SEQ ID NOs: 8-17, while also comprising the sequence TCTAGTAAG-(N)x-CTTA or ATTTTTCTA-(N)x-TAGA, where N is A, T, C, or G, and x is between 5 and 500, such as described above (SEQ ID NOs: 18 or 19).

In yet another embodiment, the kit comprises a nucleic acid substrate comprising a sequence selected from any one of SEQ ID NO: 5-7, a sequence at least 30%, 40%, 50%, 60%, 70%, 80%, such as at least 90%, for example at least 91%, 92%, 93%, 94%, 95%, 96%, 97%, 98%, such as at least 99% identical thereto, or a part of at least 5 consecutive nucleotides, such as at least 10, 15, 20, 30, 40, 50, 60, 70, 80, 90, such as at least 100 consecutive nucleotides, of any of said sequences. In this case, the microorganism is selected from the *Mycobacterium* genus, for example the microorganism is *Mycobacterium tuberculosis*.

More specifically, the kit may comprise a nucleic acid substrate comprising SEQ ID NO: 7, and in one embodiment, the kit comprises a nucleic acid substrate comprising a sequence, with at least 30%, 40%, 50%, 60%, 70%, 80%, such as at least 90%, for example at least 91%, 92%, 93%, 94%, 95%, 96%, 97%, 98%, such as at least 99% identity to any one of SEQ ID NO: 5 and 6, while also comprising SEQ ID NO: 7.

The kit provides one or more means for detecting the catalytic activity of type I topoisomerase of the specific microorganism, and one catalytic activity of type I topoisomerase is cleavage of double stranded nucleic acid substrate, which is provided in the kit. The kit, however, in one embodiment further comprise a ligase, which can be used for religating a substrate processed by cleavage by type I topoisomerase.

The kit may further comprise any suitable means for detection of substrate processed by a type I topoisomerase. Non-limiting examples of such means are means for southern blotting, polymerase chain reaction, RT-PCR, qPCR, RFLD, primer extension, DNA array technology, isothermal amplification, and/or rolling circle amplification. In a preferred embodiment, the kit comprises means for rolling circle amplification. Thus, the kit for example, in one embodiment comprises at least one oligonucleotide primer, which is capable of hybridizing to a processed substrate. The at least one oligonucleotide primer may span the processed nucleotide position of the processed nucleic acid substrate, thereby only supporting amplification of processed substrates. For more convenient manipulation and detection, the at least one oligonucleotide primer is in a preferred embodiment coupled to a magnetic bead. In further embodiments, the kit may comprise a nucleic acid polymerase and/or nucleotides, for use in amplification of a processed substrate.

The kit may be presented in any appropriate physical form, which allows for easy use thereof. In a preferred embodiment, the kit is provided, wherein the at least one nucleic acid substrate, oligonucleotide primer, nucleic acid polymerase and/or nucleotide is immobilized on a solid support. Thus, the kit is in a preferred embodiment provided as a lateral flow test strip and/or a dipstick. The lateral flow test may be provided in a dipstick format. Lateral flow tests are simple devices for detecting the presence (or absence) of a target analyte in sample, which in the present invention is a processed nucleic acid substrate, of more notably, a rolling circle amplification product generated on the basis thereof. In the lateral flows test, the test sample flows along a solid substrate, preferably via capillary action. After the sample is applied to the test it first encounters one or more nucleic acid substrate immobilized on the test strip. The substrate is here targeted by type I topoisomerase, and processed by cleavage and/or ligation. Then, the processed substrate flows or is actively transferred to encounter nucleotides and polymerase, such as phi polymerase, and a primer, which promotes the polymerisation of the primer using the processed substrate as template, which is preferably circularized by intramolecular ligation. The amplification product, such as rolling circle amplification product, is then visualized for example by a coloured agent, which is indicative of the processed substrate or amplification product. Depending on the design of the lateral flow test strip, the coloured reagent or agent can be bound at the test line or zone in the test strip.

Thus, in one embodiment, the nucleotides comprised in the kit of the invention comprise one or more detectable labels, such as a fluorophore. In another embodiment, the kit further comprise at least one nucleic acid probe capable of hybridizing to the nucleic acid substrate, the processed nucleic acid substrate and/or the nucleic acid amplification product. In a specific example, the probe comprises a sequence according to SEQ ID NO: 20-22, or a sequence at least 30%, 40%, 50%, 60%, 70%, 80%, such as at least 90%, for example at least 91%, 92%, 93%, 94%, 95%, 96%, 97%, 98%, such as at least 99% identical thereto, or a part of at least 5 consecutive nucleotides, such as at least 6, 7, 8, 9, 10, 11, 12, 13, 14, 15, 16, 17, 18, 19, 20, 30, 40, 50, such as at least 60 consecutive nucleotides, of any of said sequences. The nucleic acid probe, preferably comprise at least one detectable label. For example, the probe is labelled with one or more enzymes, fluorescent dyes, radioactive nucleotides and/or biotinylated nucleotides. In a preferred embodiment, the probe is coupled to an enzyme, such as an enzyme, which is capable of converting a substrate into a detectable product. The enzyme is for example fused with streptavidin, thereby enabling it to be coupled via biotin. Thus in a preferred embodiment of the kit, the enzyme is fused with streptavidin, and coupled to the nucleic acid probe via interaction with said biotinylated nucleotides incorporated in the nucleic acid probe. The enzyme is any enzyme with an easily detectable activity. In one example, the enzyme is horse-radish peroxidase. In this case, the kit may further comprise TMB (3,3',5,5'-Tetramethylbenzidine) or functional equivalents thereof as a substrate for the enzyme. In the case of other enzymes included in the kit, the kit may also further comprise any suitable substrate for the respective enzyme.

The present invention also provides kits for multiplexed analysis, wherein two or more microorganisms are detected in parallel or simultaneously. Such kits comprise a plurality of nucleic acid substrates each targeted by type I topoisomerases of different microorganisms.

In an important embodiment, the kit is provided with a positive and/or a negative control for the verification of substrate function, enzyme activity etc. In one such embodiment, the kit comprises a circular nucleic acid, an oligonucleotide primer capable of hybridizing to said circular nucleic acid and/or a nucleic acid probe capable of hybridizing to said nucleic acid substrate as a positive control of the means for detection. In another embodiment, the kit either separately or in addition as positive control further comprises a nucleic acid substrate for a human type I topoisomerase, an oligonucleotide primer capable of hybridizing to said nucleic acid substrate and/or a nucleic acid probe capable of hybridizing to said nucleic acid substrate. In this way, a human type I topoisomerase may be detected in parallel with the detection of a type I topoisomerase of a pathogenic microorganism.

The kit may comprise separate chambers for the different reaction or steps of the detection method. The kit may for example comprise a separate processing chamber, comprising the nucleic acid substrate, and amplification chamber comprising polymerase and/or nucleotides, and a detection chamber comprising means for detection of amplification product, for example horse radish peroxidase and/or TMB. The kit may comprise further chambers, or the chambers may be merged into fewer chambers. For example, in one embodiment, the kit comprises a separate reaction chamber, comprising nucleic acid substrate, polymerase and/or nucleotides, and a detection chamber.

A kit comprising separate chambers for different reactions may further comprise means for transferring the oligonucleotide primers from the reaction to the detection chamber. In one embodiment, the kit comprises a magnet for transferring the oligonucleotide primers. In such a kit, the oligonucleotide primers are preferably coupled to magnetic beads, thereby allowing the use of the included magnet for transferring oligonucleotide primers and/or rolling circle amplification product from one compartment, such as a reaction chamber or amplification chamber to a detection chamber.

In a preferred embodiment, the kit comprises an agent for depletion of divalent cations, for example a chelating agent, such as EDTA, or any other effective agent.

Nucleic Acid Substrate

The methods and kits of the present invention employ or comprise nucleic acid substrates, which are targeted by type I topoisomerase of a microorganisms, the presence of which is to be determined by the method of the invention. The sequence and structure of the nucleic acid substrate is optimized with respect to the specific topoisomerase activity of the respective microorganism. Specific target sequences are targeted with higher efficiency by topoisomerase of certain organisms than others, and in this way, the activity of microorganisms, such as pathogenic and/or parasitic microorganisms can be distinguished from human and non-human mammal topoisomerases.

So in the methods and kits of the present invention, the nucleic acid substrate is predominantly targeted by type I topoisomerase of said microorganism and to a lesser extent by any type I topoisomerase native to said sample. The term "native" as used here, indicates that the topoisomerase is the natural topoisomerase, which is encoded by the cells of the sample, i.e. human cells if the sample originates from a human being, and bovine cells, if the sample originates from a bovine subject. Thus, a type I topoisomerase native to a human sample is a human type I topoisomerase and a type I topoisomerase native to a bovine sample is a bovine type I topoisomerase.

The nucleic acid substrate may be labelled, and/or hybridized to one or more nucleic acid probes, and detected via the respective label. The nucleic acid substrates may be coupled to a support. Such supports are well known to those of ordinary skill in the art and include, but are not limited to glass, plastic, metal, or latex. In particular aspects of the invention, the support can be planar or in the form of a bead or other geometric shapes or configurations known in the art.

In the methods and/or kits of the invention, nucleic acid substrate is a double stranded nucleic acid molecule. The double stranded substrate is for example provided at two single molecules, which are hybridized, however, in a preferred embodiment, the double stranded substrate is provided as a single nucleic acid, which folds into a secondary hairpin structure comprising a double-stranded target region.

The nucleic acid substrate of the methods and/or kits of the present invention is for example selected from any one of SEQ ID NO: 5-24. The nucleic acid substrate, in one embodiment, comprises a sequence selected from any one of SEQ ID NO: 5-24, a sequence at least 30%, 40%, 50%, 60%, 70%, 80%, such as at least 90%, for example at least 91%, 92%, 93%, 94%, 95%, 96%, 97%, 98%, such as at least 99% identical thereto, or a part of at least 5 consecutive nucleotides, such as at least 10, 15, 20, 30, 40, 50, 60, 70, 80, 90, such as at least 100 consecutive nucleotides, of any of said sequences.

In a specific embodiment, the method and/or kit comprises a nucleic acid substrate comprising a sequence selected from any one of SEQ ID NO: 8-19, a sequence at least 30%, 40%, 50%, 60%, 70%, 80%, such as at least 90%, for example at least 91%, 92%, 93%, 94%, 95%, 96%, 97%, 98%, such as at least 99% identical thereto, or a part of at least 5 consecutive nucleotides, such as at least 10, 15, 20, 30, 40, 50, 60, 70, 80, 90, such as at least 100 consecutive nucleotides, of any of said sequences. In this case, the microorganism is selected from the *Plasmodium* Genus, for example the microorganism is *Plasmodium falciparum*.

In another embodiment, the method and/or kit comprises a nucleic acid substrate comprising the sequence TCTAG-TAAG-$(N)_x$-CTTA or ATTTTTCTA-$(N)_x$-TAGA, where N is A, T, C, or G, and x is between 5 and 500 (SEQ ID NOs: 18 or 19). More specifically, the number of nucleotides between the two invariable regions (x) is 5-400, such as 5-300, for example 5-200, such as 10-200, such as 30-150, for example 40-130, such as 50-120, such as 60-100 nucleotides. In another embodiment, the nucleic acid substrate comprises a sequence, with at least 30%, 40%, 50%, 60%, 70%, 80%, such as at least 90%, for example at least 91%, 92%, 93%, 94%, 95%, 96%, 97%, 98%, such as at least 99% identity to any one of SEQ ID NOs: 8-17, while also comprising the sequence TCTAGTAAG-(N)x-CTTA or ATTTTTCTA-(N)x-TAGA, where N is A, T, C, or G, and x is between 5 and 500, such as described above (SEQ ID NOs: 18 or 19). However, the number of nucleotides between the two non-variable regions may also be over 500, however, this is less preferred, because the size of the substrate might reduce the efficiency of detection of processed substrate. Importantly, substrates of this type preferably folds into a double stranded structure by forming a hairpin structure, where the two non-variable regions forms base pairs over a certain region, cf. for example FIGS. 1 and 11. Thus, in a preferred embodiment, the nucleotides in the region defined as (N)x form a hairpin structure, i.e. stemloop intramolecular base pairing, wherein at least 5, but more preferably at least 10, such as at least 15, or at least 20 consecutive nucleotides form intramolecular base pairing with complementary nucleotides of the same nucleic acid molecule.

In yet another embodiment, the method and/or kit comprises a nucleic acid substrate comprising a sequence selected from any one of SEQ ID NO: 5-7, a sequence at least 30%, 40%, 50%, 60%, 70%, 80%, such as at least 90%, for example at least 91%, 92%, 93%, 94%, 95%, 96%, 97%, 98%, such as at least 99% identical thereto, or a part of at least 5 consecutive nucleotides, such as at least 10, 15, 20, 30, 40, 50, 60, 70, 80, 90, such as at least 100 consecutive nucleotides, of any of said sequences. In this case, the microorganism is selected from the *Mycobacterium* genus, for example the microorganism is *Mycobacterium tuberculosis*.

More specifically, the method and/or kit may comprise a nucleic acid substrate comprising SEQ ID NO: 7, and in one embodiment, the method and/or kit comprises a nucleic acid substrate comprising a sequence, with at least 30%, 40%, 50%, 60%, 70%, 80%, such as at least 90%, for example at least 91%, 92%, 93%, 94%, 95%, 96%, 97%, 98%, such as at least 99% identity to any one of SEQ ID NO: 5 and 6, while also comprising SEQ ID NO: 7.

Sample

A "sample" according to the present invention is any suitable biological or non-biological sample. The biological sample is in a preferred embodiment, isolated from a subject, such as a human being. The choice of sample depends on the specific microorganism or infectious disorder to be determined as well as the detection method, and will be appreciated by those of skill in the art. In one embodiment the sample is a blood sample, a tissue sample, a secretion sample, semen, ovum, hairs, nails, tears, urine or faeces. A convenient sample type is a blood sample. The blood sample includes any fraction of blood, such as blood plasma or blood serum, sputum, urine, cell smear.

However, the sample of the invention may also be a tissue sample, such as a sample of a tissue selected from the group consisting of skin, epidermis, dermis, hypodermis, breast, fat, thymus, gut, small intestine, large intestine, stomach, muscle, pancreas, heart muscle, skeletal muscle, smooth muscle, liver, lung, brain, cornea and tumours, ovarian tissue, uterine tissue, colon tissue, prostate tissue, lung tissue, renal tissue, thymus tissue, testis tissue, hematopoietic tissue, bone marrow, urogenital tissue, expiration air, stem cells, including cancer stem cells, biopsies, and cerebrospinal fluid. In one embodiment, the sample is blood plasma, blood serum, sputum, urine, cell smear, faeces, cerebrospinal fluid, or a biopsy.

The sample may originate from any source, which is of interest for detection of microorganisms. In non-limiting examples, the sample is a sample originating or obtained from a ruminant, a ferret, a badger, a rodent, an elephant, a bird, a pig, a deer, a coyote, a camel, a puma, a fish, a dog, a cat, a non-human primate or a human. In a preferred embodiment, the sample is originating or obtained from a human being; i.e. the sample is a human sample. In another embodiment, the sample is originating or obtained from a non-human animal; i.e. the sample is a non-human animal sample. In one preferred embodiment, the sample is originating or obtained from a bovine subject; i.e. the sample is a bovine sample.

However, in another important application of the methods and kits of the present invention, the sample is obtained from any source of human or animal consumption, such as food or feed; i.e. the sample is a food or feed sample. In another embodiment, the sample is water, such as drinking water and domestic water.

Microorganism

As explained herein above, the present invention relates to a method of identifying a type I topoisomerase-expressing microorganism in a sample, as well as a method of determining a disease in a subject based on identifying a microorganism in a sample, and a kit comprising a nucleic acid substrate targeted by a type I topoisomerase of a microorganism. A microorganism of the present invention encompasses any pathogenic and/or parasitic agent, so for example the microorganism is a pathogenic microorganism, and in another example, the microorganism is a parasitic microorganism. The microorganism is for example a virus, a bacteria, a protozoa, a fungus, a mould, an amoeba or a parasitic worm.

The present invention relates to a method for identifying a microorganism as well as methods and compounds for treating an infectious disorder, which is caused by a microorganism. The invention also provides kits for use in such methods, where the kits comprise at least one nucleic acid substrate targeted by a type I topoisomerase of a microorganism and means for detection of nucleic acid substrate processed by said topoisomerase.

The microorganism of the invention is thus, mostly, a pathogenic microorganism.

Microorganism includes bacteria and viruses.

The microorganism identified by the method of the present invention is for example involved in and/or is the causative agent in one or more infectious disorders. The microorganism is for example involved in tuberculosis, malaria, toxoplasmosis or Lyme disease/borreliosis (*Borrelia*).

In one embodiment, the microorganism is *Plasmodium falciparum*, or *Mycobacterium tuberculosis*, enterobacteria, enterococci, corynebacteria, *Salmonella* spp, *Mycobacterium avium* sp. *paratuberculosis*, *Brachyspira hyodysenteriae*, *Lawsonia intracellularis*, *campylobacter* spp., *clostridia*, *coronavirus*, *rotavirus*, *torovirus*, *calicivirus*, *astrovirus*, *canine parvovirus*, *coccidia* and *cryptosporidia*, *E. coli*, *Salmonella* spp, *Yersinia* spp., including *Yersinia enterocolitica*, *Mycobacterium avium* ssp. *paratuberculosis*, *Coxiella burnetti*, rotavirus, coronavirus, calicivirus, bovine virus diarrhoea virus, bovine herpes virus, rinderpest virus, *coccidia*, and *cryptosporidia*, *Salmonella* spp, *Lawsonia*

*intracellularis*, *Campylobacter* spp, Enteropathogenic *E. coli*, *Brachyspira* spp including *Brachyspira hyodysenteria*, *Clostridium* spp, rotavirus, sappovirus, norovirus, and coronavirus, *Salmonella* spp, *Camphylobacter* spp., Norovirus, rotavirus, *Vibrio* spp. including *Vibrio cholera*, *Shigella* spp., *Helicobacter* spp., *coccidia* or *cryptosporidia*.

If the microorganism is a bacterium, the microorganism is selected from Eubacteria, or is selected from Actinobacteria, or is selected from Actinomycetes, or is selected from Corynebacterineae, or is selected from Mycobacteriaceae, or is selected from Mycobacteria. In one embodiment, the microorganism is selected from the *Mycobacterium* Genus, and a more specific embodiment, the microorganism is *Mycobacterium tuberculosis* or *Mycobacterium bovis*

In one embodiment, the microorganism of the methods and kits of the present invention is selected from Eukaryotes, or is selected from Alveolates, or is selected from Apicomplexans/sporozoans, or is selected from Haematozoans, or is selected from Haemosporidians, or is selected from Plasmodiidans, or is selected from *Plasmodium*.

In a preferred embodiment, the microorganism belongs to the *Plasmodium* genus. The microorganism is for example selected from the following species: *Plasmodium clelandi*, *Plasmodium draconis*, *Plasmodium lionatum*, *Plasmodium saurocordatum*, *Plasmodium vastator*, *Plasmodium juxtanucleare*, *Plasmodium basilisci*, *Plasmodium clelandi*, *Plasmodium lygosomae*, *Plasmodium mabuiae*, *Plasmodium minasense*, *Plasmodium rhadinurum*, *Plasmodium volans*, *Plasmodium anasum*, *Plasmodium circumflexum*, *Plasmodium dissanaikei*, *Plasmodium durae*, *Plasmodium fallax*, *Plasmodium formosanum*, *Plasmodium gabaldoni*, *Plasmodium garnhami*, *Plasmodium gundersi*, *Plasmodium hegneri*, *Plasmodium lophurae*, *Plasmodium pedioecetii*, *Plasmodium pinnotti*, *Plasmodium polare*, *Plasmodium cathemerium*, *Plasmodium coggeshalli*, *Plasmodium coturnixi*, *Plasmodium elongatum*, *Plasmodium gallinaceum*, *Plasmodium giovannolai*, *Plasmodium lutzi*, *Plasmodium matutinum*, *Plasmodium paddae*, *Plasmodium parvulum*, *Plasmodium relictum*, *Plasmodium tejera*, *Plasmodium elongatum*, *Plasmodium hermani*, *Plasmodium floridense*, *Plasmodium tropiduri*, *Plasmodium billbrayi*, *Plasmodium billcollinsi*, *Plasmodium falciparum*, *Plasmodium gaboni*, *Plasmodium reichenowi*, *Plasmodium pessoai*, *Plasmodium tomodoni*, *Plasmodium wenyoni*, *Plasmodium ashfordi*, *Plasmodium bertii*, *Plasmodium bambusicolai*, *Plasmodium columbae*, *Plasmodium corradettii*, *Plasmodium dissanaikei*, *Plasmodium globularis*, *Plasmodium hexamerium*, *Plasmodium jiangi*, *Plasmodium kempi*, *Plasmodium lucens*, *Plasmodium megaglobularis*, *Plasmodium multivacuolaris*, *Plasmodium nucleophilum*, *Plasmodium papernai*, *Plasmodium parahexamerium*, *Plasmodium paranucleophilum*, *Plasmodium rouxi*, *Plasmodium vaughani*, *Plasmodium dominicum*, *Plasmodium chiricahuae*, *Plasmodium mexicanum*, *Plasmodium pifanoi*, *Plasmodium bouillize*, *Plasmodium brasilianum*, *Plasmodium cercopitheci*, *Plasmodium coatneyi*, *Plasmodium cynomolgi*, *Plasmodium eylesi*, *Plasmodium fieldi*, *Plasmodium fragile*, *Plasmodium georgesi*, *Plasmodium girardi*, *Plasmodium gonderi*, *Plasmodium gora*, *Plasmodium gorb*, *Plasmodium inui*, *Plasmodium jefferyi*, *Plasmodium joyeuxi*, *Plasmodium knowlei*, *Plasmodium hyobati*, *Plasmodium malariae*, *Plasmodium ovale*, *Plasmodium petersi*, *Plasmodium pitheci*, *Plasmodium rhodiani*, *Plasmodium schweitzi*, *Plasmodium semiovale*, *Plasmodium semnopitheci*, *Plasmodium silvaticum*, *Plasmodium simium*, *Plasmodium vivax*, *Plasmodium youngi*, *Plasmodium achiotense*, *Plasmodium adunyinkai*, *Plasmodium aeuminatum*, *Plasmodium agamae*, *Plasmodium balli*, *Plasmodium beltrani*, *Plasmodium brumpti*, *Plasmodium cnemidophori*, *Plasmodium diploglossi*, *Plasmodium giganteum*, *Plasmodium heischi*, *Plasmodium josephinae*, *Plasmodium pelaezi*, *Plasmodium zonuriae*, *Plasmodium achromaticum*, *Plasmodium aegyptensis*, *Plasmodium anomaluri*, *Plasmodium atheruri*, *Plasmodium berghei*, *Plasmodium booliati*, *Plasmodium brodeni*, *Plasmodium bubalis*, *Plasmodium bucki*, *Plasmodium caprae*, *Plasmodium cephalophi*, *Plasmodium chabaudi*, *Plasmodium coulangesi*, *Plasmodium cyclopsi*, *Plasmodium foleyi*, *Plasmodium girardi*, *Plasmodium incertae*, *Plasmodium inopinatum*, *Plasmodium landauae*, *Plasmodium lemuris*, *Plasmodium melanipherum*, *Plasmodium narayani*, *Plasmodium odocoilei*, *Plasmodium percygarnhami*, *Plasmodium pulmophilium*, *Plasmodium sandoshami*, *Plasmodium traguli*, *Plasmodium tyrio*, *Plasmodium uilenbergi*, *Plasmodium vinckei*, *Plasmodium watteni* and *Plasmodium yoelli*.

Most preferred, the microorganism is *Plasmodium falciparum*, which is a causative agent of human Malaria.

In another preferred embodiment, the microorganism belongs to the *Mycobacterium* genus. The microorganism is for example selected from the *Mycobacterium tuberculosis* complex (MTBC), the members of which are causative agents of human and animal tuberculosis.

Species in this complex include: *M. tuberculosis*, *M. bovis*, *M. bovis* BCG, *M. africanum*, *M. canetti*, *M. caprae*, *M. microti*, and *M. pinnipedii*. Most preferably, the microorganism is *Mycobacterium tuberculosis*, which is the major cause of human tuberculosis.

Detection

According to the methods and uses of the present invention, a microorganism is identified in a sample by detecting a nucleic acid substrate which is targeted by a type I topoisomerase of said microorganism. As described above, type I topoisomerase targets double stranded nucleic acid molecules by binding a region of said nucleic acid molecule and cleaving a single strand of the duplex. A nucleic acid substrate, which has been targeted by type I topoisomerase may thus be detected by identifying those nucleic acid substrates in the sample that have been cleaved. The nucleic acid substrate is thus, preferably targeted by a topoisomerase I of the microorgansms only, and not by other topoisomerase I-activities of the sample, such as native topoisomerases of the subject tested for microorganisms or infectious disorders such as malaria and/or tuberculosis.

Detection of cleaved and uncleaved (targeted and untargeted) nucleic acid substrates may be performed by any suitable method available. Detection is for example obtained by southern blotting, polymerase chain reaction, RT-PCR, qPCR, RFLD, primer extension, DNA array technology, a linear amplification technique, isothermal amplification, and/or rolling circle amplification. In a preferred embodiment, the nucleic acid substrate is detected by rolling circle amplification, for example by a method as described in WO 2008/148392.

Processed nucleic acid substrate is in a preferred embodiment detected by rolling circle amplification performed by
  i. providing at least one oligonucleotide primer, which is capable of hybridizing to circularized nucleic acid substrate,
  ii. hybridizing the at least one oligonucleotide primer to the circularized nucleic acid substrate,
  iii. providing a nucleic acid polymerase and nucleotides
  iv. generating a rolling circle amplification product by extending the at least one oligonucleotide primer using the circularized nucleic acid substrate as template, and
  v. detecting the rolling circle amplification product.

In certain aspects, a detection assay can be a quantitative amplification assay, such as quantitative PCR (qPCT) or quantitative RT-PCR (qRT-PCR). Other methods include hybridization assays, such as array hybridization assays or solution hybridization assays. The nucleic acid substrate may be labelled, and/or hybridized to one or more nucleic acid probes, and detected via the respective label.

In a convenient setup of the detection methods of the present invention, a simple portable readout devices or even with colorimetric readout visible for the naked eye, adapting the biosensor for at-place-of-care diagnosis suitable even for the special requirements of third world countries currently suffering the major burden of malaria epidemics.

Primers and Probes

Detection of nucleic acid substrate both processed and non-processed substrates may be obtained by use of different tailored primers and probes, preferably oligonucleotide primers and/or probes. The primers and probes should be able to bind to the nucleic acid substrate either directly or indirectly. The sequence of the oligonucleotide primers and probes should of course be complementary to the substrate sequence and the general design of such oligonucleotide primers and probes are well known to those of skill in the art. Oligonucleotide primers and probes of any suitable lengths are within the scope of the invention, for example oligonucleotides of 5-300 nucleotides, such as 10-200, 20-100, or 20-50 consecutive nucleotides.

In the present invention, primers are primarily used for polymerisation/extension catalysed by a polymerase, preferably a DNA polymerase, such as phi polymerase, or any other suitable polymerase, where the primers hybridize to the nucleic acid substrate of the invention. Thus, the primers of the methods and kits of the present invention are preferably capable of hybridizing to a processed substrate. However, primers hybridizing to unprocessed substrate may also be employed, for example in positive control reactions. The primer may span the processed nucleotide position of the processed nucleic acid substrate, thereby only supporting amplification of processed substrates. However, the primers may also be designed to hybridize to other positions of the nucleic acid substrate, since in certain embodiments, targeted nucleic acid substrate is circularized by topoisomerase processing, thereby serving as a template for rolling circle amplification using a primer, which hybridize anywhere in the substrate sequence. For this reason, oligonucleotide primers hybridizing anywhere in the nucleic acid substrate are within the scope of the present invention.

For more convenient manipulation and detection, the at least one oligonucleotide primer is in a preferred embodiment coupled to a magnetic bead. In this case, primers and/or amplification product may be transferred or otherwise manipulated using magnets/magnetic fields. The methods and kits of the invention may thus comprise primers and/or probes coupled to magnetic beads and/or magnets/magnetic fields. In further embodiments, the methods and/or kits may comprise a nucleic acid polymerase and/or nucleotides, for use in amplification of a processed substrate.

In one embodiment, the oligonucleotide primer or probe of the methods and/or kits comprise a sequence of at least 5 consecutive complementary nucleotides, such as at least 10, 15, 20, 30, 40, 50, 60, 70, 80, 90, such as at least 100 consecutive complementary nucleotides selected from any region of any of SEQ ID NO: 5-24, and/or any sequence at least 30%, 40%, 50%, 60%, 70%, 80%, such as at least 90%, for example at least 91%, 92%, 93%, 94%, 95%, 96%, 97%, 98%, such as at least 99% identical thereto.

In one embodiment, the oligonucleotide primer or probe of the methods and/or kits is SEQ ID NO: 20, 21, 22, 23, or 24. For example, the oligonucleotide primer of kits or methods of the present invention is SEQ ID NO: 23 or 24, and the oligonucleotide probe of kits or methods of the present invention is SEQ ID NO: 20, 21, or 22.

In a specific example, the probe of the methods and/or kits of the present invention comprises a sequence according to SEQ ID NOs: 20-22, or a sequence at least 30%, 40%, 50%, 60%, 70%, 80%, such as at least 90%, for example at least 91%, 92%, 93%, 94%, 95%, 96%, 97%, 98%, such as at least 99% identical thereto, or a part of at least 5 consecutive nucleotides, such as at least 6, 7, 8, 9, 10, 11, 12, 13, 14, 15, 16, 17, 18, 19, 20, 30, 40, 50, such as at least 60 consecutive nucleotides, of any of said sequences.

In a user friendly set up of the methods and kits of the present invention, nucleic acid substrate, oligonucleotide primer, oligonucleotide probe, nucleic acid polymerase and/or nucleotides is immobilized on a solid support. With the oligonucleotide primer immobilized on a solid support, an amplification product, such as a rolling circle amplification product, is confined to a specific location, which allows the product to be manipulated, transferred and/or detected by washing and probe hybridization, cf. FIGS. 1C, 4B, 10, 12, 13 and 14.

The choice of solid support depends on the specific approach of the methods and kits of the invention and a range of possible solutions are available to those of skill in the art. The solid support is for example a glass surface, or a magnetic bead. In one embodiment, the nucleic acid substrate, oligonucleotide primer, oligonucleotide probe, nucleic acid polymerase and/or nucleotides is immobilized on a lateral flow test strip and/or a dipstick, cf. herein above. In particular, the oligonucleotide primer of the methods and kits of the present invention is immobilized on such a dipstick/lateral flow test.

For more convenient manipulation and detection, the at least one oligonucleotide primer is in one embodiment coupled to a magnetic bead. In this case, primers and/or amplification product may be transferred or otherwise manipulated using magnets/magnetic fields. The methods and kits of the invention may thus comprise primers and/or probes coupled to magnetic beads and/or magnets/magnetic fields. In further embodiments, the methods and/or kits may comprise a nucleic acid polymerase and/or nucleotides, for use in amplification of a processed substrate.

In another preferred embodiment, the primers are coated on a glass slide, which is contacted with the retained droplets, which comprise processed and/or non-processed substrate.

In one embodiment, the oligonucleotide primer or probe of the methods and/or kits comprise a sequence of at least 5 consecutive complementary nucleotides, such as at least 10, 15, 20, 30, 40, 50, 60, 70, 80, 90, such as at least 100 consecutive complementary nucleotides selected from any region of any of SEQ ID NO: 5-32, and/or any sequence at least 30%, 40%, 50%, 60%, 70%, 80%, such as at least 90%, for example at least 91%, 92%, 93%, 94%, 95%, 96%, 97%, 98%, such as at least 99% identical thereto. In one embodiment, the oligonucleotide primer or probe of the methods and/or kits is SEQ ID NO: 20, 21, 22, 23, 24, or 27-32. For example, the oligonucleotide primer of kits or methods of the present invention is SEQ ID NO: 23 or 24, and the oligonucleotide probe of kits or methods of the present invention is SEQ ID NO: 20, 21, or 22.

In a specific example, the probe of the methods and/or kits of the present invention comprises a sequence according to SEQ ID NO: 20-22, or a sequence at least 30%, 40%, 50%, 60%, 70%, 80%, such as at least 90%, for example at least 91%, 92%, 93%, 94%, 95%, 96%, 97%, 98%, such as at least 99% identical thereto, or a part of at least 5 consecutive nucleotides, such as at least 6, 7, 8, 9, 10, 11, 12, 13, 14, 15, 16, 17, 18, 19, 20, 30, 40, 50, such as at least 60 consecutive nucleotides, of any of said sequences. In a user friendly set up of the methods and kits of the present invention, nucleic acid substrate, oligonucleotide primer, oligonucleotide probe, nucleic acid polymerase and/or nucleotides is immobilized on a solid support. With the oligonucleotide primer immobilized on a solid support, an amplification product, such as a rolling circle amplification product, is confined to a specific location, which allows the product to be manipulated, transferred and/or detected by washing and probe hybridization, cf. FIGS. 1C, 4B, 10, 12, 13, 14, 21 and 26.

The choice of solid support depends on the specific approach of the methods and kits of the invention and a range of possible solutions are available to those of skill in the art. The solid support is for example a glass surface, or a magnetic bead. In one embodiment, the nucleic acid substrate, oligonucleotide primer, oligonucleotide probe, nucleic acid polymerase and/or nucleotides is immobilized on a glass slide. In particular, the oligonucleotide primer of the methods and kits of the present invention is immobilized on such a glass slide.

Detection and Visualization

The processed nucleic acid substrate is then detected, for example by detection of an amplification product generated on the basis of processed topoisomerase substrate, such as rolling circle amplification product. Detection is preferably performed by observation of a visual signal, while radioactive signals could also be employed, which can also be visualized by radioautography. The processed substrate may for example be detected by visualizing a rolling circle amplification product. Thus, any suitable coloring agent may be employed for this purpose.

In one embodiment, the nucleotides comprised in the kit of the invention or used in the method comprise one or more detectable labels, such as a fluorophore and/or radioactively labelled nucleotides. In this case, the rolling circle amplification product is detected via its incorporation of such nucleotides comprising one or more detectable labels.

In another embodiment, detection is obtained by use of at least one nucleic acid probe capable of hybridizing to the nucleic acid substrate, the processed nucleic acid substrate and/or the nucleic acid amplification product. In this case, the processed nucleic acid substrate or amplification product, such as rolling circle amplification product, is detected by hybridization of a labelled nucleic acid probe to one or multiple sites of the processed nucleic acid substrate or amplification product, such as the rolling circle amplification product. The probe is for example labelled with one or more fluorescent dyes, radioactive nucleotides and/or biotinylated nucleotides. The nucleic acid probe, preferably comprise at least one detectable label. For example, the probe is labelled with one or more enzymes, fluorescent dyes, radioactive nucleotides and/or biotinylated nucleotides. In a preferred embodiment, the probe is coupled to an enzyme, such as an enzyme, which is capable of converting a substrate into a detectable product. The enzyme is for example fused with streptavidin, thereby enabling it to be coupled via biotin. Thus in a preferred embodiment of the methods and kits, the enzyme is fused with streptavidin, and coupled to the nucleic acid probe via interaction with said biotinylated nucleotides incorporated in the nucleic acid probe. The enzyme is any enzyme with an easily detectable activity. In one example, the enzyme is horse-radish peroxidase. In this case, the method and/or kit may further comprise TMB (3,3',5,5'-Tetramethylbenzidine) or functional equivalents thereof as a substrate for the enzyme. In the case of other enzymes included in the kit or employed in the method of the invention, the kit or method may also further comprise/employ any suitable substrate for the respective enzyme.

Specific Applications

The technology of the methods and kits of the present invention may be employed for identifying any microorganism and/or any infection in any subject, including humans, non-human animals, such as house-hold stocks, and plants, as described herein above. Other applications of the method and kit include the identification of microorganisms in the contamination of food and drinking water.

Biosensor for Detection of Tuberculosis

Topoisomerase I from the tuberculosis-causing pathogen *M. tuberculosis* (MtTopI) belongs to the typeIA family of topoisomerases, which normally require Mg2+ for activity. However, MtTopI only requires this cofactor during the ligation step of catalysis and not during cleavage. Therefore, MtTopI cleavage can be detected even in crude biological samples, which are depleted for Mg2+. Moreover, MtTopI cleaves single stranded DNA in a sequence specific manner, which allows the specific cleavage activity of MtTopI to be distinguished from other nucleases. Hence, a single stranded nucleic acid substrate is provided to the sample to be tested for *Mycobacterium tuberculosis*, and that nucleic acid substrate is then upon cleavage by MtTopI converted to a well-defined product with a specific sequence. This product can then be detected by any suitable method, as described herein above. Thus, in a preferred embodiment of the method of the present invention, the sample is depleted for divalent cations, and/or the kit comprises an agent for depletion of cations. This is for example specifically relevant for the identification of microorganisms, which express a type I topoisomerase that do not require divalent cations for processing a nucleic acid substrate by cleavage and/or ligation, such as MtTopI (*Mycobacterium tuberculosis* topoisomerase I).

For example, the cleavage product is hybridized to a primer anchored to a glass surface and circularized by a DNA ligase (in the presence of Mg2+) after cell remains have been washed away. The generated circle can now serve a template for RCA and the products visualized by hybridization to specific fluorescent probes (cf. FIG. 10).

Medical Use

The technology may be employed for identifying any microorganism and/or any infection in any subject, including humans, non-human animals, such as house-hold stocks, and plants. Other applications of the method include the identification of microorganisms in the contamination of food and drinking water.

The compositions, kits and methods provided herein are also intended for medical use. Specifically, the compositions, methods and medicaments are provided for identifying a microorganism as defined herein. The microorganisms are preferably pathogenic microorganism, i.e. are among the causative agents of an infectious disorder. Therefore, the compositions, kits and methods of the present invention are also provided for the diagnosis of infectious disorders as described herein, in particular for the diagnosis of malaria and/or tuberculosis In a further aspect, the present invention relates to a method of identifying novel lead compounds for treatment of infectious disorders. To this end, a method is provided for evaluating the effect of an agent on a pathogenic microorganism. Based on the compounds identified in such method, the present invention also relates to such agents for use in the treatment of an infectious disorder, in particular malaria and/or tuberculosis.

Diagnosis

So in one main medical aspect, the present invention relates to a method of determining an infectious disorder in a subject, in particular in a human being. The method comprises identifying a microorganism in a sample from said subject by a method of the present invention. The presence of microorganism in said sample is then indicative of said infectious disorder, because the microorganism is a causative agent of that particular infectious disorder. The infectious disorder determined according to the present invention is for example without limitation tuberculosis, malaria, toxoplasmosis or Lyme disease/borreliosis (*Borrelia*).

A large number of microorganisms are known to be associated as causative agents with certain infectious disorders. For example, *Plasmodium falciparum* is known to be a causative agent of malaria, and *Mycobacterium tuberculosis* is known as a major causative agent of human tuberculosis.

The provided method for identifying a microorganism in a sample from subject generally comprises
  i. providing the sample
  ii. providing a double stranded nucleic acid substrate targeted by type I topoisomerase of said microorganism,
  iii. mixing the sample of step i. with the nucleic acid substrate of step ii.
  iv. detecting nucleic acid substrate targeted by type I topoisomerase of said microorganism,
wherein the presence of nucleic acid substrate targeted by type I topoisomerase of said microorganism is indicative of said microorganism.

Generally, the present invention provides a method of determining a disease in a subject, said method comprising identifying a microorganism in a sample from said subject by a method of the present invention as defined herein above, wherein the presence of said microorganism in said sample is indicative of said disease. The method of the invention is here generally understood as a method of identifying a type I topoisomerase-expressing microorganism in a sample, said method comprising
  i. providing the sample
  ii. providing a nucleic acid substrate targeted by a type I topoisomerase of said microorganism,
  iii. bringing the sample of step i. in contact with the nucleic acid substrate of step ii.
  iv. detecting nucleic acid substrate processed by said type I topoisomerase of said microorganism,
wherein the presence of processed nucleic acid substrate is indicative of said microorganism.

The subject diagnosed for a disease according to the method of determining a disease is not necessarily limited to any specific group, family or class of organisms. In one embodiment, however, the subject is a ruminant, a bovine, a ferret, a badger, a rodent, an elephant, a bird, a pig, a deer, a coyote, a camel, a puma, a fish, a dog, a cat, a non-human primate or a human. In a preferred embodiment, the subject is a human subject. Human subjects are for example preferred when testing for human diseases, such as human tuberculosis, and/or malaria. In another embodiment, the subject is a bovine subject; for example when testing for bovine diseases, such as bovine tuberculosis. The disease is any disease of interest, as explained elsewhere herein, for example the disease is an infectious and/or a parasitic disease, and for example the infectious disease is malaria.

Also, the microorganisms identified are explained elsewhere herein; for example, the microorganism is selected from the *Plasmodium* and/or *Mycobacterium* genus.

In one preferred embodiment, the parasitic disease is malaria and/or the microorganism is selected from the *Plasmodium* genus, for example, the microorganism is *Plasmodium falciparum*.

In one embodiment, the infectious disease is human and/or bovine tuberculosis, and/or the microorganism is selected from the *Mycobacterium* genus, for example *Mycobacterium tuberculosis*.

The diagnostic applications of the present invention may be practised in any suitable and practical setup or machinery, which utilizes the system's sensitivity, simplicity and short reaction time. For example, the method may be used in advanced equipment for single cell, single molecule detection, for ultra-sensitive detection of infection sources.

However, in a particularly preferred embodiment, the diagnostic methods are performed in the style of stick tests/dipsticks. A testing dipstick is for example made of paper or cardboard and is impregnated with the reagents required to perform the reaction of the invention. The readout of a dipstick test is preferably presented by a changing color. In this way, dipsticks can be used to test for a variety of liquid samples for the presence of a specific microorganism, and the dipstick can then be employed in easy and efficient diagnosis of infectious disorders, such as any infectious disorder according to the present invention.

Method for Drug Discovery

The species-specific enzyme reactions, particular type I topoisomerase activity, which serve to modify nucleic acids/DNA, and thereby are used for identification of a microorganism according to the present invention, are generally essential for these microorganisms since they are part of DNA metabolism. Any compound capable of specifically blocking, inhibiting or down-regulating the activity of these species-specific enzymes may be used as therapeutic against such microorganisms and/or infectious disorders caused by such microorganisms. The methodology of the present invention can be applied directly to the testing of drugs known for their selective action on specific enzymatic processes in the relevant microorganism. Moreover, the methodology can be used for design of new small molecule drugs against nucleic acids modifying enzyme systems of infectious microorganisms.

Accordingly, the teaching of the present invention may also be employed in drug discovery, because the method provided herein for determining the presence of microorganisms via the present of a specific type I topoisomerase activity, can be used for evaluating the effect of a candidate drug on a microorganism. Any such drug candidates, which display an inhibitory effect on the present of the microorganism and/or on the activity of the toposimerase activity of said microorganism is a suitable drug for treatment of an infectious disorder associated with that microorganism.

Thus, the present invention in one aspect relates to a method for evaluating the effect of an agent on a microorganism in a sample, said method comprising
  i. providing a sample
  ii. providing a nucleic acid substrate targeted by type I topoisomerase of said microorganism,
  iii. providing an agent,
  iv. combining the sample of step i. and the nucleic acid substrate of step ii. with or without the agent of step iii.

v. detecting nucleic acid substrate targeted by type I topoisomerase of said microorganism with or without the agent, wherein an agent capable of reducing the amount of targeted nucleic acid substrate has an inhibitory effect on said microorganism.

In this method, the microorganism, sample, nucleic acid substrate, type I topoisomerase, and/or detection is as defined in claim 1.

Treatment

In yet another aspect, the present invention provides an agent, a composition, a use, or a method for treatment of an infectious disorder, based on a candidate drug identified by a method provided herein. Thus, in a further aspect the present invention relates to a method of treating, preventing or ameliorating an infectious disorder, said method comprising administering an agent identified by a method of the present invention to a subject in need thereof.

Similarly, the invention also provides for an agent identified by a of the present invention and/or a pharmaceutical composition comprising such agent for use in the treatment, prevention or amelioration of an infectious disorder.

EXAMPLES

Example 1

**Development of a Novel *Plasmodium falciparum* Topoisomerase I Specific Biosensor for Diagnosis of Malaria**

This example relates to a DNA based biosensor suitable for at-point-of-care diagnosis of malaria. In this setup, specific detection of malaria parasites in crude blood samples is facilitated by the conversion of single *Plasmodium falciparum* topoisomerase I (pfTopI) mediated cleavage-ligation events, happening within nanometer dimensions, to micrometer-sized products readily detectable at the single molecule level in a fluorescence microscope.

One challenge of detecting enzymatic products is that only few enzymatic products are readily detectable without the use of sophisticated equipment and even then, most products can be detected only when produced in high numbers. For clinically relevant identification of pathogens based on species specific enzymatic activities it is, therefore, necessary to have detection systems that overcome these challenges.

The enzymes Topoisomerase I (hTopI), Flp and Cre all introduce single strand cuts in DNA followed by subsequent ligation of the generated nick in a reaction that involves the formation of a covalent enzyme-DNA cleavage intermediate. This reaction may be utilized to convert self-folding oligonucleotide substrates to closed DNA circles, which subsequently were subjected to Rolling Circle Amplification (RCA) leading to products (RCP) consisting of ~$10^3$ tandem repeats of a sequence complementary to the DNA circles. These RCPs can be visualised at the single-molecule level in a fluorescence microscope by annealing to fluorescent-labelled probes giving rise to one fluorescent spot for each RCP (see FIG. 4 for schematic illustration of the assay). Since the assay involvs no thermal cycling, each RCP represents one closed DNA circle, which in turn represented a single cleavage-ligation event. Hence, this assay allows the detection of TopI, Flp or Cre activity at the single cleavage-ligation event level.

Here, the assay is used for identification of the malaria parasite *P. falciparum* in crude clinical samples based on the specific detection of single pfTopI cleavage-ligation events. First a synthetic gene encoding pfTopI was cloned and the recombinant protein expressed in and purified from *Saccharomyces Cerevisiae* to allow characterization of the enzyme. The ability of pfTopI to cleave the classical hexadecameric sequence known as a preferred cleavage site for most other nuclear typeIB topoisomerases was investigated using a synthetic 75-mer substrate with this sequence. pfTopI cleaved this substrate between nucleotides −1 and +1, which is the preferred cleavage site for other nuclear typeIB topoisomerases, including hTopI, as well as several addition sites located downstream to this position, which is not cleaved by hTopI (FIGS. 1A, and 4).

Figure 5:
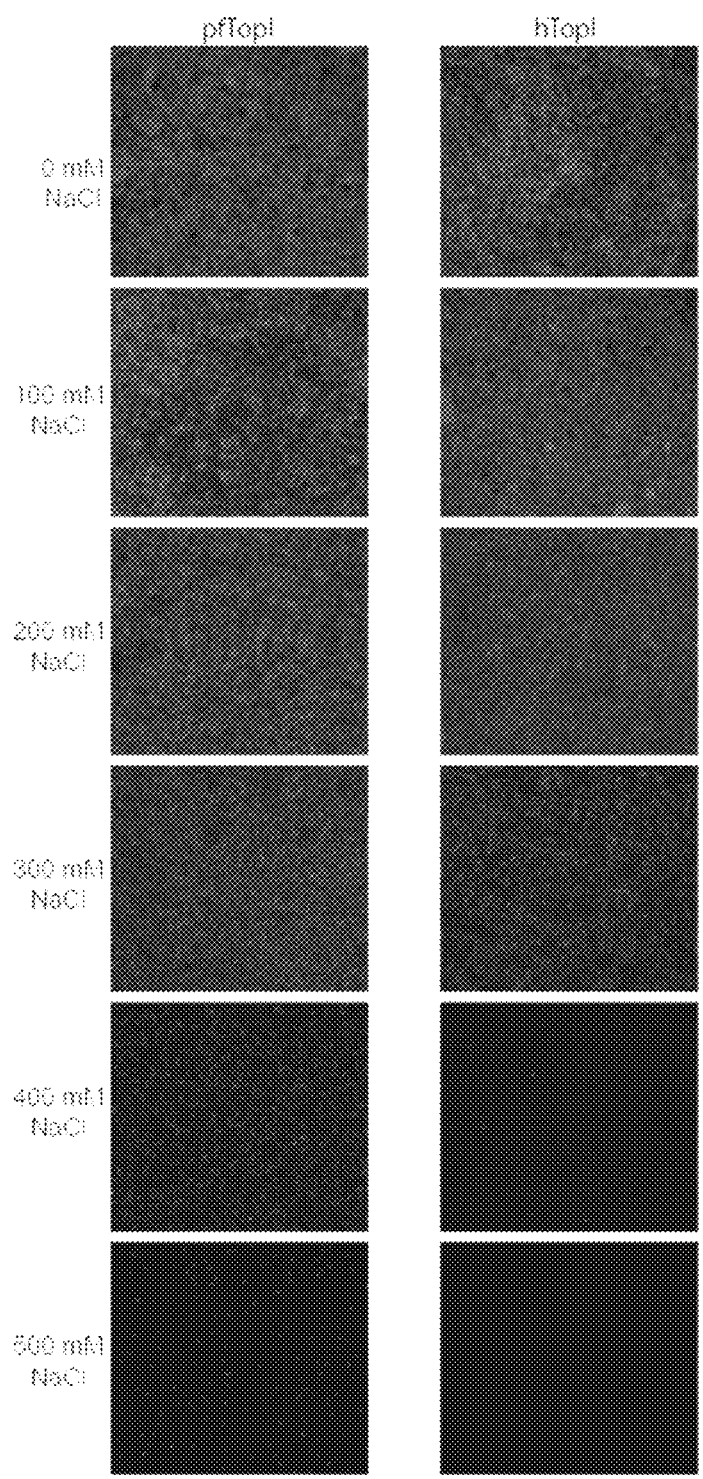
FIG. 5. Comparison of human and *Plasmodium falciparum* type I topoisomerase activity at increasing salt concentrations. The signals on each pictures indicate single cleavage-ligation events mediated by type I topoisomerase detected in an RCA-based biosensor system using the substrate (Su1). pfTopI exhibits a considerably higher salt tolerance than does hTopI.
Figure 6:
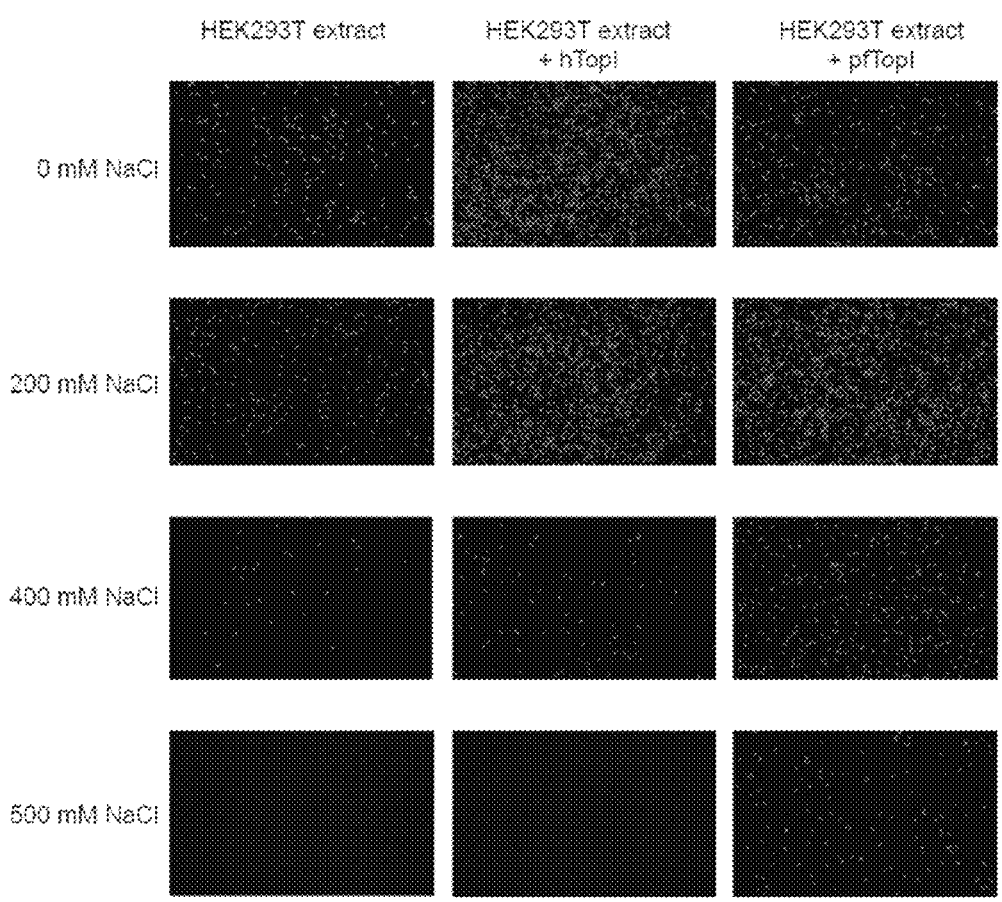
FIG. 6. Detection of human and *Plasmodium falciparum* type I topoisomerase cleavage-ligation events detected in an RCA-based biosensor system using the substrate (Su1) in an extract of HEK293T cells. Increasing the salt concentration enables the specific detection of pfTopI on a background of human cell content including hTopI in extracts from cell lines or human blood (S3 and S4).
Figure 7:
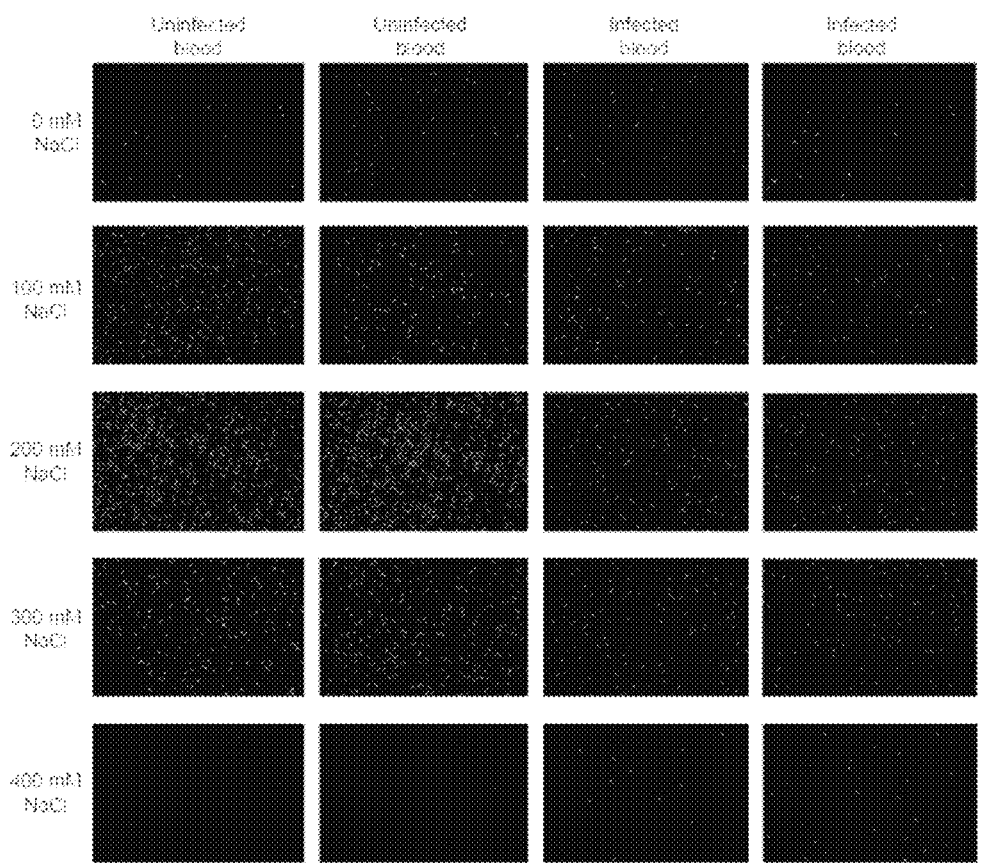
FIG. 7. Detection of type I topoisomerase cleavage-ligation events, detected in an RCA-based biosensor system using the substrate (Su1), in uninfected and infected blood.
Figure 10:
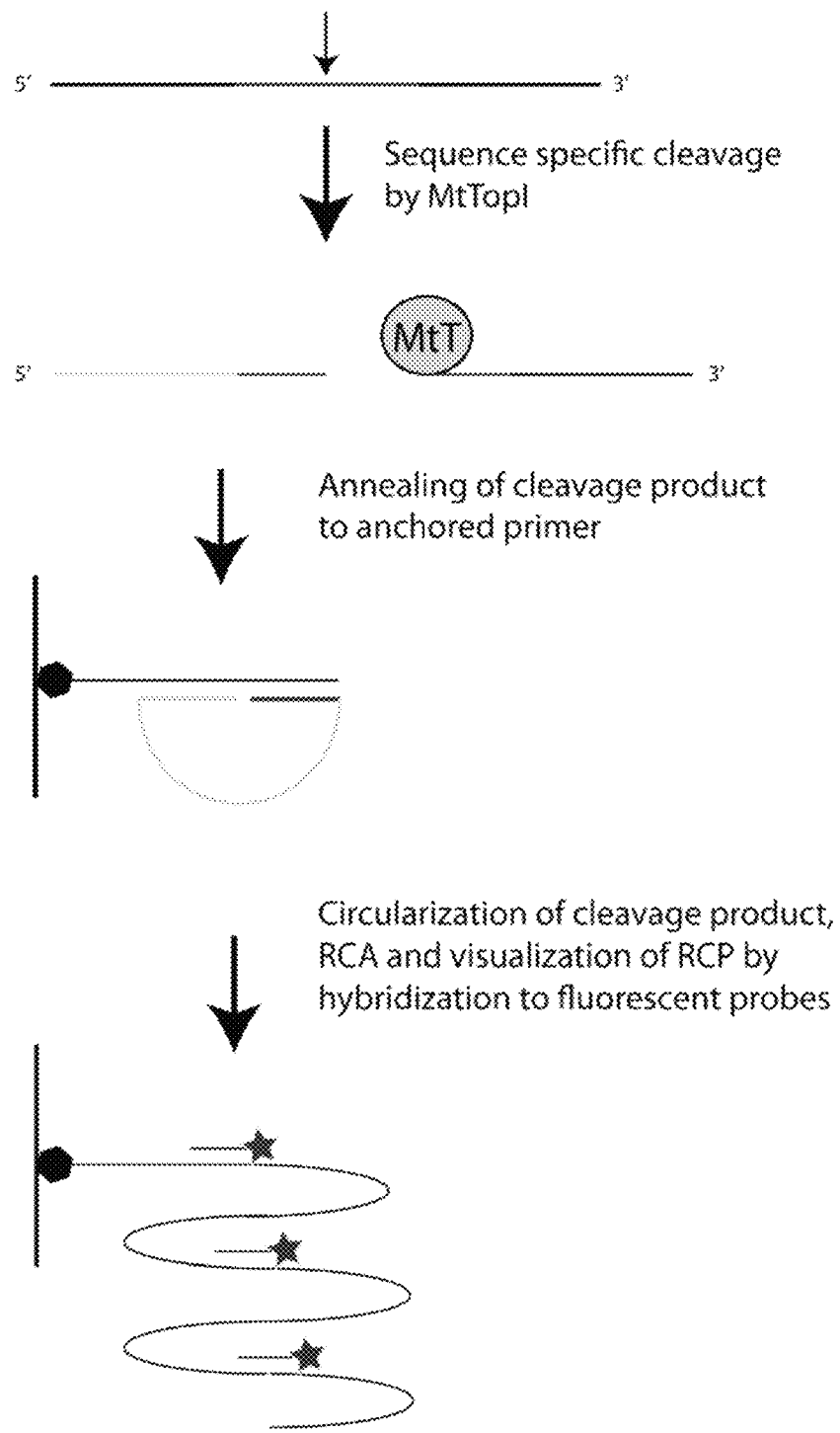
FIG. 10. Detection of MtTopI is achieved by converting a MtTopI specific cleavage product to a closed circle, which is used as template for RCA.
Figure 12:
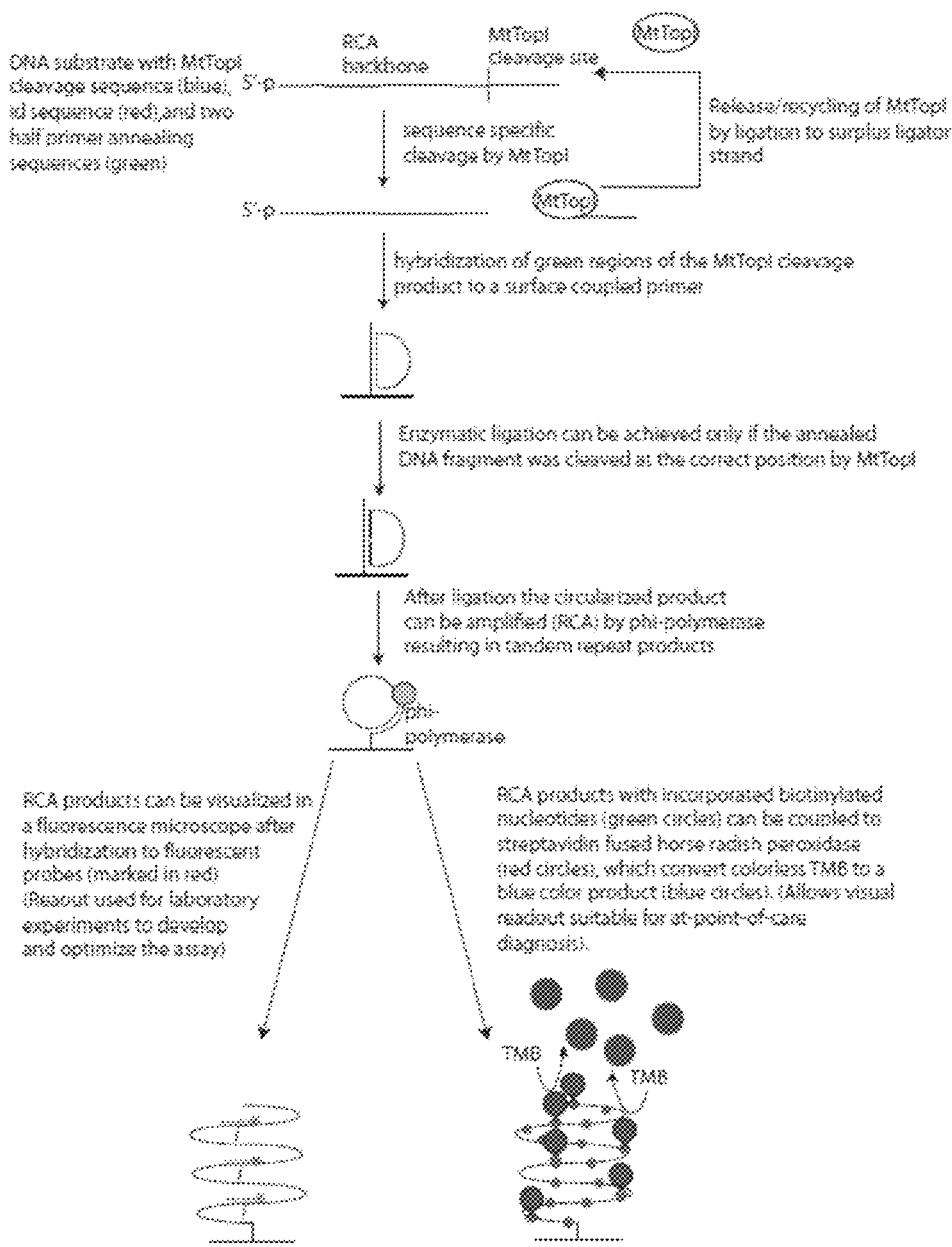
FIG. 12. Assay for detection of *Mycobacterium tuberculosis* TopI
Figure 13:
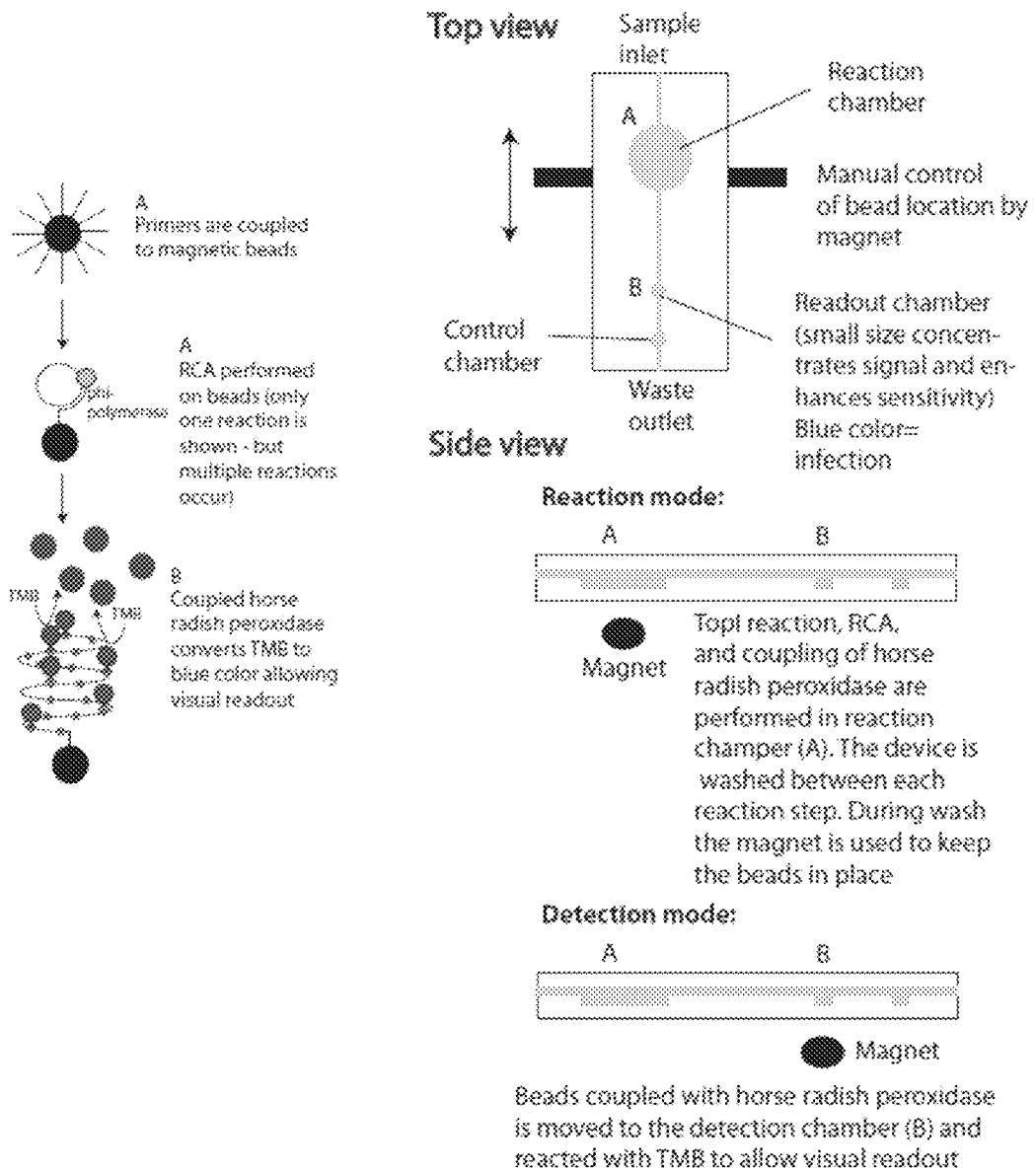
FIG. 13. Overview of at-point-of-care rst line diagnosis suitable for low resource settings with no laboratory facilities and low-trained personnel (no electricity or other special facilities needed). Left panel: Adaptation of assay for reaction/readout device; Right panel: Schematic illustration of crude design for reaction/readout device FIG. 14. Reaction steps for diagnosis of tuberculosis and/or detection of *Mycobacterium tuberculosis*. As reaction control a chip detecting human type I topoisomerase in the same clinical sample is used (based on the RCA principle)—a device with one inlet leading to two reaction chambers with directly coupled beads could be envisioned. The control chamber should be blank as a control for correct washing of the device. All reactions can be performed within 20-40 degree Celsius. The device can be operated by minimally trained personnel and requires no electricity. Readout is performed by the naked eye. The device and similar devices may be operated by low-trained personnel and are also suitable for self-testing.
Figure 14:
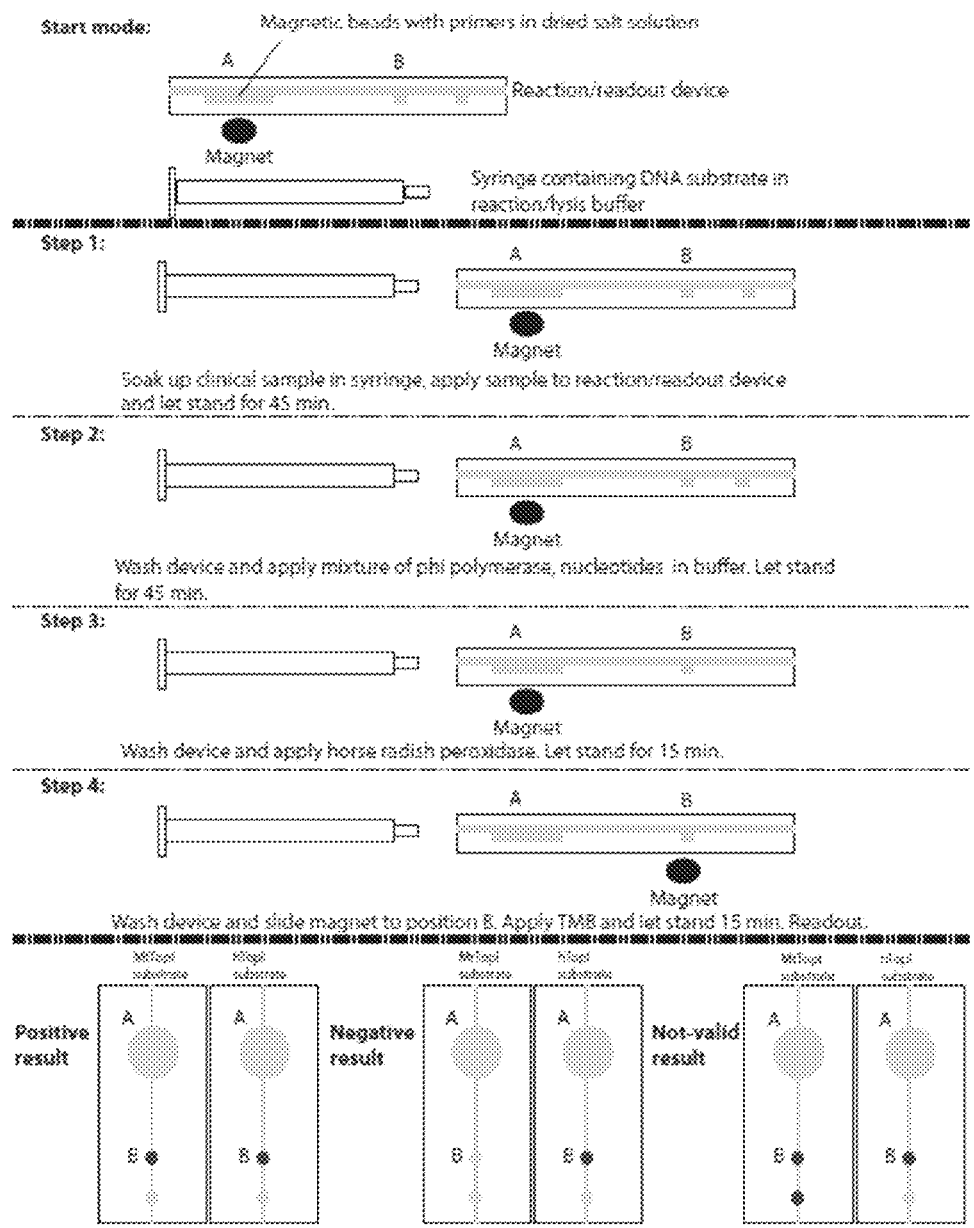

Based on this result it was anticipated that single cleavage-ligation events mediated by pfTopI could be detected in an RCA-based biosensor system using the substrate (Su1) originally developed to detect hTopI activity. As demonstrated in FIG. 5, this expectation held true. Moreover, since pfTopI exhibits a considerably higher salt tolerance than does hTopI (FIG. 5) increasing the salt concentration enabled the specific detection of pfTopI on a background of human cell content including hTopI in extracts from cell lines or human blood (FIG. 6 and FIG. 7). However, the specific detection of pfTopI obtained in this manner was at the cost of sensitivity, with salt (400-500 mM) concentrations high enough to prevent hTopI activity decreasing pfTopI activity.

Figure 4:
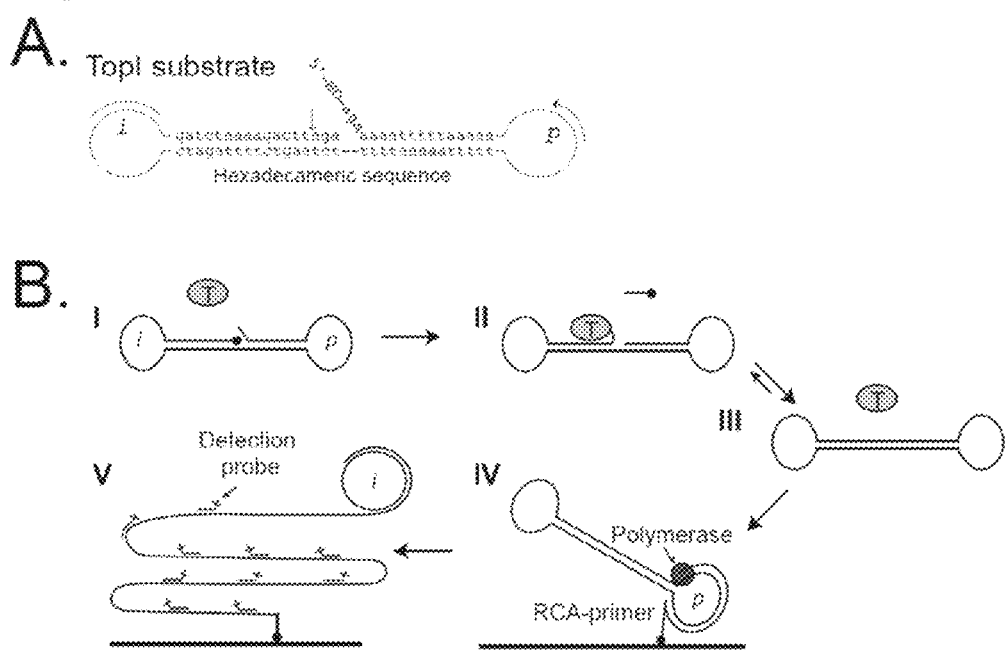

As shown in FIG. 1A and FIG. 4, in contrast to its human counterpart, pfTopI is able to cleave close to DNA ends with high efficiency. Hence, a DNA substrate which is circularized upon cleavage-ligation close to a DNA end may enable specific detection of pfTopI on a background of the human cell extract without compromising sensitivity of the assay considerably. To address this possibility, purified pfTopI was incubated with each of the substrates Su2-Su6 (FIG. 1B) and the products analysed using the RCA based detection system as schematically outlined in FIG. 1C. The sequence of the substrates Su4, Su5, and Su6 was modified to match the sequence that was cleaved with high efficiency in substrate XX. As evident from FIGS. 1D and E, pfTopI was able to convert Su2-Su6 to closed circles readily detectable in the RCA-based biosensor setup, while hTopI was not (one example shown in FIG. 1D). Of the different substrates and assay conditions tested out the utilization of Su2 appeared the most efficient for specific detection of pfTopI (FIG. 1E).

The use of Su2 for detecting pfTopI activity in human cell extracts in the RCA-based biosensor setup was also verified. For this purpose nuclear extracts from HEK-293T cells were incubated with Su1 (which is circularized by hTopI and serve as a control of efficient cell lysis) and Su2 before or after addition of spike-in purified pfTopI followed by RCA and visualization of RCPs as outlined in FIG. 1B. As a control for successful RCA and probe annealing a circularized control circle was added to each sample before annealing to the primer coated slide. As evident from FIG. 2A, red spots corresponding to RCPs originating from Su2 were only observed upon addition of spike-in pfTopI to the extract, verifying that Su2 serves as a substrate specific for pfTopI even in crude cell extracts. As expected, comparative levels of green and blue spots corresponding to RCPs from Su1 and control circles, respectively, could be observed in both samples (FIG. 2A).

To test the use of pfTopI specific RCA-based detection setup for diagnosis of malaria, extracts from either non-infected or in vitro generated *P. falciparum* infected human, Red Blood Cells (RBC) were subjected to analysis essentially as described for the experiments depicted in FIG. 2A.

Consistent with Su2 being circularized only by pfTopI red signals originating from RCPs of this substrate were observed only after incubation with extracts from *P. falciparum* infected RBC (FIG. 2B, right panel), whereas signals originating from RCPs of circularized Su1 or the control circle could be observed upon incubation with extracts from both uninfected and infected RBC (FIG. 2B). Note that the hTopI activity observed in extract from infected RBC (green spots in FIG. 2B, left panel) was considerably lower than in extract from noninfected RBC (green spots in FIG. 2B, right panel). Since the same cell extracts were used in both experiments we believe this to be a side effect of cells suffering in different ways from the *P. falciparum* infection. A similar result as the one shown in FIG. 2B was obtained when analysing extracts from a blood sample from a mildly infected malaria patient (FIG. 8), further verifying the validity of the detection method to specifically detect the presence of *P. falciparum* parasites in clinical relevant samples As evident from FIG. 3B the presented method allows the detection of down to $2\times10^4$ parasites/µl of RBC. In comparison the detection limit of PCR using standard primers specific for *Plasmodium* sp. or *P. falciparum* specific genomic sequences was around 1 parasite/µl of RBC (FIG. 2C), whereas the detection limit of a commercially available malaria RDT was about XX parasites/µl (FIG. 2D). Note, that although PCR is by several orders of magnitude more sensitive than the RCA-based biosensor, at least in its current crude setup, this technique do not allow a quantitative estimation of the infection level (compare lanes 5 and 6 with lanes 3 and 4 of FIG. 3C), which is possible with RCA-based biosensor (compare the right and middle panels of FIG. 3A). Moreover, the PCR analyses required purification and concentration of genomic DNA to perform, whereas the biosensor allowed *P. falciparum* detection directly in crude cell extracts. Regarding sensitivity the presented RCA-biosensor by far outcompetes current state of the art malaria RDT (compare FIGS. 3A and D).

In conclusion, the present example demonstrates the specific, easy and sensitive detection of malaria in clinical relevant samples by visualizing single cleavage-ligation events mediated by pfTopI. This is achieved by a special developed biosensor system in which each catalytic reaction by pfTopI is converted to a micrometer-sized product readily visible at the single-molecule level. Since each pfTopI, potentially can perform thousands of catalytic reactions without losing activity, the sensitivity of the biosensor is would outcompete current immunohistochemical based diagnostic tools and may allow diagnosis based on non-invasive samples such as mucus or saliva, which typically contain only sparse numbers of *P. falciparum* parasites. This can be achieved by concentrating the RCP signals. Note, that concentrating RCPs on sequencing beads significantly improve sensitivity of the assay. With regard to handling and speed, the present method is superior PCR, and provides a quantitative measurement allowing continuous monitoring of disease development and treatment, which PCR cannot provide.

Example 2

Detection of Single Enzymatic Events in Rare- or Single Cells Using Microfluidics Methods Cell culture and transfections. Human embryonic kidney HEK293 cells were cultured in GIBCO's Minimal Essential Medium (MEM) supplemented with 10% fetal bovine serum (FBS) (Atlanta Biologicals), 100 units/mL penicillin and 100 mg/mL streptomycin (Invitrogen) in a humidified incubator (5% CO2/95% air atmosphere at 37° C.). Cells were harvested with 0.25% Trypsin-EDTA (GIBCO) and resuspended in Phosphate-buffered Saline (1×PBS, Cellgro), 1% Pluronic F-68 (Sigma-Aldrich), 0.1% BSA (Invitrogen). The cell densities were adjusted to 0.5-5 million cells/mL and used for enzyme activity detection in the microfluidic system.

Plasmid pCAG-Flpe:GFP for expression of Flpe C-terminally tagged with green fluorescent protein (GFP) in human cells was from Addgene. Transient transfection of pCAG-Flpe:GFP into HEK293 cells was performed using Lipofectamine2000 (Invitrogen) and 8 µg plasmid DNA and was carried out in GIBCO's Reduced Serum Medium (OPTI-MEM) according to the manufacturer's instructions. 24 h after transfection, cells were harvested with 0.25% Trypsin-EDTA and resuspended in Phosphate-buffered Saline, 1% Pluronic F-68, 0.1% BSA. Transfected cells were mixed with non-transfected cells at the ratios stated in the text and the cell densities adjusted to five million cells/mL (for detection of rare cells) or 0.5 million cells/mL (for addressing the detection limit of the REEAD-microfluidic setup) and used for enzyme activity detection in the microfluidic system or in the "large-volume" bulk experimental setup.

Synthetic DNA Substrates, Probes, and Primers. Oligonucleotides for construction of the S(TopI), S(Flp), S(Control) substrates, the RCA-primer, and the fluorescently labelled identification probes for the three substrates were purchased from DNA Technology A/S. The sequences of all used the oligonucleotides have been published previously2. Rolling circle Enhanced Enzyme Activity Detection (REEAD) in bulk setup. The single-molecule TopI and Flp activity assays were performed essentially as described by F. F. Andersen, M. Stougaard, H. L. Jorgensen et al., ACS Nano 3 (12), 4043 (2009), except for the preparation of the cell extracts. In brief, mixtures of transfected and non-transfected HEK293 cells (described above) were incubated for 5 min in lysis buffer (10 mM Tris-HCL pH 7.5, 0.5 mM EDTA, 1 mM DTT, 1 mM PMSF, 0.2% Tween 20).

Subsequently, S(TopI) and S(Flp) were added to the extract at a final concentration of 100 nM and incubation continued for 30 min at 37° C. RCA-based detection of circularized S(TopI) and S(Flp) in the samples was performed as previously published. Rolling circle Enhanced Enzyme Activity Detection (REEAD) in microfluidic system. The microfluidic setup consists of two devices: a flow-focusing droplet generator and a drop-trap. Both devices were fabricated by conventional soft lithography techniques'! 3, casting and curing the PDMS prepolymer on a SU-8 3025 (MicroChem) master of a channel height at around 25µηι. PDMS prepolymer (Sylgard 184) was prepared in a 10:1 (base:curing agent) ratio and cured at 65° C. for 1 hr. Prior to the experiments, the channel was wetted with oil/surfactant for at least 15 min. Two syringe pumps (Harvard Apparatus) were used to control the flow rates of oil/surfactant and reagents independently, forming monodisperse water-in-oil droplets at a frequency of 0.8-1.5 kHz. The droplet volume and generation frequency was controlled by the flow rate ratio, determined by the competition between continuous phase (carrier fluid (FC-40 fluorocarbon oil (3M): the oil/surfactant, flow rate 22.5 µL/min) and disperse phase (aqueous reagents: cells, lysis buffer and substrates, flow rate 2.5 µL/min).

Cells, prepared as stated above, lysis buffer (10 mM Tris-HCL pH 7.5, 0.5 mM EDTA, 1 mM DTT, 1 mM PMSF, 0.2% Tween 20), and substrates (final concentration of 100 nM in the droplets) were loaded in each their channel in the microfluidic device and droplet generation initiated. The generated droplets were harvested in Eppendorf tubes and placed on a primer-printed glass slide (CodeLink Activated Slides from SurModics) prepared as previously described. The PDMS drop-trap was gently placed on top of the glass slide. The geometry of the drop-trap was designed according to the size of generated droplets. The droplets were left to exsiccate for 16 hours. Wash, RCA, and hybridization of probes were performed as previously described.

Microscopy. Epifluorescent and bright field images were captured with an inverted fluorescence microscope (Axio Observer, Zeiss). Monocolor emission from each fluorophore was collected and filtered through appropriate filters and dichroics. Image processing and analysis was performed with MetaMorph (v.7.6.5).

Results

By combining a rolling circle enhanced enzyme activity detection assay with a specially designed microfluidic device, we here demonstrate highly sensitive detection of rare, uncharacteristic cells on a background of bulk wild-type human cells. The combined setup even allowed quantitative detection of enzyme activities in single cells and holds promise for basic research, diagnostic or prognostic purposes. Reliable identification of rare cells different from the bulk of a cell population poses great potential for basic research and for diagnostic or prognostic purposes. The highly sensitive Rolling circle Enhanced Enzyme Activity Detection (REEAD) assay allows analysis of single enzymatic DNA cleavage-ligation events via Rolling Circle Amplification (RCA) of circular DNA products and microscopic visualization of individual Rolling Circle Products (RCP) by hybridization to fluorescent probes (FIG. 15a). In principle, the single-catalytic-event detection limit of REEAD should allow the enzyme content of single cells to be analyzed. However, spreading of signals to a ~9 mm² area with a handheld pipette hampered sensitivity in the original "large-volume" bulk setup. Here, we present the integration of REEAD with a microfluidic setup, allowing the enzymatic content of one or few cells to react with DNA substrates within a minimalized volume and the subsequent concentration of signals to small cavities of a drop-trap device. A concentration independent detection of rare Flp-recombinase expressing human cells is demonstrated on a background of wild-type cells and multiplexed detection of Flp-recombinase and hTop1 activities in single cells. The substrates S(Top1) or S(Flp) for hTop1 or Flp-recombinase REEAD were:

```
S(Top1),
                                         (SEQ ID NO: 25)
5 -AGAAAAATTT TAAAAAAAC TGTGAAGATC GCTTATTTTT

TTAAAAATTT TTCTAAGTCT TTTAGATCCC TCAATGCTGC

TGCTGTACTA CGATCTAAAA GACTTAGA -3';

S(Flp),
                                         (SEQ ID NO: 26)
5 -TCTAGAAAGT ATAGGAACTT CGAACGACTC AGAATGAGGC

TCAATCTAAT GGACCCTCAA TGCACATGTT TGGCTCCCAT

TCTGAGTCGT TCGAAGTTCC TATACTTT-3'.
```

Figure 17:
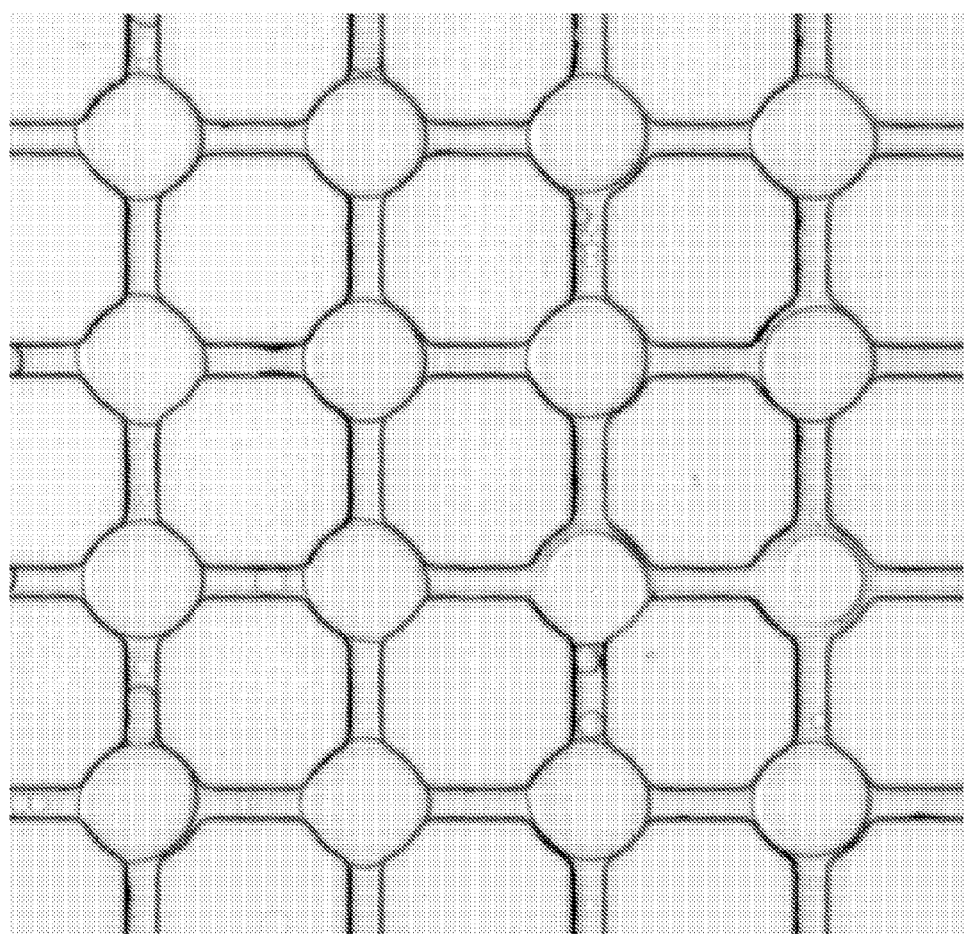
FIG. 17. Droplets in drop-trap. Light microscopy of drop-traps encapsulating 100 pL water-in-oil droplets. The drop-trap cavities are designed to each contain one droplet, which is spatially isolated from other droplets. Droplets are seen as round spheres in the cross-sections of the drop-trap grid.

Each of the substrates comprised one oligonucleotide that is converted to a closed circle by a single hTop1 or Flp-recombinase cleavage-ligation event. As a positive control of RCA, a pre-formed DNA circle was used (S(control)) (FIG. 15a). To investigate whether REEAD could be integrated with the microfluidic setup (FIG. 15b) HEK293 cells, to be analyzed for endogenous hTop1 activity, were loaded into one channel, S(Top1) and S(control) into a second, and lysis buffer into a third channel of the microfluidic device. By competition with oil the four components were confined in lipid surrounded picoliter droplets, which were directed through a serpentine channel to ensure complete content mixing (FIG. 15b). Cell lysis allowed hTop1 to interact with and circularize S(Top1). After exit from the microfluidic system, single droplets were captured in each their cavity of the drop-trap (FIGS. 15c and 17) and exsiccated on a DNA primer-coated glass slide. This allowed RCA of S(control) and circularized S(Top1). RCA of unreacted S(Top1) was prevented as described by M. Stougaard, J. S. Lohmann, A. Mancino et al., ACS Nano 3 (1), 223 (2009). The resulting RCPs were visualized at the single-molecule level by microscopy upon annealing of fluorescent probes. As shown in FIG. 15d, the combination of REEAD and microfluidics enabled multiplexed detection of S(control) (blue) and hTop1 reacted S(Top1) (green) in a pattern matching the drop-trap cavities. In the presented experiment the microfluidic system was fed with five million cells/mL. As estimated from the Poisson distribution (FIG. 18) and confirmed experimentally (FIG. 19) this cell density resulted in –60% of droplets without cells and –40% with one or more cells8. Consistently, all drop-trap cavities contained equally distributed S(control) originating blue signals, while only a part of them contained green signals arising from circularized S(Top1).

Figure 16:
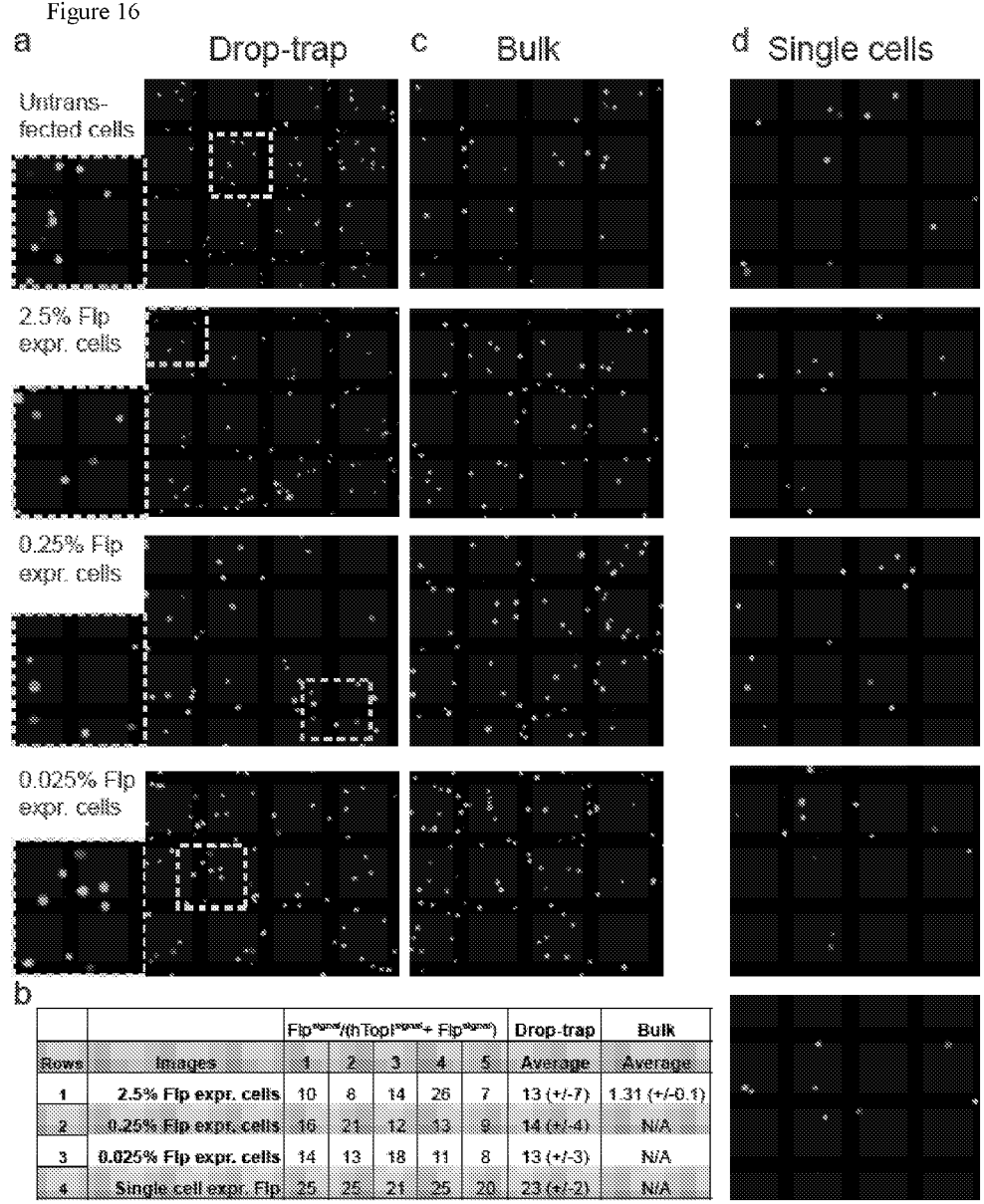
FIG. 16. Detection of enzyme activities in rare- or single cells. (a) Five million cells/mL of HEK293 cells containing 2.5%, 0.25% or 0.25% Flp-recombinase expressing cells were analyzed for Flp-recombinase and hTopI activity using the REEAD-microfluidic setup. Drop-trap cavities containing red signals (dark spots) corresponding to Flp-recombinase activity were selected, (b) Shows the percentage of red signals (dark spots) in five cavities of the drop-trap when five million cells/mL containing 2.5%, 0.25% or 0.25% Flp-recombinase expressing cells were analyzed for Flp-recombinase and hTopI activity (row 1-3) or when 0.5 million cells/mL containing 2.5% GFP-recombinase expressing cells were analyzed (row 4). (c) The result of analyzing the cell populations used in (a) for Flp-recombinase and hTopI activity in the "large-volume" bulk assay setup, (d) Same as (a) except that 0.5 million cells/mL containing 2.5% Flp-recombinase expressing cells was analyzed. hTopI and Flp-recombinase specific signals were visualized by FAM-(green/light) and TAMRA-(red/dark) labeled probes, respectively.
Figure 18:
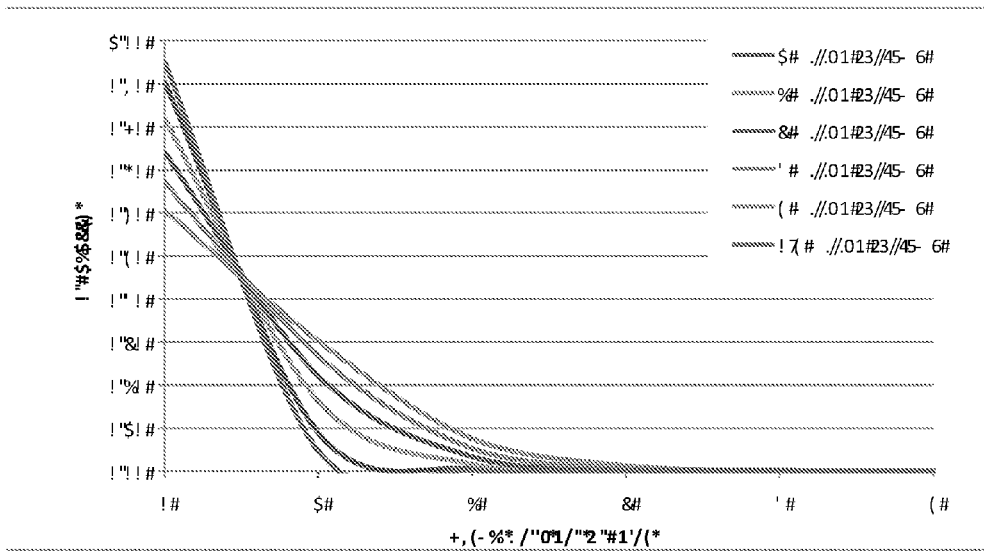
FIG. 18. Theoretical estimate of the amount of cells in the picoliter droplets as a function of cell density. Encapsulation of cells within the 100 pi monodisperse droplets can be estimated as a Poisson (stochastic) distribution. According to this distribution, increasing the density of cells loaded into the system from 0.5 to five million cell/mL results in an increasing amount of cells encapsulated in each droplet. For example, when using the lowest cell density, 4.8% of droplets are expected to contain a single cell whereas only 0.1% of droplets are expected to contain two or more cells. This was also observed by Konry et al. 7, 11. Loading of five million cells/mL, on the other hand, will theoretically result in 30% of the droplets having single cells and 9.1% of droplets containing two or more cells.
Figure 19:
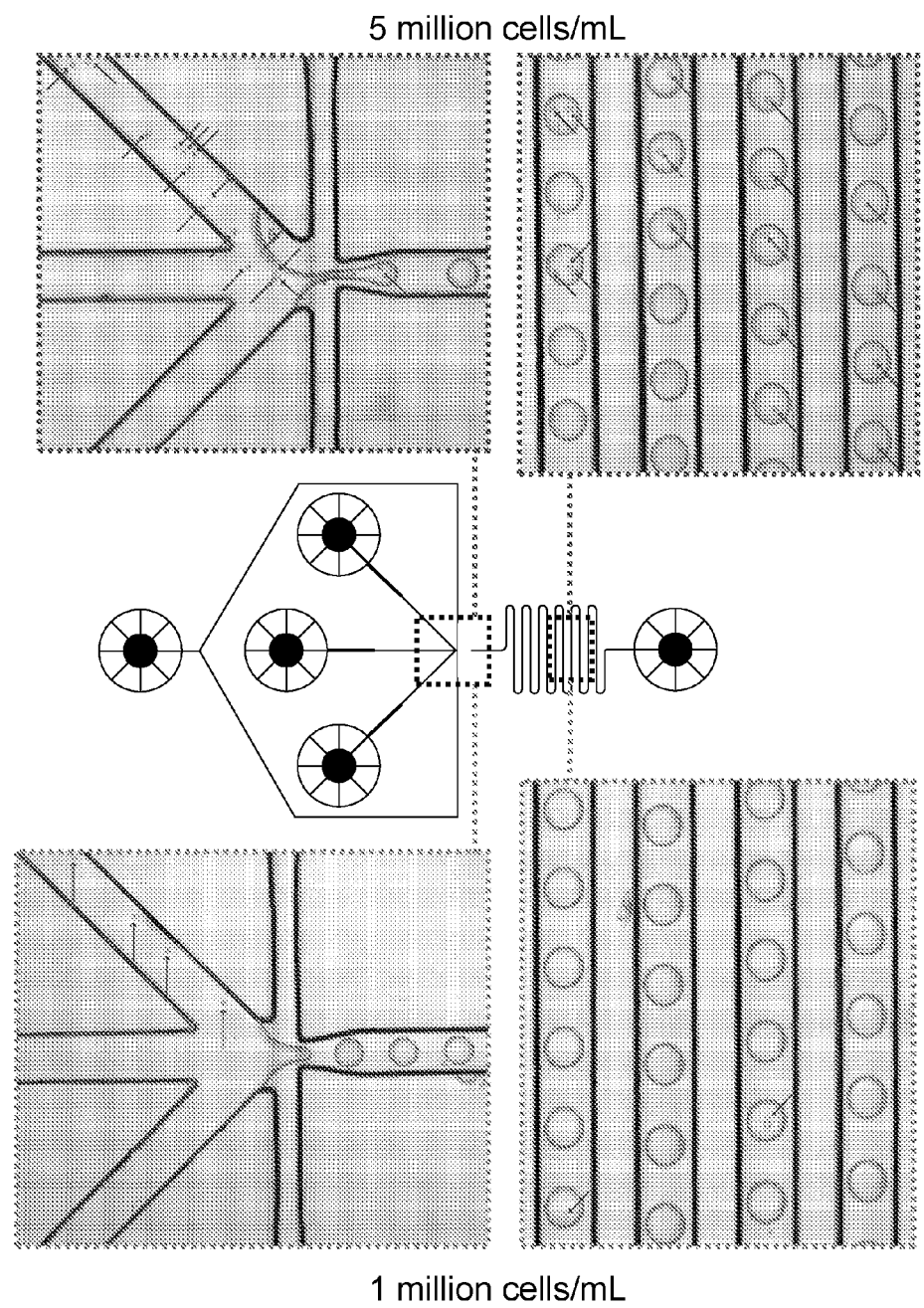
FIG. 19. The density of cells loaded into the microfluidic device determines the number of cells per droplet. The middle of the image is a schematic illustration of the PDMS microfluidic device. As shown the device consists of three water phase inlets, an oil inlet, and an outlet for the generated droplets. Top panel, microscopic view of droplet entrapped cells resulting from loading HEK293 cells with a density of five million cells/mL into the microfluidic device. Consistent with the Poisson distribution (FIG. 18) this cell density results in approximately 40% of cell containing droplets. As evident these are not always single cells, and several cells are confined in the same droplet in approximately 9% of the cases. Bottom panel shows a microscopic view of the droplet encapsulated cells resulting form loading a cell concentration of one million cells/mL into the microfluidic device. Theoretically, loading of at this cell density ensures that no more than a single cell is confined in each droplet (FIG. 18). This was confirmed experimentally by observation of more than 5000 droplets revealing the encapsulation of one or no cells in each droplet. Note, that for the presented experiments, the substrate and lysis buffer, applied in channel two and three of the microfluidic device when performing REEAD experiments, were substituted by PBS to ensure the integrity of the cells since lysed cells cannot be detected in the light microscope used for visualization of cells and droplets in this experiment.
Figure 20:
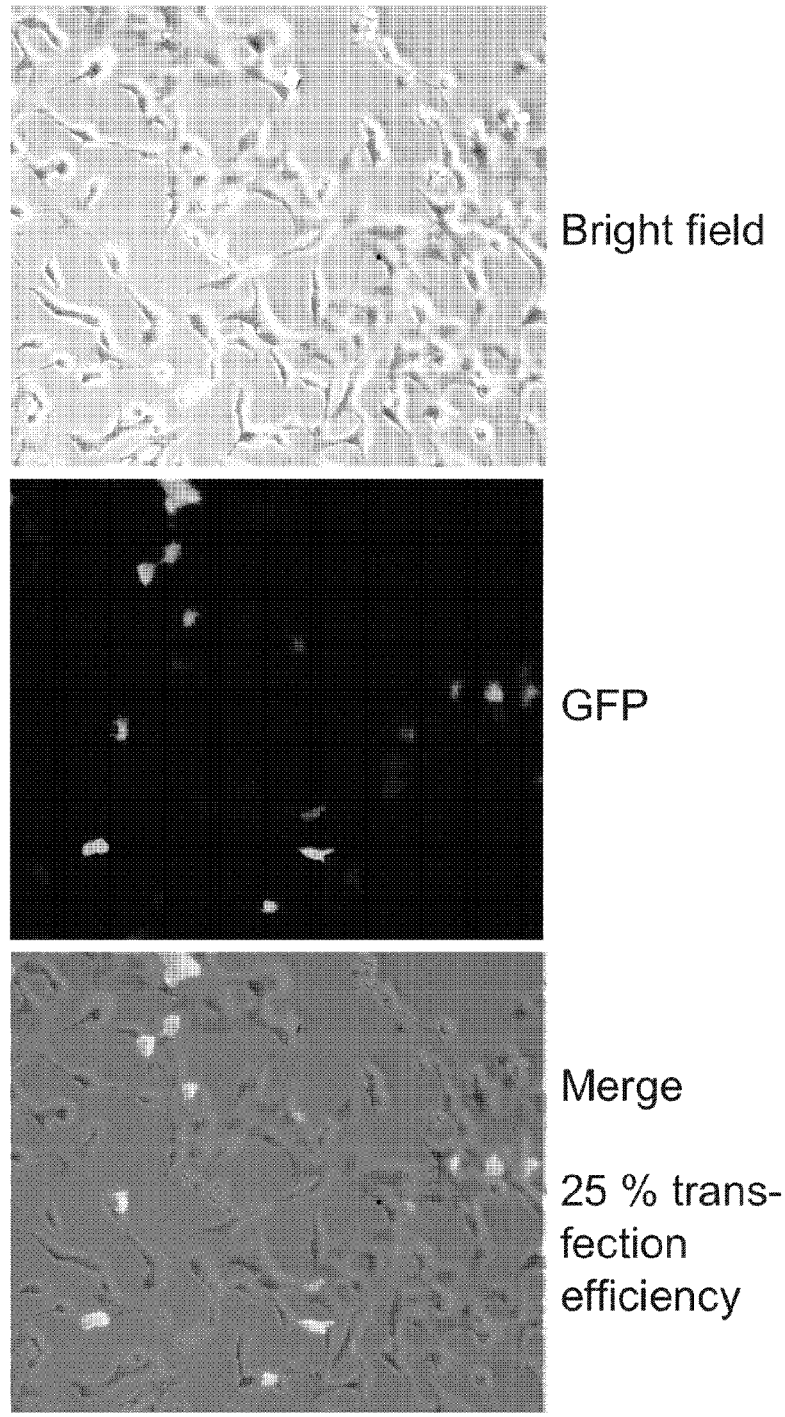
FIG. 20. Generation of Flp-recombinase expressing HEK293 cells. HEK293 cells were transfected with the plasmid, pCAG-FIpe:GFP, expressing recombinant FIpe fused to GFP. FIpe is a Flp-recombinase variant with enhanced thermostability and activity at 37° C., making it suitable for studies in mammalian cells8. GFP (green fluorescent protein) was fused to FIpe to allow the number of FIpe expressing cells to be calculated by simply counting the number of green fluorescent cells. Note, that the fusion between GFP and FIpe does not affect the activity of the recombinase. Top and middle panels show a bright field image and a fluorescence image, respectively, of the transfected cells, while the bottom panel shows a merge of the bright field and fluorescence images. A transfection efficiency of 25% was determined by calculating the percentage of total cells expressing GFP.

To investigate how the combined REEAD-microfluidic setup performs in detecting rare cells different from the bulk of a cell population, we used HEK293 cells containing different proportions of Flp-recombinase expressing cells as a model (FIG. 20). Five million cells/mL containing 2.5%, 0.25% or 0.025% Flp-recombinase expressing cells were loaded into the microfluidic device together with S(Top1), S(Flp) and lysis buffer as described above. After entrapment of droplets and RCA, circularized S(Top1) was visualized by green and circularized S(Flp) by red fluorescence. As evident from FIG. 16a, red Flp-recombinase specific signals (dark spots) could be detected on the background of green signals (light spots) originating from endogenous hTop1 activity present in all the cells. Moreover, although the number of drop-trap cavities containing red signals decreased with decreasing density of Flp-recombinase expressing cells the average percentage of Flp-recombinase specific red signals (dark spots) in the drop-trap cavities that did contain red signals was similar regardless the dilution of Flp-recombinase expressing cells (FIG. 16b). Note that, as discussed below, the relatively large deviation of red (dark spots) signals present in individual drop-trap cavities most probably results from the uptake of more than one cell in some droplets when feeding the system five million cells/mL (FIGS. 18 and 19). In comparison to the results obtained by microfluidic-combined REEAD, red signals (dark spots) originating from Flp-recombinase activity was not detectable in cell populations containing less than 2.5% Flp-recombinase expressing cells when measured in a "large-volume" bulk experimental setup (FIG. 16c).

To address the detection limit of the REEAD-microfluidic setup, 0.5 million cells/mL containing 2.5% Flp-recombinase expressing cells were loaded into the system and the activity of Flp-recombinase or hTop1 detected. At this cell density no more than one cell was encapsulated in each droplet (FIGS. 18 and 19) and, hence, the signals in each drop-trap cavity (FIG. 17 and FIG. 16d) represented the enzyme activities of a single cell. The figure shows the result of encapsulating Flp-recombinase expressing cells. However, cavities with green signals only, representing a cell without Flp-recombinase, were also observed. The percentage of Flp-recombinase originating signals (red/dark spots) relative to all signals in single cells varied between 20-25% with an average of 23+1-2% (FIG. 16b). When comparing this to the results obtained with five million cells/mL it is clear that when using the high cell density the amount of cells and the relative distribution of wild-type versus Flp-recombinase expressing cells trapped in each droplet varies. For example image #4 in row 1 of FIG. 16b may result from entrapment of one or more Flp-recombinase expressing cells while images #3 and #5 in the same row may result from encapsulation of Flp-recombinase expressing and wild-type cells in the ratio 1:2 and 1:3, respectively.

In conclusion, the detection of Flp-recombinase originating signals independent of the density of Flp-recombinase expressing cells in a population taken together with the comprehensive detection of signals from hTopl or Flp-recombinase activity in single cells demonstrates that the REEAD-microfluidic setup allow diminutive numbers of uncharacteristic cells in a population to be discovered. The high sensitivity of the REEAD-microfluidic setup compared to the conventional "large-volume" bulk setup without doubt relies on the diminished reaction volume and subsequent concentration of signals. These features of the REEAD-microfluidic setup hold promise for analysis of cell populations including cell-to-cell variations for research purposes and for early diagnosis/prognosis of cancer or pathogen infections. Indeed, existing RCA-based single molecule techniques for detection of disease relevant nucleotide sequences or proteins can be combined with the microfluidic setup. In particular, the REEAD-microfluidic setup can be used for the identifying type I topoisomerase-expressing microorganisms, such as *Plasmodium falciparum* and/or *Mycobacterium tuberculosis*. In this way, the REEAD-microfluidic setup may be used for the diagnosis of malaria and tuberculosis, respectively.

Example 3

*Plasmodium* Topoisomerase I Specific Nucleotide Biosensor for Diagnosis of Malaria Methods SDS PAGE and Western blotting: pfTopl and hTopl were analyzed by electrophoresis on 10% SDS polyacrylamide gels and the proteins either stained with Coomassie brilliant blue following standard procedures or transferred to a nitrocellulose membrane in 25 mM Tris, 192 mM glycine, 0.1% (w/v) SDS and 20% methanol. Western blotting was performed using standard procedures (primary antibody, polyclonal antibody to hTopl from *Scleroderma* Patient Serum (TopoGEN); secondary antibody, ImmunoPure Goat Anti-Human IgG-HRP (Thermo Scientific)).

Synthetic substrates for cleavage assays: All oligonucleotides were purchased from DNA Technology A/S and purified by denaturing polyacrylamide gel electrophoresis. The sequences of the oligonucleotides are as follows: OL37: 5'-CGAATTCGCT ATAATTCATA TGATAGCGGA TCCAAAAAAG ACTTAGAAAA AAAAAAAGCT TAAGCAA26, OL56: 5'-TTGCTAAGC TTTTTTTTTT TCTAAGTCTT TTTTGGATCC GCTATCATAT GAAT-TATAGC GAATTCG26, OL62: 5'-GCCTGCAGGT CGACTCTAGA GGATCTAAAA GACTTAGAAA AATTTTTAGG CTCAATCTAG AAGTTCCTAC TTAGA, OL63: 5'-ATTTTTCTAA GTAGGAACTT CTAGATTGAG CCTAAAAATT TTTCTAAGTC TTTTAGATCC TCTA-GAGTCG ACCTGCAGGC. The oligonucleotides representing the scissile strands (OL37 and OL62) were 5'-radiolabeled by T4 polynucleotide kinase (NEB) using [γ-32P] ATP as the phosphoryl donor. The oligonucleotides were annealed pairwise with a 2-fold molar excess of the bottom strand over scissile strand as previously described.

Detection of PfTopl activity using radio-labeled DNA substrates: DNA cleavage reactions were carried out by incubating 20 nM duplex OL37/OL56 or OL62/OL63 with 500 fmol of pfTopl or hTopl in the absence or presence of 60 nM CPT for 20 min at 37° C. in 10 mM Tris (pH 7.5), 5 mM MgCI2, and 5 mM CaCl2 in a final volume of 20 µl. After the 20 min incubation, reactions were stopped with 0.5% (w/v) SDS. Samples were subjected to ethanol precipitation, resuspended in 10 µl of 1 mg/ml trypsin and incubated at 37° C. for 30 min. Reaction products were analyzed by denaturing polyacrylamide gel electrophoresis following standard procedures, and radioactive bands were visualized by PhosphorImaging.

Sequences of Oligonucleotide Sensor, Primers and Probes

```
S(hTop1):
5'-AGAAAAATTT TTAAAAAAAC TGTGAAGATC GCTTATTTTT

TTAAAAATTT TTCTAAGTCT TTTAGATCCC TCAATGCTGC

TGCTGTACTA CGATCTAAAA GACTTAGA1.

pfTop1(S1):
5'-TCTAGAAAGT ATAGGAACTT CGAACGACTC AGAATGACTG

TGAAGATCGC TTATCCTCA ATGCACATGT TTGGCTCCCA

TTCTGAGTCG TTCGAAGTTC CTATACTTT7.

pfTop1(S2):
5'-CATACATTAT ACGAAGTTAT GAGCGTCTGA GTATGACTGT

GAAGATCGCT TATCAGTGAA TGCGAGTCCG TCTACTCATA

CTCAGACGCT CATAACTTCG TATAATGT7.

pfTop1(S3):
5'-ATTATAATTT TTTGGAACTT CGAACGACTC AGAATGACTG

TGAAGATCGC TTATCCTCAA TGCACATGTT TGGCTCCCAT

TCTGAGTCGT TCGAAGTTCC AAAAAATT.

pfTop1(S4):
5'-TTATAATTTT TTGGAACTTC GAACGACTCA GAATGACTGT

GAAGATCGCT TATCCTCAAT GCACATGTTT GGCTCCCATT

CTGAGTCGTT CGAAGTTCCA A AAA ATT.

pfTop1(S5):
5'-ATTTTTCTAA GTCTTTTAGA TCGAACGACT CAGAATGACT

GTGAAGATCG C TTATCCTCA ATGCACATGT TTGGCTCCCA

TTCTGAGTCG TTCGATCTAA AAGACTTAGA.

Control-circle substrate:
5'-AGAAAAATTT TTAAAAAAAC TGTGAAGATC GCTTATTTTT

TTAAAAATTT TTCTAAGTCT TTTAGATCCCGA GATGTACCGC

TATCGTCATG ATCTAAAAGA CTT.

Control-circle was prepared as described
previously!
```

-continued

RCA primer:
5'-AMINE-CCAACCAACC AACCAAATAA GCGATCTTCA CAGT1.

Fluorescent probes:
For detection of S(hTop1):
5'-"F"-GTAGTACAGC AGCAGCATTG AGG1.

For detection of S1-S5:
5'-"F"-GGAGCCAAAC ATGTGCATTG AGG7.

For detection of control-circle:
5'-"F"- CCGAGAT GTACCGCTAT CGT.

"F" indicates fluorescent labelling where Cy5, rhodamine or FITC were used for blue, red or green fluorescence, respectively.

Results and Discussion

Figure 21:
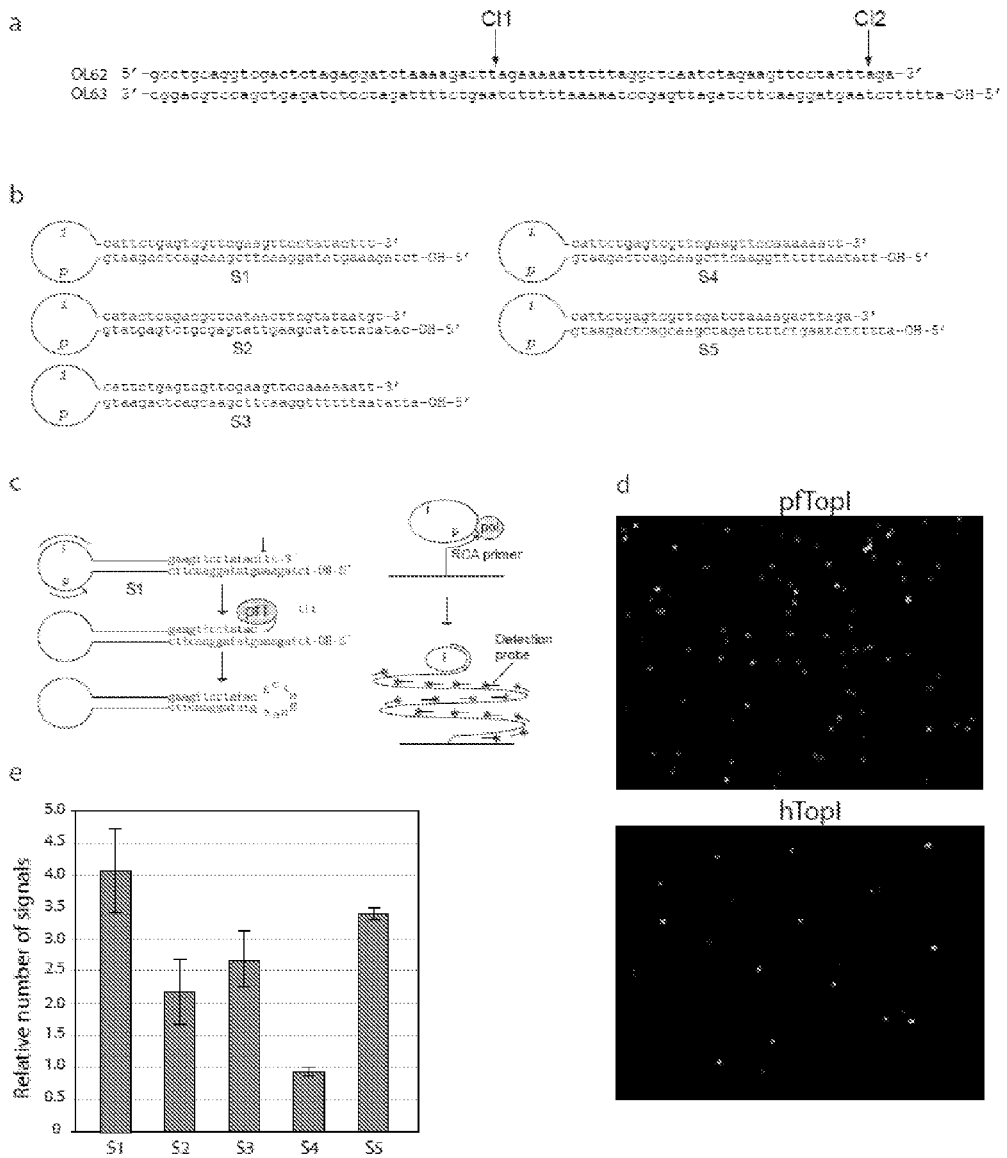
FIG. 21. Development and test of nucleotide sensors for detection of pfTopl. a, schematic illustration of pfTopl cleavage sites on a double-stranded DNA fragment. Cleavage sites are indicated by an arrow denoted Cl1 or Cl2. Cleavage site Cl1 was shared between hTopl and pfTopl, while cleavage site Cl2 was specific for pfTopl. b, schematic illustration of nucleotide sensors (S1-S5) tested for reactivity with pfTopl. Each potential sensor folds into a hairpin structure. The single-stranded loop region contains an p-sequence matching a primer used to template RCA and a i-sequence allowing annealing of a specific fluorescent probe to generated RCPs. The double-stranded stems of S1-S5 contain different nucleotide sequences matching the degenerate consensus recognition sequence of nuclear typeIB topoisomerases. c, schematic illustration of the REEAD setup exemplified by pfTopl reaction with S1. pfTopl mediated cleavage-ligation at the end of S1 generates a single-stranded DNA circle that is subjected to solid support RCA initiated from a glass slide-coupled primer with a sequence matching the p-sequence of S1. Unreacted S1 cannot template RCA. The generated RCPs are visualized microscopically upon hybridization of a fluorescent probe annealing to the i-region of RCPs. The putative cleavage site for pfTopl is indicated by an arrow. Grey ellipse labeled pfT denotes pfTopl while grey ellipse labeled pol denotes the Phi29 polymerase, d, shows an example of the microscopic view obtained upon incubation of S1 with pfTopl (top panel) or hTopl (bottom panel) in the REEAD setup. RCPs originating from circularized S1 and control circle were visualized by rhodamine-(red) and FITC-(green) labeled fluorescent probes, respectively, e, Quantitative depiction of the results obtained when incubating S1-S5 one at a time with purified pfTopl followed by RCA and microscopic visualization of RCA. The number of red and green fluorescent spots corresponding to individual RCPs originating from circularized S1-S5 and added control-circle, respectively, were counted in 15-30 microscopic views of each experiment. The bar chart shows the number of red spots divided by the number of green spots counted in three individual experiments.
Figure 24:
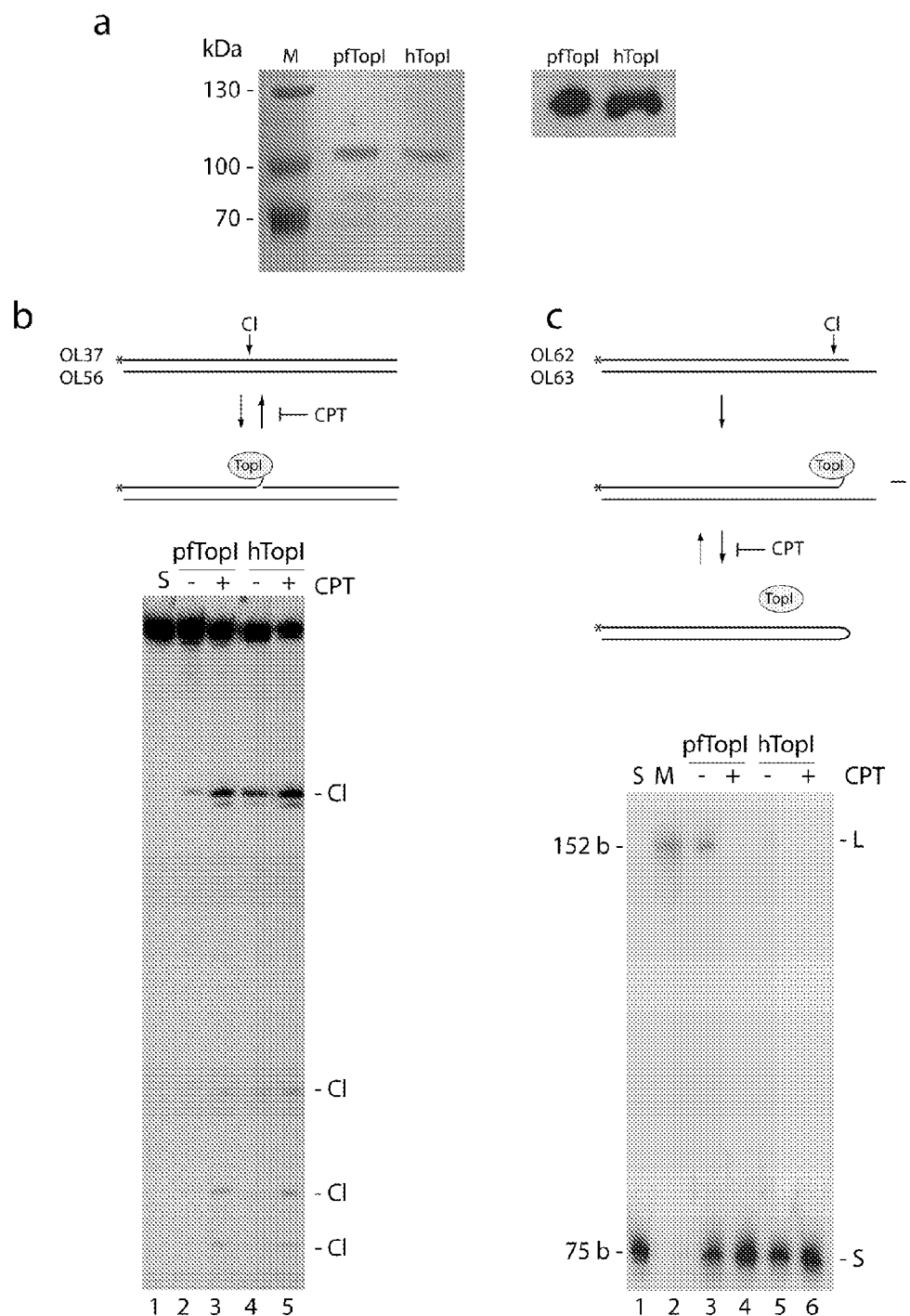
FIG. 24. Comparison of DNA recognition by pfTopl and hTopl. Recombinant hTopl and pfTopl were purified to homogeneity. The resulting protein fractions were analyzed in SDS-PAGE and visualized by Coomassie stain for purity and Western-blotting using a poly-clonal anti-Topi antibody for identity. The DNA recognition potentials of the two enzymes were compared by incubating each of them with 5'-end P32-labelled double-stranded DNA fragments (OL37/OL56 or OL62/OL63) as described in the Methods section below. To allow detection of clevage, the anticancer drug camptothecin, which specifically inhibits the religation step of Topi catalysis were added to the reaction mixtures while the religation reaction could be observed by omitting camptothecin from the reaction. The result of this analysis demonstrated that pfTopl recognizes and cleaves the sites cleaved by hTopl except that pfTopl unlike hTopl is also capable of cleaving double-stranded DNA a few bases upstream to a 3-end followed by ligation of a protruding 5'-end. a, left panel; shows the result of analysing purifed pfTopl or hTopl by SDS-PAGE followed by coomassie stain. Lane 1, is a size marker with sizes of specific bands indicated to the left of the figure. Right panel, same as left panel except that the bands corresponding to pfTopl or hTopl were visualized by Western blotting using an polyclonal anti-Topi antibody, b, top panel; is a schematic illustration of cleavage-ligation reactions shared by pfTopl and hTopl (an example of a cleavage site is indicated by an arrow marked CI). Bottom panel, shows the result of incubating either pfTopl or hTopl with an end-labelled double-stranded DNA fragments in the absence or presence of camptothecin followed by denaturing gel-electrophoretic analysis of the results. The radioactive reaction products were visualized by PhosphorImaging. Bands representing the most pronounced cleavage products generated by both pfTopl and hTopl are indicated with CI to the right of the gel picture, c, top panel, is a schematic illustration of the cleavage-ligation reaction mediated by pfTopI but not hTopI at the end of a double-stranded DNA fragment having a sligthly protruding 5'-OH end. The pfTopI cleavage site is indicated by a arrow marked CI. Bottom panel, shows the result of incubating pfTopl or hTopI in the absence or presence of camptothecin as indicated on the figure. A ligation product is only observed upon incubation of the substrate with pfTopI in the absence of camptothecin (lane 3). The mobility of this product correspond to 152 bases, which in turn correspond to pfTopI mediated cleavage 3 bases upstream to the 3'-end of the substrate followed by ligation of the protruding 5'-OH end of the non-cleaved strand. The cleavage product itself could not be observed directly (lane 4) due to a mobility very close to the substrate band. Note, that a trypsin-resistant peptide remains bound to the cleavage product causing a slight gel-electrophoretic retardation of this product. Hence, cleavage products arising from cleavage a few bases upstream to the 3-end of the 75-mer are scattered by the substrate band. CPT, camptothecin; CI, cleavage product; L, ligation product; S, substrate control; M, size marker. The sizes of marker bands are indicated to left of the gel-pictures.

Like human topoisomerase1 (hTop1), pfTop1 belongs to the family of nuclear typeIB topoisomerases, which introduce transient single-strand breaks in double-stranded DNA with preference for a very degenerate consensus sequence. Cleavage results in a covalent enzyme-DNA intermediate allowing religation of the generated nick (FIG. 23). To demonstrate that different DNA recognition by pfTop1 and hTop1 allows the design of a pfTop1-specific biosensor to be used in a Rolling-Circle-Enhanced-Enzyme-Detection (REEAD) setup, purified recombinant pfTop1 or hTop1 were reacted with double-stranded DNA in a standard cleavage assay (FIG. 24). The result demonstrated that besides cleaving the sites cleaved by hTop1, pfTop1 can cleave DNA close to a 3-end and ligate a protruding 5'-end of the non-scissile strand, which hTop1 cannot (FIG. 21 a). Based on this, five different oligonucleotides with potential of being circularized specifically by pfTop1 cleavage-ligation were designed. These oligonucleotides (PfTop1 (S1-S5)) all folded into a hairpin structure containing a probe- and a primer-annealing sequence in the single-stranded loop and a potential pfTop1 recognizable sequence at the end of the double-stranded stem region (FIG. 1 b). The ability of PfTop1 (S1)-(S5) to be circularized by pfTop1 or hTop1 was tested in the REEAD setup (FIG. 21 c) by incubation one at a time with each of the purified enzymes, followed by solid-support RCA of closed circles as previously described by Stougaard, M. et al. ACS Nano 3, 223-233 (2009). RCPs were visualized microscopically at the single-molecule level upon hybridization of red-fluorescent probes. To allow comparative quantification of signals generated in different reactions, a known concentration of control-circle with a unique probe-annealing sequence was added to the reaction mixtures before RCA and resulting RCPs visualized using a green-fluorescent probe. Estimating the circularization efficiency of pfTop1 (S1)-(S5) by pfTop1 in terms of frequency of red signals relative to green signals demonstrated pfTop1(S1) to be the most efficient sensor of pfTop1 (FIGS. 21 d and e). Hence, pfTop1(S1) was chosen for the following experiments. None of the oligonucleotides were circularized by hTop1 (FIG. 21d, and data not shown).

Figure 22:
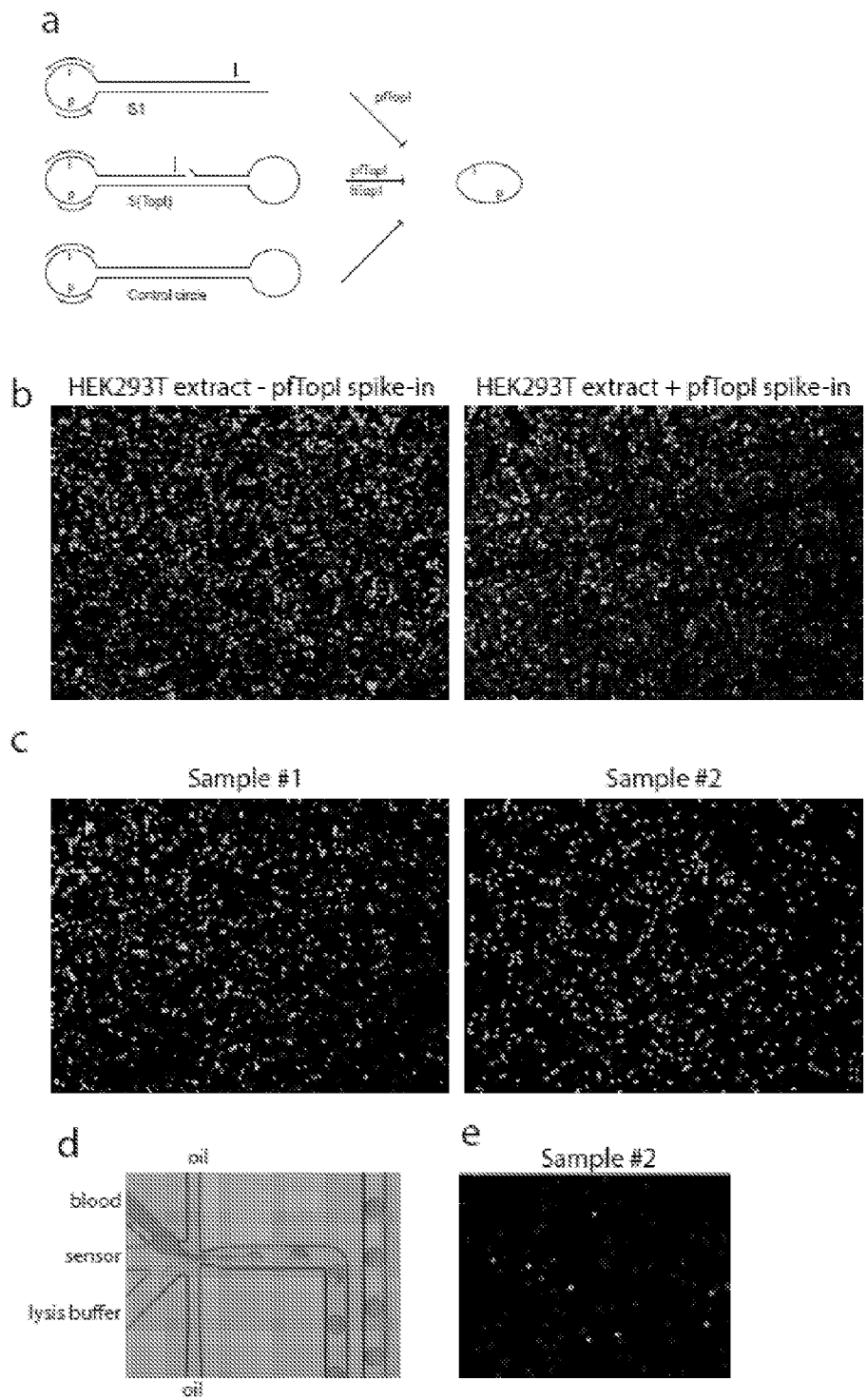
FIG. 22. REEAD of pfTopl in crude biological samples. a, Illustration of the nucleotide sensors used in the experiments shown in b, c, and e. b, microscopic view showing the result of REEAD analyses of nuclear extracts from HEK293T cells without (left panel) or with purified pfTopl spike-in (right panel) using the sensors shown in a. c, same as b except that extracts from blood from an uninfected (Sample #1, left panel) or pauci-parasitic malaria patient (Sample #2, right panel) were analyzed, d, shows a light-microscopic view of the microfluidic platform. Blood sample #2, nucleotide sensors and lysis buffer was loaded into three different channels in aqueous solution and by competition with oil confined in pL droplets in which the reaction took place. Mixing of droplet content was ensured by the serpentine channel of the device, e, is an example of a microscopic view obtained when analysing 200 pL of unprocessed sample #2 in the integrated REEAD-microfluidic channel setup. RCPs originating from circularized S1, S(Topl) and control circle were visualized by hybridization of rhodamine-(red), FITC-(green), Cy5-(blue) labeled fluorescent probes, respectively.
Figure 25:
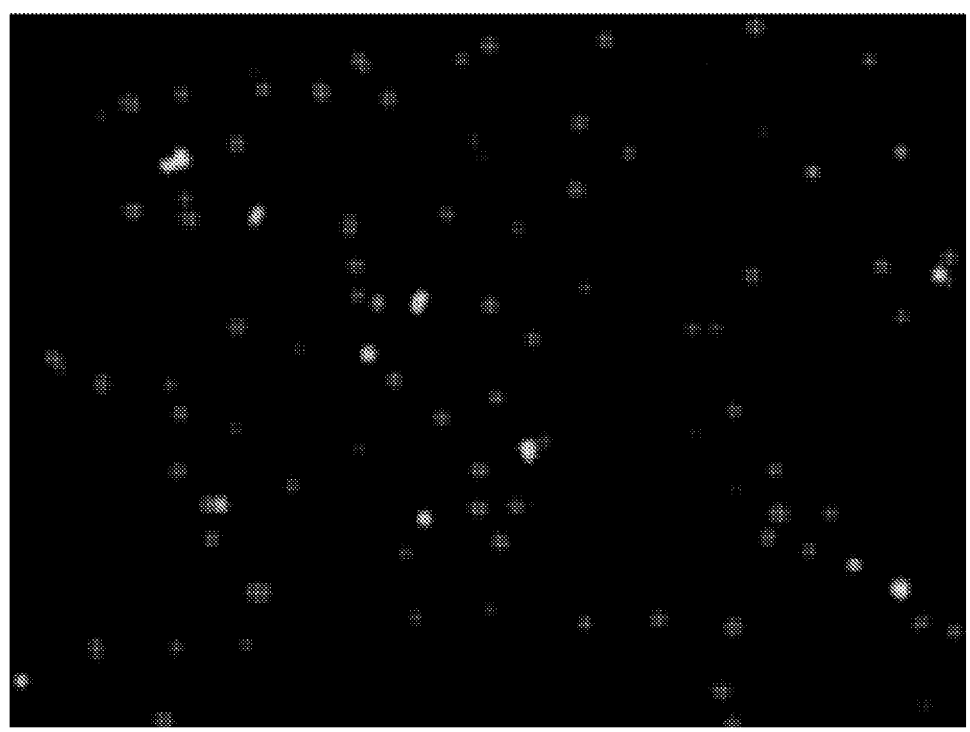
FIG. 25. Circularization of S(TopI) by pfTopI. To investigate if pfTopI could react with and circularize the REEAD sensor S(TopI) previously demonstrated to react specifically with hTopI in human cell extract, purified recombinant pfTopI were incubated with S(TopI) and the result analyzed according to the REEAD protocol. As a positive control, control-circle was added to the reaction mixture before RCA. The microscopic image shows the result of incubating purified pfTopI with S(TopI) followed by solid support RCA and visualization of resulting RCPs by hybridization to a rhodamine-(red) labeled probe. RCPs resulting from RCA of control-circles added to the reaction mixture were visualized by hybridization to a FITC-(green) labeled probe.

The specificity of pfTop1(S1) for pfTop1 in crude biological samples was addressed using nuclear extract from human HEK293T cells with or without spike-in pfTop1 as a model for Plasmodium infection. Besides pfTop1(S1), S(Top1), previously demonstrated to sense specifically hTop1 in crude cell extracts, and control-circle was added to the reaction mixtures as positive controls for nuclear extraction and RCA/probe hybridization, respectively (FIG. 22a). Red/dark signals corresponding to single RCPs matching circularized pfTop1(S1) was observed only upon addition of pfTop1 spike-in, whereas green and blue signals originating from circularized S(Top1) and control-circle, respectively, were observed in both samples (FIG. 22b). This demonstrates the specificity of pfTop1(S1) for pfTop1 even on a background of human nucleus content. Note, due to characteristics shared between hTop1 and pfTop1, the latter enzyme circularizes S(Top1) (FIG. 25) as well as pfTop1(S1). Consequently, green signals observed in FIG. 22b, right panel, originated from hTop1 and pfTop1 activity in combination where pfTop1 (S1) and S(Top1) competed for reaction by pfTop1 at the expense of sensitivity.

To address the performance of pfTop1-specific REEAD in sensing Plasmodium in clinically relevant samples, pfTop1 (S1) and S(Top1) were reacted with extracts prepared from blood samples from an uninfected (sample #1) or a P. fa/c/pa/i m-infected patient (sample #2). Control-circle was added to the reaction mixtures as a positive control. Color codes were the same as in FIG. 22b. As evident from FIG. 22c, red/dark pfTop1-specific signals were observed only upon incubation of the REEAD sensors with extracts from sample #2, while green and blue signals were observed after incubation with both extracts. Sample #2 originated from a pauci-parasitic patient with a parasitemia below 0.0001-0.0004% representing the detection limit of traditional microscopy-based diagnosis, although detectable by PCR (data not shown). Hence, even in the presented crude setup, the REEAD assay performed better than state-of-the-art diagnostic assays with regard to sensitivity. Testing samples from several uninfected or pauci-parasitic patients confirmed generality of the results shown in FIG. 22c (data not shown).

Figure 26:
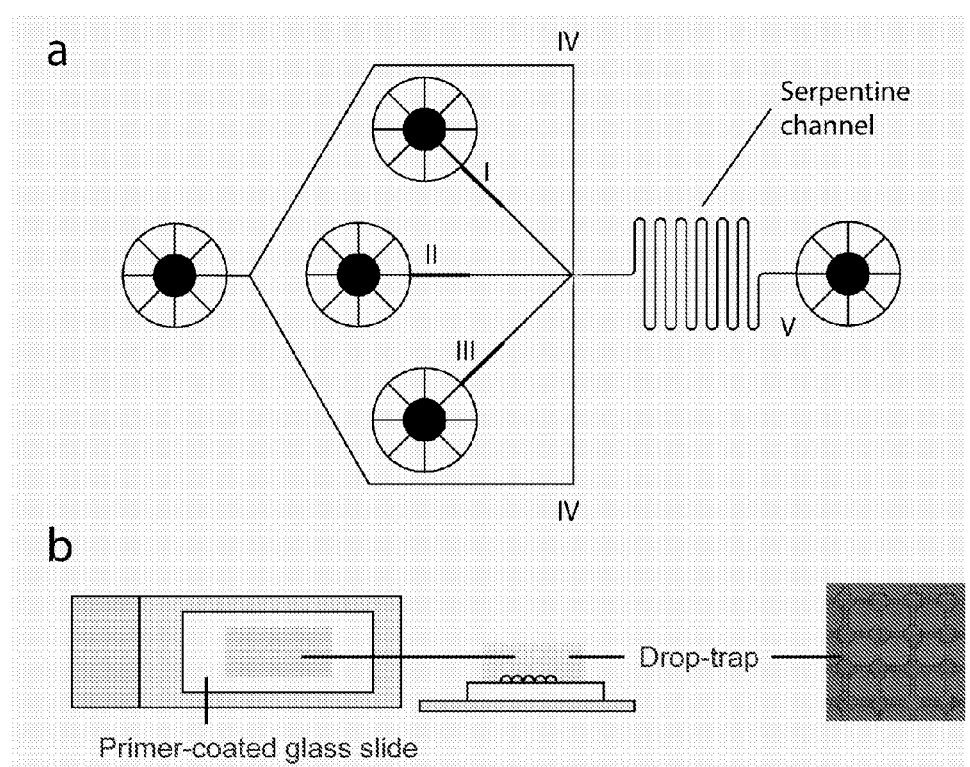
FIG. 26. The microfluidic lab-on-a-chip device, a, schematic illustration of the microfluidic channel device. In the microfluidic channel device, three merged aqueous streams containing blood cells, nucleotide sensors or low-salt lysis buffer are broken up by an oil stream to form a stable water-in-oil emulsion. The components confined in the aqueous picoliter droplets are lead through a serpentine channel to ensure adequate content mixing and reactions can subsequently take place within the droplets. Blood cells to be analyzed, lysis buffer and pfTopI(S1), S(TopI) and control-circle were fed to the system in three different channels (marked I, II, and III). By competition with oil (fed by channel IV) the three different components were confined in pL droplets, lead via a channel system to the outlet (V) and subsequently confined in the drop-trap device. The serpentine channel ensuring mixing of droplet content is indicated on the figure, b, shows the drop-trap device. Droplets were confined in cavities at the intersections in the drop-trap (right panel), and exsiccated onto a primer-coated glass slide (left and middle panel) to support RCA.

The need for extensive sample preparation poses an obstacle for the practical use of diagnostic tests. In the experiments shown in FIG. 22c, extracts were prepared from 10 mL of blood in a procedure involving several centrifugations. To investigate if such preparation could be avoided, REEAD was combined with a simple microfluidic channel lab-on-a-chip device (Cho, E. J., Yang, L, Levy, M. & Ellington, A. D. Using a deoxyribozyme ligase and rolling circle amplification to detect a non-nucleic acid analyte, ATP. J Am Chem Soc 127, 2022-2023 (2005)) allowing confinement of infected blood cells, biosensors, control-circle and low-salt lysis buffer in pL droplets in which the reaction took place (FIG. 22d and FIG. 26). Subsequently, droplets were retained in a drop-trap and exsiccated on a primer-coated glass slide to support RCA and visualization of RCPs. Using this integrated setup is was possible to detect P. falciparum infection using only 200 µL of completely unprocessed blood sample #2 (FIG. 22e).

Figure 27:
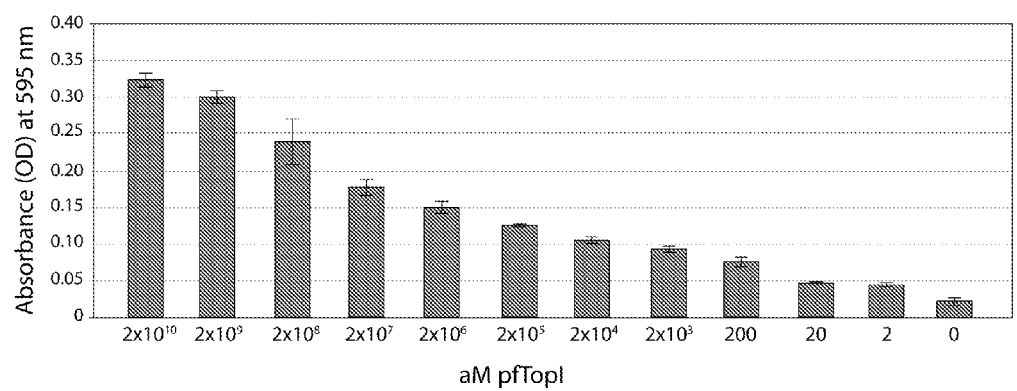
FIG. 27. The detection limit of REEAD combined with HRP colorimetric readout. The chart diagram shows the spectrophotometric readings obtained in three individual experiments measuring the activity of decreasing concentrations of purified recombinant pfTopI in REEAD using the HRP-mediated colorimetric readout.

To investigate if the Plasmodium-spec\f c REEAD could be adapted to simple colorimetric readout, suitable for low-resource settings without compromising sensitivity, an additional enzymatic step was introduced to the assay by coupling streptavidin-fused HRP to biotinylated RCPs as described by Yan, J. et al. An on-nanoparticle rolling-circle amplification platform for ultrasensitive protein detection in biological fluids. Small 6, 2520-2525 (2010). HRP oxidizes colorless tetramethylbenzidine to a blue-colored form, detectable to the naked eye or by spectrophotometric measurements. This, of course, is at the expense of the possibility of multiplexing since RCPs originating from different circles cannot be distinguished. Hence, S(Top1) and control-circles used as internal controls for microscopic readout had to be omitted and replaced with separate control experiments for the colorimetric readout. This, however, imposed the advantage of preventing competition between S(Top1) and pfTop1(S1) for pfTop1, as discussed above. The two readout formats were compared by reacting pfTop1(S1) with increasing dilutions of extracts from blood sample #2 followed by microscopic visualization of RCPs or by spectrophotometric measurement of HRP substrate conversion. As evident from FIG. 23 colorimetric readout increased sensitivity of REEAD by a factor two compared to microscopic readout. When using purifed pfTopl to circularize S1, the HRP reaction allowed direct visual detection of 200 aM of pfTopl (data not shown) whereas spectrophotometric measurement allowed detection of 2 aM pfTopl (FIG. 27).

In conclusion the pfTopl-specific REEAD setup presented here allowed the highly sensitive detection of *Plasmodium* infection in even small volumes of unprocessed blood samples. The presented assay out-competes current state-of-the-art malaria diagnostic assays with regard to sensitivity, time-of-performance and ease of the procedure. Thus, REEAD can form the basis for novel user-friendly and low-cost kits for first-line detection of malaria, which may be of particular importance in low-resource settings. Compared to most published RCA-based systems for detection of nucleotide sequences or non-reactive proteins, the specific detection of an enzyme activity presents the advantage of being suitable for solution detection, requiring little sample preparation and including an inherent initial enzymatic amplification step. The presented *Plasmodium*-spec\f\c REEAD is an important proof-of-principle for the usability of enzyme-specific biomarkers in diagnostics. Moreover, pfTopl is a potential target for new drugs in the combat against multi-drug resistant malaria, and therefore, the presented REEAD provide an important mean for fast high-throughput drug screening setups in a method for drug discovery according to the present invention.

Methods Nucleotide sensors, primers and probes: All oligonucleotides were purchased from DNA Technology A/S. The sequences of the oligonucleotides are shown in Supplementary Information. Enzyme expression and purification: The pfTopl gene (PlasmoDB accession number PFE0520c)[23] was codon optimized (by GeneArt) for expression in *Saccharomyces cerevisiae*. The optimized gene was PCR amplified and cloned into the pYES2.1N5-His-TOPO vector (Invitrogen). A positives clone was identified by sequencing and the plasmid pPFTIOO was transformed into the yeast *S. cerevisiae* toplA strain RS190 (a kind gift from R. Sternglanz, State University of New York, USA) according to standard procedures. pfTopl was expressed and purified as previously described for human topoisomerasel[24]. hTopl was expressed and purified as previously described[24]. The protein concentrations were estimated from Coomassie blue-stained SDS-polyacrylamide gels by comparison to serial dilutions of BSA.

Cell culture and nuclear extract preparation: Human embryonic kidney HEK293T cells were cultured in Dulbecco's Modified Eagle Medium (GIBCO) supplemented with 10% fetal bovine serum (FBS) (GIBCO), 100 units/mL penicillin and 100 mg/mL streptomycin (Invitrogen). Cells were incubated in a humidified incubator (5% $CO_2$/95% air atmosphere at 37° C.). Cells were harvested with 0.5% Trypsin-EDTA (GIBCO).

Media was discarded and the cell washed in Phosphate-Buffered Saline (1×PBS) prior to nuclear extraction performed as previously described'. The cell extracts were used for REEAD directly or spiked with purified pfTopl prior to REEAD. Preparation of extracts from blood samples: 30 ml_ RBC lysis buffer (Gentra Puregene) was added to 10 mL of blood (uninfected or P. fa/c/pa/x m-infected) harvested in heparin tubes. After mixing and incubation for 5 min. at room temperature (RT), cells, including *Plasmodium* parasites, were pelleted by centrifugation at 3500 rpm for 30 min at RT. The cell pellet was washed with 1×PBS containing 1 mM DTT and 0.1 mM PMSF and resuspended in 2× pellet-volume of nuclear extraction buffer (0.5 M NaCI; 20 mM HEPES, pH 7.9; 20% glycerol; 1 mM DTT and 0.1 mM PMSF). Cells and parasites were disrupted by repeated passage through a gauge-G25 syringe. Nuclear content was extracted from the disrupted cells and parasites by rotating for 1 hr. at 4° C. and cell debris spun down at 14.000 rpm for 10 min. at 4° C. The supernatant was collected and used for REEAD. Enzyme mediated circularization of oligonucleotide sensors: Circularization reactions were carried out in 30 μL reaction volumes containing a divalent cation depletion buffer (1 mM Tris-HCl, pH 7.5; 5 mM EDTA) supplemented with 100 nM oligonucleotide sensor(s) as stated in the text. Reactions were initiated by the addition of the purified enzymes (hTopl or pfTopl) and/or cell extracts as described in the text. Incubation was carried out for 30 min at 37° C. before heat inactivating the enzyme(s) for 5 min at 95° C. Samples were exonuclease digested by supplementing the reactions with 7 units exonuclease I (Fermentas) and 70 units exonuclease III (Fermentas) and incubating for 60 min at 37° C., followed by inactivation for 15 min at 80° C.

REEAD-microscopic readout: The 5'-amine-conjugated primer was coupled to CodeLink Activated Slides (SurModics) according to the manufacturer's description. 5 ul circularization reaction sample (supplemented with 100 nM control-circle when stated in the text) was hybridized to the immobilized primers by incubation for 60 min. at RT (22-25° C.). RCA and microscopic visualization were performed as previously described[1,7]. Quantification of pfTopl specific signals was performed as previously described[1]. REEAD-HRP readout: Primer coupling to NHS-activated M-PVA Akl 1 magnetic beads (Chemagen) was performed according to the manufacturer's description. Briefly, 100 μM amine-conjugated primer was incubated with 1.5 μg magnetic beads in 1× coupling buffer (0.05 M HEPES, pH 7.8) for 12 hrs at 4° C. The coupling reaction was quenched by the addition of quenching solution (0.05 M Tris and 0.1% ethanolamine, pH 8.0) followed by incubation for 1 hr at RT. For HRP-mediated detection of pfTopl specific circles, 10 ul circularization reaction sample was hybridized to 15 ng primer-coupled magnetic beads in hybridization buffer (Phi29 polymerase buffer (Fermentas) supplemented with 200 mM NaCI) for 1 hr at RT (22-25° C.). RCA mixture (2 μL of biotin-dNTP mix (mixture of 0.25 mM biotin-dATP and 0.75 mM dATP and 1 mM of other dNTPs), 2 μL of Phi29 buffer (10×) and 2 μL of Phi29 polymerase (Fermentas)) was added to the beads and RCA was carried out at 30° C. for 30 min. followed by further incubation at 37° C. for 3 hrs. Urea unfolding of the RCPs, RCP coupling of avidin-HRP (Sigma-Aldrich) and colorimetric detection (TMB substrate was from Neogen) were performed as previously described[16]. REEAD in unprocessed blood samples in microfluidic system. The microfluidic setup consists of two devices: a flow-focusing droplet generator and a drop-trap. Both devices were fabricated by conventional soft lithography techniques[25], casting and curing the PDMS prepolymer on a SU-8 3025 (MicroChem) master of a channel height at around 25μηι. PDMS prepolymer (Sylgard 184) was prepared in a 10:1 (base:curing agent) ratio and cured at 65° C. for 1 hr. Prior to the experiments, the channel was wetted with oil/surfactant (EA Surfactant, RainDance) for at least 15 min. Two syringe pumps (Harvard Apparatus) were used to control the flow rates of oil/surfactant and reagents independently, forming monodisperse water-in-oil droplets at a frequency of 0.8-1.5 kHz. The droplet volume and generation frequency was controlled by the flow rate ratio, determined by the competition between continuous phase (carrier fluid (FC-40 fluorocarbon oil (3M): the oil/surfactant, flow rate 22.5 μL_Aη\iη) and disperse phase (aqueous reagents: blood, lysis buffer and sensors, flow rate 2.5 μL_Aη\iη). Blood, lysis buffer (10 mM Tris-HCL pH 7.5, 0.5 mM EDTA, 1 mM DTT, 1 mM PMSF, 0.2% Tween 20), and sensors (final sensor concentration in the droplets: S(hTop1): 67 mM, S1: 167 mM, control-circle: 33 mM) were loaded in each their channel in the microfluidic device and droplet generation initiated. The generated droplets were harvested in eppendorf tubes and placed on a primer-printed glass slide prepared as described above. The PDMS drop-trap was gently placed on top of the glass slide. The geometry of the drop-trap was designed according to the size of generated droplets. The droplets were left to exsiccate for 16 hours. Wash, RCA, and hybridization of probes were performed as previously described by Nallur, G. et al. Nucleic Acids Res 29, E1 18 (2001).

```
                            Sequences

SEQ ID NO: 1.
Mycobacterium tuberculosis topoisomerase I gene:
TTGGCTGACCCGAAAACGAAGGGCCGTGGCAGCGGCGGCAATGGCAGCGGCCG
GCGACTGGTCATCGTCGAGTCGCCCACCAAGGCGCGCAAGCTGGCCTCCTACCTG
GGCTCTGGCTACATCGTCGAGTCCTCCCGGGGGCACATCCGTGACTTGCCGCGGG
CCGCGTCGGATGTACCCGCAAAGTACAAGTCGCAGCCGTGGGCGCGGCTCGGGG
TCAACGTCGACGCCGACTTCGAACCGCTCTACATCATCAGCCCGGAGAAACGGA
GCACCGTCAGCGAGCTCAGGGGCCTGCTCAAAGACGTGGACGAGCTGTATCTGG
CCACGGATGGGGACCGTGAGGGCGAAGCTATTGCCTGGCATCTGCTGGAAACCC
TCAAACCGCGCATACCGGTAAAGCGGATGGTCTTCCACGAGATCACCGAACCGG
CGATCCGCGCCGCCGCCGAGCACCCCGCGACCTAGACATCGACCTGGTCGACG
CGCAGGAGACCCGGCGCATCCTGGACCGGCTGTACGGCTACGAAGTCAGCCCAG
TGCTGTGGAAGAAGGTCGCCCCCAAGTTGTCGGCGGGCCGGGTGCAGTCGGTGG
CCACCCGCATCATCGTGGCGCGCGAACGCGACCGCATGGCGTTCCGCAGCGCGG
CCTACTGGGACATCCTTGCCAAGCTGGATGCCAGCGTGTCCGACCCGGACGCCGC
GCCGCCCACCTTCAGCGCCCGGCTGACGGCCGTGGCTGGCCGGCGGGTGGCCAC
TGGCCGCGATTTCGACTCGCTGGGCACGCTGCGCAAAGGCGACGAAGTCATTGT
GCTCGACGAGGGGAGCGCGACCGCGTTGGCCGCGGGCCTGGATGGCACGCAGCT
GACCGTGGCCTCGGCCGAGGAGAAGCCCTACGCCCGGCGCCCGTACCCGCCGTT
CATGACCTCCACGCTGCAGCAAGAGGCCAGCCGCAAGCTGCGGTTCTCCGCCGA
GCGGACGATGAGCATCGCCCAGCGGCTGTACGAAAACGGCTACATCACCTATAT
GCGTACCGACTCCACCACGCTGTCGGAGTCGGCGATCAACGCCGCACGTACCCA
GGCGCGCCAGCTCTACGGCGACGAGTACGTCGCGCCGGCGCCGCGCCAATACAC
CCGCAAGGTGAAGAACGCCCAGGAAGCGCACGAGGCTATCCGGCCCGCCGGTGA
AACGTTTGCCACCCCGGACGCGGTGCGTCGCGAACTCGACGGTCCCAACATTGAT
GATTTCCGGCTCTATGAGCTGATTTGGCAACGCACCGTAGCCTCGCAGATGGCCG
ATGCGCGGGGCATGACGCTGAGCCTGCGGATCACTGGCATGTCGGGGCACCAGG
AGGTGGTGTTCTCCGCGACCGGACGCACCTTGACGTTCCCGGGCTTCCTCAAGGC
CTACGTGGAGACCGTGGACGAGCTGGTCGGCGGCGAGGCTGACGATGCCGAGCG
GCGACTGCCCCATCTGACCCCGGGTCAACGGTTGGACATCGTCGAGTTGACCCCA
GACGGCCATGCCACCAACCCGCCGGCCCGCTACACCGAGGCGTCGCTGGTCAAA
GCGCTCGAGGGAGCTGGGCATCGGCCGCCCGTCGACCTACTCGTCGATCATCAAG
ACCATCCAGGATCGCGGCTACGTGCACAAGAAGGGCAGTGCACTGGTGCCGTCA
TGGGTGGCGTTCGCGGTAACCGGTCTGCTCGAGCAGCATTTCGGTCGGCTCGTCG
ACTACGACTTCACCGCGGCGATGGAAGACGAGCTCGACGAGATCGCCGCCGGCA
ACGAGCGCCGCACCAACTGGCTCAACAACTTCTACTTTGGTGGCGATCACGGTGT
GCCCGATTCGGTAGCCCGATCGGGTGGCCTCAAGAAGCTTGTCGGGATCAATCTC
GAGGGCATCGACGCACGAGAAGTAAACTCTATCAAGCTTTTTGACGACACCCAC
GGACGCCCCATATATGTTCGGGTGGGCAAGAACGGTCCCTACCTGGAACGTTTG
GTGGCCGGCGACACCGGTGAGCCCACGCCGCAGCGGGCCAACCTCAGCGACTCG
ATTACCCCGGACGAGCTGACTCTACAGGTGGCCGAAGAGCTCTTTGCCACACCGC
AACAGGGACGGACTTTGGGCTTGGACCCAGAAACCGGCCACGAGATCGTGGCCA
GGGAAGGCCGGTTTGGGCCGTATGTGACCGAGATCCTGCCGGAGCCTGCGGCTG
ATGCGGCCGCGGCCGCTCAGGGAGTCAAGAAACGCCAGAAGGCCGCCGGGCCC
AAACCGCGCACCGGTTCGTTGCTGCGGAGCATGACCTACAGACGGTCACCCTC
GAAGACGCGCTGAGGCTGCTGTCACTGCCGCGCGTGGTCGGAGTGGACCCCGCC
TCGGGTGAGGAGATCACCGCGCAGAACGGGCGCTACGGACCGTATCTAAAGCGC
GGCAACGATTCTCGATCACTGGTCACCGAAGACCAGATATTCACCATCACGCTCG
ACGAAGCCCTGAAGATCTACGCAGAGCCGAAACGTCGTGGCCGGCAAAGCGCTT
CGGCTCCGCCGCTGCGCGAGCTGGGAACAGATCCGGCGTCGGGCAAGCCAATGG
TCATCAAGGACGGCCGATTCGGGCCGTACGTCACCGACGGTGAGACCAATGCCA
GCCTGCGTAAGGGCGACGACGTGGCTTCCATAACCGACGAGCGCGCCGCCGAGC
TGTTGGCCGATCGCCGAGCCCGGGGTCCGGCAAAACGGCCAGCCAGGAAAGCTG
CCCGGAAGGTGCCGGCGAAGAAGGCAGCCAAGCGCGACTAG SEQ ID NO: 2.
Mycobacterium tuberculosis topoisomerase I protein:
MADPKTKGRGSGGNGSGRRLVIVESPTKARKLASYLGSGYIVESSRGHIRDLPRAAS
DVPAKYKSQPWARLGVNVDADFEPLYIISPEKRSTVSELRGLLKDVDELYLATDGDR
EGEAIAWHLLETLKPRIPVKRMVFHEITEPAIRAAAEHPRDLDIDLVDAQETRRILDRL
YGYEVSPVLWKKVAPKLSAGRVQSVATRIIVARERDRMAFRSAAYWDILAKLDASV
SDPDAAPPTFSARLTAVAGRRVATGRDFDSLGTLRKGDEVIVLDEGSATALAAGLDG
TQLTVASAEEKPYARRPYPPFMTSTLQQEASRKLRFSAERTMSIAQRLYENGYITYM
RTDSTTLSESAINAARTQARQLYGDEYVAPAPRQYTRKVKNAQEAHEAIRPAGETFA
TPDAVRRELDGPNIDDFRLYELIWQRTVASQMADARGMTLSLRITGMSGHQEVVFS
ATGRTLTFPGFLKAYVETVDELVGGEADDAERRLPHLTPGQRLDIVELTPDGHATNP
```

```
PARYTEASLVKALEELGIGRPSTYSSIIKTIQDRGYVHKKGSALVPSWVAFAVTGLLE
QHFGRLVDYDFTAAMEDELDEIAAGNERRTNWLNNFYFGGDHGVPDSVARSGGLK
KLVGINLEGIDAREVNSIKLFDDTHGRPIYVRVGKNGPYLERLVAGDTGEPTPQRAN
LSDSITPDELTLQVAEELFATPQQGRTLGLDPETGHEIVAREGRFGPYVTEILPEPAAD
AAAAAQGVKKRQKAAGPKPRTGSLLRSMDLQTVTLEDALRLLSLPRVVGVDPASGE
EITAQNGRYGPYLKRGNDSRSLVTEDQIFTITLDEALKIYAEPKRRGRQSASAPPLREL
GTDPASGKPMVIKDGRFGPYVTDGETNASLRKGDDVASITDERAAELLADRRARGP
AKRPARKAARKVPAKKAAKRD

P.F. TopI
For information, cf:
http://www.ncbi.nlm.nih.gov/gene/812833

SEQ ID NO: 3.
Plasmodium falciparum Gene sequence (ACCESSION NC_004326):
http://www.ncbi.nlm.nih.gov/nuccore/NC_004326?report = genbank &
from = 445981 & to = 448500 & strand = true
    1 atgcaatcaa tggaaataaa tgataataac agtatcaaga atgaaagtac atctgatgat
   61 gatatattaa ttaataaaat taaacaaaac ttgggtaata taaatcatg taattctaga
  121 tcttccaaaa aggaatctat aaaaaagcaa aagagcaatt ctgaacttgg tataaaaaag
  181 aacacaaaga aatcattagg tataaaaaaa gaggaagaaa aaaaaaaaca aataagcaaa
  241 agaaaaagta atgaactaaa agaaaaaaat aatttgaaag agggaaaaaa gaaatatgtg
  301 gaaaaaaaat ctagaacagt aaaagatgaa accaagttaa cgaatgttat aaaaaaagaa
  361 actcaaaata ataagaaacc taaaaaatta cttaaaaaat cagaagaaaa ttttgaacca
  421 ataatagat ggtgggaaaa aatagatgat caaacagata tacaatggaa ttatttagaa
  481 catcgaggat taatattttc ccctccatac gttcaacatc atgtaccaat tttttataaa
  541 agtataaaaa ttgaattaaa tgcaaaatca gaagaattag ctacctattg gtgtagtgca
  601 attggtagtg attattgtac aaaagaaaag tttatattaa attttttaa aacatttata
  661 aatagtttag aaaatgataa tattataaaa caagagaatg aaacgaaatt aaaaaaagga
  721 gatatatcta attttaagtt tattgatttt atgccaatca aagatcattt attaaaatta
  781 agagaagaaa agttaaataa aacaaagaa gaaaagaag aggaaaaaaa aatgagaatg
  841 gaaaaagaat taccatatac atatgcgtta gttgattgga ttcgtgaaaa gatatcaagt
  901 aataaagcag aaccacctgg gttatttaga ggaagaggaa aacatccaaa acaaggttta
  961 ttaaaaaaaa gaattttttcc agaagatgtt gtaattaata ttagtaaaga tgcacctgta
 1021 ccacgattat atgataatat gtgtggacat aattggggtg atatatatca tgataataaa
 1081 gtaacatggt tagcttatta taaagatagt ataaatgatc aaataaaata tactifitta
 1141 tctgctcaat caaaatttaa aggatataaa gatcttatga aatatgaaaa tgctcgaaaa
 1201 ttaaaatcat gtgttcataa aattagggaa gattataaaa ataaaatgaa aaataaaaat
 1261 attattgata aacaattagg aacagctgtt tatttaatag attttctagc attaagagta
 1321 ggaggagaaa aagatatcga tgaagaagca gatactgtag gttgttgtag tttaagagta
 1381 gaacatatta gttttgcaca cgatataccc ttcaaaagtg tagattcaaa agaacaaaaa
 1441 acaaatgatg aaaaagaaaa taaaatacca ttaccaacaa atttagaaag tatttcatca
 1501 gaagattgtt atataacttt agatttttta ggaaaagata gtatacgata ttttaataca
 1561 gtcaaaatag ataaacaagc atatattaat ataatatat tttgtaaaaa taaaaataga
 1621 gatgaaggag tttttgatca aatacttgt tcaaaattaa atgaatatct aaaagaaatt
 1681 atgcctactt tatcagctaa agtgtttcgt acatataatg cttcaattac attagatcaa
 1741 caattaaaaa gaataaaaga agtttatgga aaaacaacat attcattata ttctggtgaa
 1801 acagaattac acaaatcgaa aaaaagaaaa tctagccatt taacttcaga tacaaatata
 1861 ttaagtgatg caagtgattc tactattaat gatgtaaata acgagtatga tgaaaatgga
 1921 ataaataaaa aactatcata tgctactact gtaggaaaag aaaatgatgt cgatgataaa
 1981 aactccaccaa tagaagttga cgtttcaaat ataaatgaac ttattaattt ttacaataat
 2041 gcaaatagag aagtagccat attatgtaac catcaaagaa gtattccaaa acaacatgat
 2101 acaactatgt caaaaataaa aaaacaaatt gaattatata tgaagatat aaaagaatat
 2161 aaaaaatatt tgcaacattt aaaaaaaaat agtgataaaa aatttatctt tgtttcgaaa
 2221 gtttctactt tagatggaac tttaagacca aataagtca aagaaaatat gaaagaagaa
 2281 tcttgtaaaa aaaaactaat tactcttata aaaaagttg aattattaaa taaccaaatg
 2341 aaagtaagag atgataataa aactattgct ttaggtacat ctaaaattaa ttatatggat
 2401 ccaagaataa ctgttgcttt ttgtaaaaaa tttgaaatac ccatagaaaa agtatttaat
 2461 agaagtttaa gacttaaatt tccttgggcc atgtttgcta caaaaaattt tacatttta
//

SEQ ID NO: 4.
Plasmodium falciparum Protein sequence (ACCESSION XP_001351663):
http://www.ncbi.nlm.nih.gov/protein/XP_001351663.1
    1 mqsmeindnn siknestsdd dilinkikqn lgnnkscnsr sskkesikkq ksnselgikk
   61 ntkkslgikk eeekkkqisk rksnelkekn nlkegkkkyv ekksrtvkde tkltnvikke
  121 tqnnkkpkkl lkkseeenfep inrwekidd qtdiqwnyle hrglifsppy vqhhvpifyk
  181 sikielnaks eelatywcsa igsdyctkek filnffktfi nslendniik qenetklkkg
  241 disnfkfidf mpikdhllkl reeklnktke ekeeekkmrm ekelpytyal vdwirekiss
  301 nkaeppglfr grgehpkqgl lkkrifpedv viniskdapv prlydnmcgh nwgdiyhdnk
  361 vtwlayykds indqikytfl saqskfkgyk dlmkyenark lkscvhkire dyknkmknkn
  421 iidkqlgtav ylidflalrv ggekdideea dtvgccslrv ehisfandip fksvdskeqk
  481 tndekvnkip lptnlesiss edcyitldfl gkdsiryfnt vkidkqayin iiifcknknr
  541 degvfdqitc sklneylkei mptlsakvfr tynasitldq qlrikevyg kttyslysge
  601 telhkskkrk sshltsdtni lsdasdstin dvnneydeng inkklsyatt vgkendvddk
  661 nspievdvsn inelinfynn anrevailcn hqrsipkqhd ttmskikkqi elynedikey
```

-continued

| Sequences |
|---|

```
721 kkylqhlkkn sdkkfifvsk vstldgtlrp nkvkenmkee sckkklitli kkvellnnqm
781 kvrddnktia lgtskinymd pritvafckk feipiekvfn rslrlkfpwa mfatknftf
```

Substrates:
M.T. TopI
SEQ ID NO: 5.
*Mycobacterium tuberculosis* substrate
TbSub-ID33
5'p-CAGAGTGCGCAGTTGG-CCTCAATGCACATGTTTGGCTCC-
GAGCGAGCTTCCGCT-tgacatcccaata-3'

SEQ ID NO: 6.
*Mycobacterium tuberculosis* substrate
TbSub-ID3 3
5'p-CAGAGTGCGCAGTTGG-tctct-CCTCAATGCACATGTTTGGCTCC-tctct-
GAGCGAGCTTCCGCT-tgacatcccaata-3'

SEQ ID NO: 7.
*Mycobacterium tuberculosis* topoisomerase I target
CGCTtg

P.F. TopI
SEQ ID NO: 8.
*Plasmodium falciparum* substrate
Tp-Id33
5'-TCTAGAAAGTATAGGAACTTCGAACGACTCAGAATG-
ACTGTGAAGATCGCTTAT-CCTCAATGCACATGTTTGGCTCC-
CATTCTGAGTCGTTCGAAGTTCCTATACTTT-3'

SEQ ID NO: 9.
*Plasmodium falciparum* substrate
sub Tp-IdS3
5'-CATACATTATACGAAGTTATGAGCGTCTGAGTATG-
ACTGTGAAGATCGCTTAT-CAGTGAATGCGAGTCCgTCTACT-
CATACTCAGACGCTCATAACTTCGTATAATGT-3'

SEQ ID NO: 10.
*Plasmodium falciparum* substrate
PF-subs-TopI primer, may have 3'-amine, ID16
5'-ATTTTTAA-ACTGTGAAGATCGCTTAT-TTAAAAATTTTTCTAAGTCTTTTTTCC-
CCTCAATGCTGCTGCTGTACTAC-GAAAAAAGACTTAGAAAAAT-3'

SEQ ID NO: 11.
*Plasmodium falciparum* substrate
PF-subs-ver1-TopI primer
5'-ATTATAATTTTTTGGAACTTCGAACGACTCAGAATG-
ACTGTGAAGATCGCTTAT-CCTCAATGCACATGTTTGGCTCC-
CATTCTGAGTCGTTCGAAGTTCCAAAAAATT-3'

SEQ ID NO: 12.
*Plasmodium falciparum* substrate
PF-subs-ver2-TopI primer
5'-TTATAATTTTTTGGAACTTCGAACGACTCAGAATG-ACTGTGAAGATCGCTTAT-
CCTCAATGCACATGTTTGGCTCC-CATTCTGAGTCGTTCGAAGTTCCAAAAAATT-
3'

SEQ ID NO: 13.
*Plasmodium falciparum* substrate
PF-subs-ver5-TopI primer
5'-TTTATAAAGTATAGGAACTTCGAACGACTCAGAATG-
ACTGTGAAGATCGCTTAT-CCTCAATGCACATGTTTGGCTCC-
CATTCTGAGTCGTTCGAAGTTCCTATACTTT SEQ ID NO: 14.
*Plasmodium falciparum* substrate
PF-subs-ver3-Flp primer ID33
5'-AAATTTTTTTGGAACTTCGAACGACTCAGAATG-AGGCTCAATCTAATGGAC-
CCTCAATGCACATGTTTGGCTCC-CATTCTGAGTCGTTCGAAGTTCCAAAAAA-3'

SEQ ID NO: 15.
*Plasmodium falciparum* substrate
PF-subs-ver4-Flp primer ID33
5'-TTTATAAAGTATAGGAACTTCGAACGACTCAGAATG-
AGGCTCAATCTAATGGAC-CCTCAATGCACATGTTTGGCTCC-
CATTCTGAGTCGTTCGAAGTTCCTATACTTT -continued Sequences SEQ ID NO: 16.
Plasmodium falciparum substrate
5'TCTAGTAAGTATAGGAACTTCGAACGACTCAGAATGACTGTGAAGATCGCTTA
TCCTCAATGCACATGTTTGGCTCCCATTCTGAGTCGTTCGAAGTTCCTATACTTA SEQ ID NO: 17.
Plasmodium falciparum substrate
5'ATTTTTCTAAGTCTTTTAGATCGAACGACTCAGAATGACTGTGAAGATCGCTTA
TCCTCAATGCACATGTTTGGCTCCCATTCTGAGTCGTTCGATCTAAAAGACTTAG
A-3'

SEQ ID NO: 18.
Plasmodium falciparum topoisomerase I target
TCTAGTAAG-(N)$_x$-CTTA, where N is A, T, C, or G, and x is between 5 and 500

SEQ ID NO: 19.
Plasmodium falciparum topoisomerase I target
ATTTTTCTA-(N)$_x$-TAGA where N is A, T, C, or G, and x is between 5 and 500

SEQ ID NO: 20.
Probe sequence
CCTCAATGCACATGTTTGGCTCC

SEQ ID NO: 21.
Probe sequence
CAGTGAATGCGAGTCCgTCTACT

SEQ ID NO: 22.
Probe sequence
CCTCAATGCTGCTGCTGTACTAC

SEQ ID NO: 23.
Primer binding sequence
ACTGTGAAGATCGCTTAT

SEQ ID NO: 24.
Primer binding sequence
AGGCTCAATCTAATGGAC

Items

The present invention specifically comprise the following items:
1. A method of identifying a microorganism in a sample, said method comprising: i. providing the sample; ii. providing a double stranded nucleic acid substrate targeted by type I topoisomerase of said microorganism; iii. mixing the sample of step i. with the nucleic acid substrate of step ii; iv. detecting nucleic acid substrate targeted by type I topoisomerase of said microorganism, wherein the presence of nucleic acid substrate targeted by type I topoisomerase of said microorganism is indicative of said microorganism.
2. The method according to item 1, wherein said microorganism is a pathogenic microorganism.
3. The method according to any of the preceding items, wherein said microorganism is *Plasmodium falciparum*, or *Mycobacterium tuberculosis*.
4. The method according to any of the preceding items, wherein said sample is blood plasma, blood serum, sputum, urine, cell smear or faeces.
5. The method according to any of the preceding items, wherein said nucleic acid substrate is specifically targeted by type I topoisomerase if said microorganism, and not by human type I topoisomerase.
6. The method according to any of the preceding items, wherein said nucleic acid substrate is a double stranded DNA substrate.
7. The method according to any of the preceding items, wherein said targeted nucleic acid substrate is detected by southern blotting, polymerase chain reaction, RT-PCR, qPCR, RFLD, primer extension, DNA array technology, rolling circle amplification.
8. The method according to any of the preceding items, wherein said targeted nucleic acid substrate is detected by rolling circle amplification.
9. A method of determining an infectious disorder in a subject, said method comprising identifying a microorganism in a sample from said subject by a method as defined in any one of items 1 to 8, wherein the presence of said microorganism in said sample is indicative of said infectious disorder.
10. An isolated nucleic acid substrate targeted by a type I topoisomerase for use as a diagnosticum for diagnosing an infectious disorder, wherein said nucleic acid substrate is targeted by a type I topoisomerase of a pathogenic microorganism associated with said infectious disorder.
11. The nucleic acid substrate according to item 10, wherein said infectious disorder is malaria or tuberculosis.
12. Use of a nucleic acid substrate targeted by a type I topoisomerase of a pathogenic microorganism for diagnosing an infectious disorder, which is associated with said infectious disorder.
13. The use according to item 12, wherein said infectious disorder is malaria or tuberculosis.

14. A kit comprising a nucleic acid substrate targeted by a type I topoisomerase of a microorganism.
15. The kit according to item 14, wherein said nucleic acid substrate is
16. A method for evaluating the effect of an agent on a microorganism in a sample, said method comprising
i. providing a sample
ii. providing a nucleic acid substrate targeted by type I topoisomerase of said microorganism,
iii. providing an agent,
iv. combining the sample of step i. and the nucleic acid substrate of step ii. with or without the agent of step iii.
v. detecting nucleic acid substrate targeted by type I topoisomerase of said microorganism with or without the agent, wherein an agent capable of reducing the amount of targeted nucleic acid substrate has an inhibitory effect on said microorganism.
17. A method of treating an infectious disorder, said method comprising administering an agent identified by a method as defined in item 16 to a subject in need thereof
18. An agent identified by a method as defined in item 16 for use in the treatment of an infectious disorder.
19. A pharmaceutical composition comprising an agent identified by a method as defined in item 16, for treating, ameliorating or preventing an infectious disorder.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method of identifying a type I topoisomerase-expressing microorganism in a sample, said method comprising:
   i) providing the sample;
   ii) providing a nucleic acid substrate targeted by a type I topoisomerase of said microorganism;
   iii) bringing the sample of step i) in contact with the nucleic acid substrate of step ii); and
   iv) detecting the nucleic acid substrate processed by said type I topoisomerase of said microorganism,
   wherein the presence of the processed nucleic acid substrate is indicative of said microorganism.

2. The method according to claim 1, wherein said microorganism is a pathogenic microorganism and/or a parasitic microorganism.

3. The method according to claim 2, wherein said microorganism is selected from the *Plasmodium* Genus.

4. The method according to claim 3, wherein said microorganism is *Plasmodium falciparum*.

5. The method according to claim 1, wherein the quantitative presence of said microorganism in said sample is determined.

6. The method according to claim 1, wherein said sample is a human sample.

7. The method according to claim 1, wherein said sample is blood plasma, blood serum, sputum, urine, cell smear, faeces, cerebrospinal fluid, or a biopsy.

8. The method according to claim 1, wherein said sample is depleted for divalent cations.

9. The method according to claim 1, wherein said nucleic acid substrate is predominantly targeted by type I topoisomerase of said microorganism and to a lesser extent by any type I topoisomerase native to said sample.

10. The method according to claim 1, wherein said nucleic acid substrate is double stranded.

11. The method according to claim 10, wherein said double stranded nucleic acid substrate is provided as a single nucleic acid, which folds into a secondary hairpin structure comprising a double-stranded target region.

12. The method according to claim 3, wherein said nucleic acid substrate comprises a sequence selected from any one of SEQ ID NO: 8-19, a sequence at least 90% identical thereto, or a part of at least 5 consecutive nucleotides of any of said sequences.

13. The method according to claim 12, wherein said nucleic acid substrate comprises the sequence TCTAGTAAG-$(N)_x$-CTTA or ATTTTTCTA-$(N)_x$-TAGA, where N is A, T, C, or G, and x is between 5 and 500 (SEQ ID NOs: 18 or 19).

14. The method according to claim 13, wherein said nucleic acid substrate comprises a sequence, with at least 90% identity to any one of SEQ ID NOs: 8-17, and which comprise the sequence TCTAGTAAG-$(N)_x$-CTTA or ATTTTTCTA-$(N)_x$-TAGA, where N is A, T, C, or G, and x is between 5 and 500 (SEQ ID NOs: 18 or 19).

15. The method according to claim 1, wherein said nucleic acid substrate is processed by cleavage and/or ligation by said type I topoisomerase.

16. The method according to claim 15, wherein said ligation is intramolecular ligation of the 3'-terminus of the nucleic acid substrate to the 5'-terminus of the nucleic acid substrate, thereby generating a circular nucleic acid product.

17. The method according to claim 16, wherein said ligation is catalyzed by said type I topoisomerase of said microorganism, by a heterogeneous ligase and/or by a recombinant ligase.

18. The method according to claim 1, wherein said processed nucleic acid substrate is detected by southern blotting, polymerase chain reaction, RT-PCR, qPCR, RFLD, primer extension, DNA array technology, a linear amplification technique, isothermal amplification and/or rolling circle amplification.

19. A method of identifying a type I topoisomerase-expressing microorganism in a sample, said method comprising:
    i) providing the sample;
    ii) providing a nucleic acid substrate targeted by a type I topoisomerase of said microorganism;
    iii) bringing the sample of step i) in contact with the nucleic acid substrate of step ii); and
    iv) detecting the nucleic acid substrate processed by said type I topoisomerase of said microorganism,
    wherein the presence of the processed nucleic acid substrate is indicative of said microorganism and said processed nucleic acid substrate is detected by rolling circle amplification.

20. The method of claim 19, wherein said nucleic acid rolling circle amplification is performed by:
    i) providing at least one oligonucleotide primer, which is capable of hybridizing to the circularized nucleic acid substrate;
    ii) hybridizing the at least one oligonucleotide primer to the circularized nucleic acid substrate;
    iii) providing a nucleic acid polymerase and nucleotides;
    iv) generating a rolling circle amplification product by extending the at least one oligonucleotide primer using the circularized nucleic acid substrate as template; and
    v) detecting the rolling circle amplification product.

21. The method according to claim 20, wherein said at least one oligonucleotide primer is selected from SEQ ID NO: 23-24.

22. The method according to claim 20, wherein said nucleic acid substrate, oligonucleotide primer, nucleic acid polymerase and/or nucleotides is immobilized on a solid support.

23. The method according to claim 22, wherein said solid support is a glass surface, a magnetic bead, a lateral flow test strip, or a dipstick.

24. The method according to claim 20, wherein one or more of said nucleotides comprises one or more detectable labels.

25. The method according to claim 24, wherein said rolling circle amplification product is detected via its incorporation of said nucleotides comprising one or more detectable labels.

26. The method according to claim 20, wherein said rolling circle amplification product is detected by hybridization of a labelled nucleic acid probe to multiple sites of the rolling circle amplification product.

27. The method according to claim 26, wherein said nucleic acid probe is labelled with one or more fluorescent dyes, radioactive nucleotides and/or biotinylated nucleotides.

28. The method according to claim 26, wherein said nucleic acid probe is coupled to an enzyme, which is capable of converting a substrate into a detectable product.

29. The method according to claim 28, wherein said enzyme is fused with streptavidin, and coupled to said nucleic acid probe via interaction with said biotinylated nucleotides incorporated in the nucleic acid probe.

30. The method according to claim 28, wherein said enzyme is horse-radish peroxidase.

* * * * *

SEQUENCE LISTING

```
<160> NUMBER OF SEQ ID NOS: 32

<210> SEQ ID NO 1
<211> LENGTH: 2805
<212> TYPE: DNA
<213> ORGANISM: Mycobacterium tuberculosis

<400> SEQUENCE: 1
ttggctgacc cgaaaacgaa gggccgtggc agcggcggca atggcagcgg ccggcgactg      60
gtcatcgtcg agtcgcccac caaggcgcgc aagctggcct cctacctggg ctctggctac     120
atcgtcgagt cctcccgggg gcacatccgt gacttgccgc gggccgcgtc ggatgtaccc     180
gcaaagtaca agtcgcagcc gtgggcgcgg ctcggggtca acgtcgacgc cgacttcgaa     240
ccgctctaca tcatcagccc ggagaaacgg agcaccgtca gcgagctcag gggcctgctc     300
aaagacgtgg acgagctgta tctggccacg gatgggacc gtgagggcga agctattgcc      360
tggcatctgc tggaaaccct caaaccgcgc ataccggtaa agcggatggt cttccacgag     420
atcaccgaac cggcgatccg cgccgccgcc gagcacccc gcgacctaga catcgacctg      480
gtcgacgcgc aggagacccg gcgcatcctg gaccggctgt acgctacga agtcagccca      540 gtgctgtgga agaaggtcgc ccccaagttg tcggcgggcc gggtgcagtc ggtggccacc     600
cgcatcatcg tggcgcgcga acgcgaccgc atggcgttcc gcagcgcggc ctactgggac     660
atccttgcca agctggatgc cagcgtgtcc gacccggacg ccgcgccgcc caccttcagc     720
gcccggctga cggccgtggc tggccggcgg gtggccactg gccgcgattt cgactcgctg     780
ggcacgctgc gcaaaggcga cgaagtcatt gtgctcgacg aggagcgc gaccgcgttg      840 gccgcgggcc tggatggcac gcagctgacc gtggcctcgg ccgaggagaa gcctacgcc      900 cggcgcccgt acccgccgtt catgacctcc acgctgcagc aagaggccag ccgcaagctg      960
cggttctccg ccgagcggac gatgagcatc gcccagcggc tgtacgaaaa cggctacatc    1020
acctatatgc gtaccgactc caccacgctg tcggagtcgg cgatcaacgc cgcacgtacc    1080
caggcgcgcc agctctacgg cgacgagtac gtcgcgccgg ccgcgcgcca atacacccgc    1140
```

-continued

```
aaggtgaaga acgcccagga agcgcacgag gctatccggc cgccggtga aacgtttgcc    1200
accccggacg cggtgcgtcg cgaactcgac ggtcccaaca ttgatgattt ccggctctat    1260
gagctgattt ggcaacgcac cgtagcctcg cagatggccg atgcgcgggg catgacgctg    1320
agcctgcgga tcactggcat gtcggggcac caggaggtgg tgttctccgc gaccggacgc    1380
accttgacgt tcccgggctt cctcaaggcc tacgtggaga ccgtggacga gctggtcggc    1440
ggcgaggctg acgatgccga gcggcgactg ccccatctga ccccgggtca acggttggac    1500
atcgtcgagt tgaccccaga cggccatgcc accaacccgc cggcccgcta caccgaggcg    1560
tcgctggtca aagcgctcga ggagctgggc atcggccgcc cgtcgaccta ctcgtcgatc    1620
atcaagacca tccaggatcg cggctacgtg cacaagaagg gcagtgcact ggtgccgtca    1680
tgggtggcgt tcgcggtaac cggtctgctc gagcagcatt tcggtcggct cgtcgactac    1740
gacttcaccg cggcgatgga agacgagctc gacgagatcg ccgccggcaa cgagcgccgc    1800
accaactggc tcaacaactt ctactttggt ggcgatcacg tgtgcccga ttcggtagcc     1860
cgatcgggtg gcctcaagaa gcttgtcggg atcaatctcg agggcatcga cgcacgagaa    1920
gtaaactcta tcaagctttt tgacgacacc cacggacgcc ccatatatgt tcgggtgggc    1980
aagaacggtc cctacctgga acgtttggtg gccggcgaca ccggtgagcc cacgccgcag    2040
cgggccaacc tcagcgactc gattaccccg gacgagctga ctctacaggt ggccgaagag    2100
ctctttgcca caccgcaaca gggacggact ttgggcttgg acccagaaac cggccacgag    2160
atcgtggcca gggaaggccg gtttgggccg tatgtgaccg agatcctgcc ggagcctgcg    2220
gctgatgcgg ccgcggccgc tcagggagtc aagaaacgcc agaaggccgc cgggcccaaa    2280
ccgcgcaccg gttcgttgct gcggagcatg gacctacaga cggtcaccct cgaagacgcg    2340
ctgaggctgc tgtcactgcc gcgcgtggtc ggagtggacc ccgcctcggg tgaggagatc    2400
accgcgcaga acgggcgcta cggaccgtat ctaaagcgcg gcaacgattc tcgatcactg    2460
gtcaccgaag accagatatt caccatcacg ctcgacgaag ccctgaagat ctacgcagag    2520
ccgaaacgtc gtggccggca aagcgcttcg gctccgccgc tgcgcgagct gggaacagat    2580
ccggcgtcgg gcaagccaat ggtcatcaag acgccgat tcgggccgta cgtcaccgac      2640
ggtgagacca atgccagcct gcgtaagggc gacgacgtgg cttccataac cgacgagcgc    2700
gccgccgagc tgttggccga tcgccagccc cggggtccgg caaaacgcc agccaggaaa     2760
gctgcccgga aggtgccggc gaagaaggca gccaagcgcg actag                    2805
```

<210> SEQ ID NO 2
<211> LENGTH: 934
<212> TYPE: PRT
<213> ORGANISM: Mycobacterium tuberculosis

<400> SEQUENCE: 2

```
Met Ala Asp Pro Lys Thr Lys Gly Arg Gly Ser Gly Gly Asn Gly Ser
1               5                   10                  15

Gly Arg Arg Leu Val Ile Val Glu Ser Pro Thr Lys Ala Arg Lys Leu
            20                  25                  30

Ala Ser Tyr Leu Gly Ser Gly Tyr Ile Val Glu Ser Ser Arg Gly His
        35                  40                  45

Ile Arg Asp Leu Pro Arg Ala Ala Ser Asp Val Pro Ala Lys Tyr Lys
    50                  55                  60

Ser Gln Pro Trp Ala Arg Leu Gly Val Asn Val Asp Ala Asp Phe Glu
65                  70                  75                  80
```

```
Pro Leu Tyr Ile Ile Ser Pro Glu Lys Arg Ser Thr Val Ser Glu Leu
                85                  90                  95

Arg Gly Leu Leu Lys Asp Val Asp Glu Leu Tyr Leu Ala Thr Asp Gly
            100                 105                 110

Asp Arg Glu Gly Glu Ala Ile Ala Trp His Leu Leu Glu Thr Leu Lys
        115                 120                 125

Pro Arg Ile Pro Val Lys Arg Met Val Phe His Glu Ile Thr Glu Pro
    130                 135                 140

Ala Ile Arg Ala Ala Ala Glu His Pro Arg Asp Leu Asp Ile Asp Leu
145                 150                 155                 160

Val Asp Ala Gln Glu Thr Arg Arg Ile Leu Asp Arg Leu Tyr Gly Tyr
                165                 170                 175

Glu Val Ser Pro Val Leu Trp Lys Lys Val Ala Pro Lys Leu Ser Ala
            180                 185                 190

Gly Arg Val Gln Ser Val Ala Thr Arg Ile Ile Val Ala Arg Glu Arg
        195                 200                 205

Asp Arg Met Ala Phe Arg Ser Ala Ala Tyr Trp Asp Ile Leu Ala Lys
    210                 215                 220

Leu Asp Ala Ser Val Ser Asp Pro Asp Ala Ala Pro Thr Phe Ser
225                 230                 235                 240

Ala Arg Leu Thr Ala Val Ala Gly Arg Val Ala Thr Gly Arg Asp
                245                 250                 255

Phe Asp Ser Leu Gly Thr Leu Arg Lys Gly Asp Glu Val Ile Val Leu
            260                 265                 270

Asp Glu Gly Ser Ala Thr Ala Leu Ala Ala Gly Leu Asp Gly Thr Gln
        275                 280                 285

Leu Thr Val Ala Ser Ala Glu Glu Lys Pro Tyr Ala Arg Arg Pro Tyr
    290                 295                 300

Pro Pro Phe Met Thr Ser Thr Leu Gln Gln Glu Ala Ser Arg Lys Leu
305                 310                 315                 320

Arg Phe Ser Ala Glu Arg Thr Met Ser Ile Ala Gln Arg Leu Tyr Glu
                325                 330                 335

Asn Gly Tyr Ile Thr Tyr Met Arg Thr Asp Ser Thr Leu Ser Glu
            340                 345                 350

Ser Ala Ile Asn Ala Ala Arg Thr Gln Ala Arg Gln Leu Tyr Gly Asp
        355                 360                 365

Glu Tyr Val Ala Pro Ala Pro Arg Gln Tyr Thr Arg Lys Val Lys Asn
    370                 375                 380

Ala Gln Glu Ala His Glu Ala Ile Arg Pro Ala Gly Glu Thr Phe Ala
385                 390                 395                 400

Thr Pro Asp Ala Val Arg Arg Glu Leu Asp Gly Pro Asn Ile Asp Asp
                405                 410                 415

Phe Arg Leu Tyr Glu Leu Ile Trp Gln Arg Thr Val Ala Ser Gln Met
            420                 425                 430

Ala Asp Ala Arg Gly Met Thr Leu Ser Leu Arg Ile Thr Gly Met Ser
        435                 440                 445

Gly His Gln Glu Val Val Phe Ser Ala Thr Gly Arg Thr Leu Thr Phe
    450                 455                 460

Pro Gly Phe Leu Lys Ala Tyr Val Glu Thr Val Asp Glu Leu Val Gly
465                 470                 475                 480

Gly Glu Ala Asp Asp Ala Glu Arg Arg Leu Pro His Leu Thr Pro Gly
                485                 490                 495
```

```
Gln Arg Leu Asp Ile Val Glu Leu Thr Pro Asp Gly His Ala Thr Asn
                500                 505                 510

Pro Pro Ala Arg Tyr Thr Glu Ala Ser Leu Val Lys Ala Leu Glu Glu
            515                 520                 525

Leu Gly Ile Gly Arg Pro Ser Thr Tyr Ser Ser Ile Ile Lys Thr Ile
        530                 535                 540

Gln Asp Arg Gly Tyr Val His Lys Lys Gly Ser Ala Leu Val Pro Ser
545                 550                 555                 560

Trp Val Ala Phe Ala Val Thr Gly Leu Leu Glu Gln His Phe Gly Arg
                565                 570                 575

Leu Val Asp Tyr Asp Phe Thr Ala Ala Met Glu Asp Glu Leu Asp Glu
            580                 585                 590

Ile Ala Ala Gly Asn Glu Arg Arg Thr Asn Trp Leu Asn Asn Phe Tyr
        595                 600                 605

Phe Gly Gly Asp His Gly Val Pro Asp Ser Val Ala Arg Ser Gly Gly
    610                 615                 620

Leu Lys Lys Leu Val Gly Ile Asn Leu Glu Gly Ile Asp Ala Arg Glu
625                 630                 635                 640

Val Asn Ser Ile Lys Leu Phe Asp Asp Thr His Gly Arg Pro Ile Tyr
                645                 650                 655

Val Arg Val Gly Lys Asn Gly Pro Tyr Leu Glu Arg Leu Val Ala Gly
            660                 665                 670

Asp Thr Gly Glu Pro Thr Pro Gln Arg Ala Asn Leu Ser Asp Ser Ile
        675                 680                 685

Thr Pro Asp Glu Leu Thr Leu Gln Val Ala Glu Glu Leu Phe Ala Thr
    690                 695                 700

Pro Gln Gln Gly Arg Thr Leu Gly Leu Asp Pro Glu Thr Gly His Glu
705                 710                 715                 720

Ile Val Ala Arg Glu Gly Arg Phe Gly Pro Tyr Val Thr Glu Ile Leu
                725                 730                 735

Pro Glu Pro Ala Ala Asp Ala Ala Ala Ala Gln Gly Val Lys Lys
            740                 745                 750

Arg Gln Lys Ala Ala Gly Pro Lys Pro Arg Thr Gly Ser Leu Leu Arg
        755                 760                 765

Ser Met Asp Leu Gln Thr Val Thr Leu Glu Asp Ala Leu Arg Leu Leu
    770                 775                 780

Ser Leu Pro Arg Val Val Gly Val Asp Pro Ala Ser Gly Glu Glu Ile
785                 790                 795                 800

Thr Ala Gln Asn Gly Arg Tyr Gly Pro Tyr Leu Lys Arg Gly Asn Asp
                805                 810                 815

Ser Arg Ser Leu Val Thr Glu Asp Gln Ile Phe Thr Ile Thr Leu Asp
            820                 825                 830

Glu Ala Leu Lys Ile Tyr Ala Glu Pro Lys Arg Arg Gly Arg Gln Ser
        835                 840                 845

Ala Ser Ala Pro Pro Leu Arg Glu Leu Gly Thr Asp Pro Ala Ser Gly
    850                 855                 860

Lys Pro Met Val Ile Lys Asp Gly Arg Phe Gly Pro Tyr Val Thr Asp
865                 870                 875                 880

Gly Glu Thr Asn Ala Ser Leu Arg Lys Gly Asp Asp Val Ala Ser Ile
                885                 890                 895

Thr Asp Glu Arg Ala Ala Glu Leu Leu Ala Asp Arg Arg Ala Arg Gly
            900                 905                 910

Pro Ala Lys Arg Pro Ala Arg Lys Ala Ala Arg Lys Val Pro Ala Lys
```

Lys Ala Ala Lys Arg Asp
    930

<210> SEQ ID NO 3
<211> LENGTH: 2520
<212> TYPE: DNA
<213> ORGANISM: Plasmodium falciparum

<400> SEQUENCE: 3

```
atgcaatcaa tggaaataaa tgataataac agtatcaaga atgaaagtac atctgatgat      60
gatatattaa ttaataaaat taaacaaaac ttgggtaata ataaatcatg taattctaga     120
tcttccaaaa aggaatctat aaaaaagcaa aagagcaatt ctgaacttgg tataaaaaag     180
aacacaaaga aatcattagg tataaaaaaa gaggaagaaa aaaaaaaaca aataagcaaa     240
agaaaaagta atgaactaaa agaaaaaaat aatttgaaag agggaaaaaa gaaatatgtg     300
gaaaaaaaat ctagaacagt aaaagatgaa accaagttaa cgaatgttat aaaaaaagaa     360
actcaaaata ataagaaacc taaaaaatta cttaaaaaat cagaagaaaa ttttgaaccca    420
ataaatagat ggtgggaaaa aatagatgat caaacagata tacaatggaa ttatttagaa     480
catcgaggat taatattttc ccctccatac gttcaacatc atgtaccaat ttttttataaa    540
agtataaaaa ttgaattaaa tgcaaaatca gaagaattag ctacctattg gtgtagtgca     600
attggtagtg attattgtac aaaagaaaag tttatattaa attttttttaa aacatttata    660
aatagtttag aaaatgataa tattataaaa caagagaatg aaacgaaatt aaaaaaagga    720
gatatatcta attttaagtt tattgatttt atgccaatca aagatcattt attaaaatta    780
agagaagaaa agttaaataa aacaaaagaa gaaaaagaag aggaaaaaaa aatgagaatg    840
gaaaaagaat taccatatac atatgcgtta gttgattgga ttcgtgaaaa gatatcaagt    900
aataaagcag aaccacctgg gttatttaga ggaagaggag aacatccaaa acaaggttta    960
ttaaaaaaaa gaattttttcc agaagatgtt gtaattaata ttagtaaaga tgcacctgta   1020
ccacgattat atgataatat gtgtggacat aattggggtg atatatatca tgataataaa   1080
gtaacatggt tagcttatta taaagatagt ataaatgatc aaataaaata tactttttta   1140
tctgctcaat caaaatttaa aggatataaa gatcttatga aatatgaaaa tgctcgaaaa   1200
ttaaaatcat gtgttcataa aattagggaa gattataaaa ataaaatgaa aaataaaaat   1260
attattgata acaattagg aacagctgtt tatttaatag attttctagc attaagagta   1320
ggaggagaaa agatatcga tgaagaagca gatactgtag ttgttgtag tttaagagta    1380
gaacatatta gttttgcaca cgatatacct tttaaaagtg tagattcaaa agaacaaaaa   1440
acaaatgatg aaaaagtaaa taaaatacca ttaccaacaa atttagaaag tatttcatca   1500
gaagattgtt atataacttt agattttttta ggaaaagata gtatacgata ttttaataca   1560
gtcaaaatag ataaacaagc atatattaat aataataat tttgtaaaaa taaaaataga   1620
gatgaaggag ttttttgatca aataacttgt tcaaaattaa atgaatatct aaaagaaatt   1680
atgcctactt tatcagctaa agtgtttcgt acatataatg cttcaattac attagatcaa   1740
caattaaaaa gaataaaaga agtttatgga aaaacaacat attcattata ttctggtgaa   1800
acagaattac acaaatcgaa aaaaagaaaa tctagccatt taacttcaga tacaaatata   1860
ttaagtgatg caagtgattc tactattaat gatgtaaata acgagtatga tgaaaatgga   1920
ataaataaaa aactatcata tgctactact gtaggaaaag aaaatgatgt cgatgataaa   1980
```

```
aactcaccaa tagaagttga cgtttcaaat ataaatgaac ttattaattt ttacaataat    2040
gcaaatagag aagtagccat attatgtaac catcaaagaa gtattccaaa acaacatgat    2100
acaactatgt caaaataaaa aaacaaatt  gaattatata atgaagatat aaagaatat     2160 aaaaatatt  tgcaacattt aaaaaaaaat agtgataaaa aatttatctt tgtttcgaaa    2220
gtttctactt tagatggaac tttaagacca aataaagtca agaaaatat  gaagaagaa     2280 tcttgtaaaa aaaactaat  tactcttata aaaaagttg  aattattaaa taaccaaatg    2340
aaagtaagag atgataataa aactattgct ttaggtacat ctaaaattaa ttatatggat    2400
ccaagaataa ctgttgcttt ttgtaaaaaa tttgaaatac ccatagaaaa agtatttaat    2460
agaagtttaa gacttaaatt tccttgggcc atgtttgcta caaaaaattt tacattttaa    2520
```

<210> SEQ ID NO 4
<211> LENGTH: 839
<212> TYPE: PRT
<213> ORGANISM: Plasmodium falciparum

<400> SEQUENCE: 4

```
Met Gln Ser Met Glu Ile Asn Asp Asn Asn Ser Ile Lys Asn Glu Ser
1               5                   10                  15

Thr Ser Asp Asp Ile Leu Ile Asn Lys Ile Lys Gln Asn Leu Gly
            20                  25                  30

Asn Asn Lys Ser Cys Asn Ser Arg Ser Ser Lys Glu Ser Ile Lys
        35                  40                  45

Lys Gln Lys Ser Asn Ser Glu Leu Gly Ile Lys Lys Asn Thr Lys Lys
    50                  55                  60

Ser Leu Gly Ile Lys Lys Glu Glu Lys Lys Lys Gln Ile Ser Lys
65                  70                  75                  80

Arg Lys Ser Asn Glu Leu Lys Glu Lys Asn Asn Leu Lys Glu Gly Lys
                85                  90                  95

Lys Lys Tyr Val Glu Lys Lys Ser Arg Thr Val Lys Asp Glu Thr Lys
            100                 105                 110

Leu Thr Asn Val Ile Lys Lys Glu Thr Gln Asn Asn Lys Lys Pro Lys
        115                 120                 125

Lys Leu Leu Lys Lys Ser Glu Glu Asn Phe Glu Pro Ile Asn Arg Trp
    130                 135                 140

Trp Glu Lys Ile Asp Asp Gln Thr Asp Ile Gln Trp Asn Tyr Leu Glu
145                 150                 155                 160

His Arg Gly Leu Ile Phe Ser Pro Pro Tyr Val Gln His Val Pro
                165                 170                 175

Ile Phe Tyr Lys Ser Ile Lys Ile Glu Leu Asn Ala Lys Ser Glu Glu
            180                 185                 190

Leu Ala Thr Tyr Trp Cys Ser Ala Ile Gly Ser Asp Tyr Cys Thr Lys
        195                 200                 205

Glu Lys Phe Ile Leu Asn Phe Phe Lys Thr Phe Ile Asn Ser Leu Glu
    210                 215                 220

Asn Asp Asn Ile Ile Lys Gln Glu Asn Glu Thr Lys Leu Lys Lys Gly
225                 230                 235                 240

Asp Ile Ser Asn Phe Lys Phe Ile Asp Phe Met Pro Ile Lys Asp His
                245                 250                 255

Leu Leu Lys Leu Arg Glu Glu Lys Leu Asn Lys Thr Lys Glu Glu Lys
            260                 265                 270

Glu Glu Glu Lys Lys Met Arg Met Glu Lys Glu Leu Pro Tyr Thr Tyr
        275                 280                 285
```

```
Ala Leu Val Asp Trp Ile Arg Glu Lys Ile Ser Ser Asn Lys Ala Glu
    290                 295                 300
Pro Pro Gly Leu Phe Arg Gly Arg Gly Glu His Pro Lys Gln Gly Leu
305                 310                 315                 320
Leu Lys Lys Arg Ile Phe Pro Glu Asp Val Val Ile Asn Ile Ser Lys
                    325                 330                 335
Asp Ala Pro Val Pro Arg Leu Tyr Asp Asn Met Cys Gly His Asn Trp
                340                 345                 350
Gly Asp Ile Tyr His Asp Asn Lys Val Thr Trp Leu Ala Tyr Tyr Lys
            355                 360                 365
Asp Ser Ile Asn Asp Gln Ile Lys Tyr Thr Phe Leu Ser Ala Gln Ser
370                 375                 380
Lys Phe Lys Gly Tyr Lys Asp Leu Met Lys Tyr Glu Asn Ala Arg Lys
385                 390                 395                 400
Leu Lys Ser Cys Val His Lys Ile Arg Glu Asp Tyr Lys Asn Lys Met
                405                 410                 415
Lys Asn Lys Asn Ile Ile Asp Lys Gln Leu Gly Thr Ala Val Tyr Leu
                420                 425                 430
Ile Asp Phe Leu Ala Leu Arg Val Gly Gly Lys Asp Ile Asp Glu
                435                 440                 445
Glu Ala Asp Thr Val Gly Cys Cys Ser Leu Arg Val Glu His Ile Ser
450                 455                 460
Phe Ala His Asp Ile Pro Phe Lys Ser Val Asp Ser Lys Glu Gln Lys
465                 470                 475                 480
Thr Asn Asp Glu Lys Val Asn Lys Ile Pro Leu Pro Thr Asn Leu Glu
                485                 490                 495
Ser Ile Ser Ser Glu Asp Cys Tyr Ile Thr Leu Asp Phe Leu Gly Lys
                500                 505                 510
Asp Ser Ile Arg Tyr Phe Asn Thr Val Lys Ile Asp Lys Gln Ala Tyr
            515                 520                 525
Ile Asn Ile Ile Ile Phe Cys Lys Asn Lys Asn Arg Asp Glu Gly Val
            530                 535                 540
Phe Asp Gln Ile Thr Cys Ser Lys Leu Asn Glu Tyr Leu Lys Glu Ile
545                 550                 555                 560
Met Pro Thr Leu Ser Ala Lys Val Phe Arg Thr Tyr Asn Ala Ser Ile
                565                 570                 575
Thr Leu Asp Gln Gln Leu Lys Arg Ile Lys Glu Val Tyr Gly Lys Thr
            580                 585                 590
Thr Tyr Ser Leu Tyr Ser Gly Glu Thr Glu Leu His Lys Ser Lys Lys
            595                 600                 605
Arg Lys Ser Ser His Leu Thr Ser Asp Thr Asn Ile Leu Ser Asp Ala
610                 615                 620
Ser Asp Ser Thr Ile Asn Asp Val Asn Asn Glu Tyr Asp Glu Asn Gly
625                 630                 635                 640
Ile Asn Lys Lys Leu Ser Tyr Ala Thr Thr Val Gly Lys Glu Asn Asp
                645                 650                 655
Val Asp Asp Lys Asn Ser Pro Ile Glu Val Asp Val Ser Asn Ile Asn
                660                 665                 670
Glu Leu Ile Asn Phe Tyr Asn Asn Ala Asn Arg Glu Val Ala Ile Leu
            675                 680                 685
Cys Asn His Gln Arg Ser Ile Pro Lys Gln His Asp Thr Thr Met Ser
            690                 695                 700
```

-continued

```
Lys Ile Lys Lys Gln Ile Glu Leu Tyr Asn Glu Asp Ile Lys Glu Tyr
705                 710                 715                 720

Lys Lys Tyr Leu Gln His Leu Lys Asn Ser Asp Lys Phe Ile
            725                 730                 735

Phe Val Ser Lys Val Ser Thr Leu Asp Gly Thr Leu Arg Pro Asn Lys
            740                 745                 750

Val Lys Glu Asn Met Lys Glu Ser Cys Lys Lys Leu Ile Thr
            755                 760                 765

Leu Ile Lys Lys Val Glu Leu Leu Asn Asn Gln Met Lys Val Arg Asp
            770                 775                 780

Asp Asn Lys Thr Ile Ala Leu Gly Thr Ser Lys Ile Asn Tyr Met Asp
785                 790                 795                 800

Pro Arg Ile Thr Val Ala Phe Cys Lys Lys Phe Glu Ile Pro Ile Glu
                805                 810                 815

Lys Val Phe Asn Arg Ser Leu Arg Leu Lys Phe Pro Trp Ala Met Phe
                820                 825                 830

Ala Thr Lys Asn Phe Thr Phe
            835

<210> SEQ ID NO 5
<211> LENGTH: 67
<212> TYPE: DNA
<213> ORGANISM: Artificial Sequence
<220> FEATURE:
<223> OTHER INFORMATION: Oligonucletide primer or probe

<400> SEQUENCE: 5
cagagtgcgc agttggcctc aatgcacatg tttggctccg agcgagcttc cgcttgacat      60
cccaata                                                                67

<210> SEQ ID NO 6
<211> LENGTH: 77
<212> TYPE: DNA
<213> ORGANISM: Artificial Sequence
<220> FEATURE:
<223> OTHER INFORMATION: Oligonucleotide primer or probe

<400> SEQUENCE: 6
cagagtgcgc agttggtctc tcctcaatgc acatgtttgg ctcctctctg agcgagcttc      60
cgcttgacat cccaata                                                     77

<210> SEQ ID NO 7
<211> LENGTH: 10
<212> TYPE: DNA
<213> ORGANISM: Artificial Sequence
<220> FEATURE:
<223> OTHER INFORMATION: Oligonucletide primer or probe
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t

<400> SEQUENCE: 7 nncgcttgnn                                                             10

<210> SEQ ID NO 8
<211> LENGTH: 108
<212> TYPE: DNA
```

```
<213> ORGANISM: Artificial Sequence
<220> FEATURE:
<223> OTHER INFORMATION: Oligonucletide primer or probe

<400> SEQUENCE: 8
tctagaaagt ataggaactt cgaacgactc agaatgactg tgaagatcgc ttatcctcaa      60
tgcacatgtt tggctcccat tctgagtcgt tcgaagttcc tatacttt                  108

<210> SEQ ID NO 9
<211> LENGTH: 108
<212> TYPE: DNA
<213> ORGANISM: Artificial Sequence
<220> FEATURE:
<223> OTHER INFORMATION: Oligonucletide primer or probe

<400> SEQUENCE: 9
catacattat acgaagttat gagcgtctga gtatgactgt gaagatcgct tatcagtgaa      60
tgcgagtccg tctactcata ctcagacgct cataacttcg tataatgt                  108

<210> SEQ ID NO 10
<211> LENGTH: 96
<212> TYPE: DNA
<213> ORGANISM: Artificial Sequence
<220> FEATURE:
<223> OTHER INFORMATION: Oligonucletide primer or probe

<400> SEQUENCE: 10 attttttaaac tgtgaagatc gcttatttaa aaattttctct aagtcttttt tccctcaat    60 gctgctgctg tactacgaaa aaagacttag aaaaat                               96

<210> SEQ ID NO 11
<211> LENGTH: 108
<212> TYPE: DNA
<213> ORGANISM: Artificial Sequence
<220> FEATURE:
<223> OTHER INFORMATION: Oligonucletide primer or probe

<400> SEQUENCE: 11
attataattt tttggaactt cgaacgactc agaatgactg tgaagatcgc ttatcctcaa     60
tgcacatgtt tggctcccat tctgagtcgt tcgaagttcc aaaaaatt                  108

<210> SEQ ID NO 12
<211> LENGTH: 107
<212> TYPE: DNA
<213> ORGANISM: Artificial Sequence
<220> FEATURE:
<223> OTHER INFORMATION: Oligonucletide primer or probe

<400> SEQUENCE: 12
ttataatttt ttggaacttc gaacgactca gaatgactgt gaagatcgct tatcctcaat     60
gcacatgttt ggctcccatt ctgagtcgtt cgaagttcca aaaaatt                   107

<210> SEQ ID NO 13
<211> LENGTH: 108
<212> TYPE: DNA
<213> ORGANISM: Artificial Sequence
<220> FEATURE:
<223> OTHER INFORMATION: Oligonucletide primer or probe

<400> SEQUENCE: 13
tttataaagt ataggaactt cgaacgactc agaatgactg tgaagatcgc ttatcctcaa     60
tgcacatgtt tggctcccat tctgagtcgt tcgaagttcc tatacttt                  108
```

<210> SEQ ID NO 14
<211> LENGTH: 104
<212> TYPE: DNA
<213> ORGANISM: Artificial Sequence
<220> FEATURE:
<223> OTHER INFORMATION: Oligonucletide primer or probe

<400> SEQUENCE: 14 aaatttttt tggaacttcg aacgactcag aatgaggctc aatctaatgg accctcaatg      60
cacatgtttg gctcccattc tgagtcgttc gaagttccaa aaaa                    104

<210> SEQ ID NO 15
<211> LENGTH: 108
<212> TYPE: DNA
<213> ORGANISM: Artificial Sequence
<220> FEATURE:
<223> OTHER INFORMATION: Oligonucletide primer or probe

<400> SEQUENCE: 15
tttataaagt ataggaactt cgaacgactc agaatgaggc tcaatctaat ggaccctcaa     60
tgcacatgtt tggctcccat tctgagtcgt tcgaagttcc tatacttt                 108

<210> SEQ ID NO 16
<211> LENGTH: 108
<212> TYPE: DNA
<213> ORGANISM: Artificial Sequence
<220> FEATURE:
<223> OTHER INFORMATION: Oligonucletide primer or probe

<400> SEQUENCE: 16
tctagtaagt ataggaactt cgaacgactc agaatgactg tgaagatcgc ttatcctcaa     60
tgcacatgtt tggctcccat tctgagtcgt tcgaagttcc tatactta                 108

<210> SEQ ID NO 17
<211> LENGTH: 110
<212> TYPE: DNA
<213> ORGANISM: Artificial Sequence
<220> FEATURE:
<223> OTHER INFORMATION: Oligonucletide primer or probe

<400> SEQUENCE: 17
atttttctaa gtcttttaga tcgaacgact cagaatgact gtgaagatcg cttatcctca     60
atgcacatgt ttggctccca ttctgagtcg ttcgatctaa aagacttaga              110

<210> SEQ ID NO 18
<211> LENGTH: 14
<212> TYPE: DNA
<213> ORGANISM: Artificial Sequence
<220> FEATURE:
<223> OTHER INFORMATION: Oligonucletide primer or probe
<220> FEATURE:
<221> NAME/KEY: misc_feature
<222> LOCATION: (10)..(10)
<223> OTHER INFORMATION: n is a, c, g, or t

<400> SEQUENCE: 18
tctagtaagn ctta                                                       14

<210> SEQ ID NO 19
<211> LENGTH: 14
<212> TYPE: DNA
<213> ORGANISM: Artificial Sequence
<220> FEATURE:

```
<223> OTHER INFORMATION: Oligonucletide primer or probe
<220> FEATURE:
<221> NAME/KEY: misc_feature
<222> LOCATION: (10)..(10)
<223> OTHER INFORMATION: n is a, c, g, or t

<400> SEQUENCE: 19 attttctan taga                                                      14

<210> SEQ ID NO 20
<211> LENGTH: 23
<212> TYPE: DNA
<213> ORGANISM: Artificial Sequence
<220> FEATURE:
<223> OTHER INFORMATION: Oligonucletide primer or probe

<400> SEQUENCE: 20
cctcaatgca catgtttggc tcc                                           23

<210> SEQ ID NO 21
<211> LENGTH: 23
<212> TYPE: DNA
<213> ORGANISM: Artificial Sequence
<220> FEATURE:
<223> OTHER INFORMATION: Oligonucletide primer or probe

<400> SEQUENCE: 21
cagtgaatgc gagtccgtct act                                           23

<210> SEQ ID NO 22
<211> LENGTH: 23
<212> TYPE: DNA
<213> ORGANISM: Artificial Sequence
<220> FEATURE:
<223> OTHER INFORMATION: Oligonucletide primer or probe

<400> SEQUENCE: 22
cctcaatgct gctgctgtac tac                                           23

<210> SEQ ID NO 23
<211> LENGTH: 18
<212> TYPE: DNA
<213> ORGANISM: Artificial Sequence
<220> FEATURE:
<223> OTHER INFORMATION: Oligonucletide primer or probe

<400> SEQUENCE: 23
actgtgaaga tcgcttat                                                 18

<210> SEQ ID NO 24
<211> LENGTH: 18
<212> TYPE: DNA
<213> ORGANISM: Artificial Sequence
<220> FEATURE:
<223> OTHER INFORMATION: Oligonucletide primer or probe

<400> SEQUENCE: 24
aggctcaatc taatggac                                                 18

<210> SEQ ID NO 25
<211> LENGTH: 108
<212> TYPE: DNA
<213> ORGANISM: Artificial Sequence
<220> FEATURE:
<223> OTHER INFORMATION: Oligonucletide primer or probe

<400> SEQUENCE: 25
```

```
agaaaaattt taaaaaaaac tgtgaagatc gcttattttt taaaaattt ttctaagtct    60 tttagatccc tcaatgctgc tgctgtacta cgatctaaaa gacttaga              108
```

<210> SEQ ID NO 26
<211> LENGTH: 108
<212> TYPE: DNA
<213> ORGANISM: Artificial Sequence
<220> FEATURE:
<223> OTHER INFORMATION: Oligonucletide primer or probe
<400> SEQUENCE: 26

```
tctagaaagt ataggaactt cgaacgactc agaatgaggc tcaatctaat ggaccctcaa    60
tgcacatgtt tggctcccat tctgagtcgt tcgaagttcc tatacttt              108
```

<210> SEQ ID NO 27
<211> LENGTH: 34
<212> TYPE: DNA
<213> ORGANISM: Artificial Sequence
<220> FEATURE:
<223> OTHER INFORMATION: Oligonucletide primer or probe
<400> SEQUENCE: 27

```
ccaaccaacc aaccaaataa gcgatcttca cagt                                34
```

<210> SEQ ID NO 28
<211> LENGTH: 34
<212> TYPE: DNA
<213> ORGANISM: Artificial Sequence
<220> FEATURE:
<223> OTHER INFORMATION: Oligonucletide primer or probe
<400> SEQUENCE: 28

```
ccaaccaacc aaccaagtcc attagattga gcct                                34
```

<210> SEQ ID NO 29
<211> LENGTH: 34
<212> TYPE: DNA
<213> ORGANISM: Artificial Sequence
<220> FEATURE:
<223> OTHER INFORMATION: Oligonucletide primer or probe
<400> SEQUENCE: 29

```
ccaaccaacc aaccaacata gagtcctggt gagc                                34
```

<210> SEQ ID NO 30
<211> LENGTH: 23
<212> TYPE: DNA
<213> ORGANISM: Artificial Sequence
<220> FEATURE:
<223> OTHER INFORMATION: Oligonucletide primer or probe
<400> SEQUENCE: 30

```
gtagtacagc agcagcattg agg                                            23
```

<210> SEQ ID NO 31
<211> LENGTH: 23
<212> TYPE: DNA
<213> ORGANISM: Artificial Sequence
<220> FEATURE:
<223> OTHER INFORMATION: Oligonucletide primer or probe
<400> SEQUENCE: 31

```
ggagccaaac atgtgcattg agg                                            23
```

```
<210> SEQ ID NO 32
<211> LENGTH: 20
<212> TYPE: DNA
<213> ORGANISM: Artificial Sequence
<220> FEATURE:
<223> OTHER INFORMATION: oligonucletide primer or probe

<400> SEQUENCE: 32
agacggactc gcattcactg                                              20
```